US008685928B2

(12) United States Patent
Kufe et al.

(10) Patent No.: US 8,685,928 B2
(45) Date of Patent: *Apr. 1, 2014

(54) ANTAGONISTS OF MUC1

(75) Inventors: Donald W. Kufe, Wellesley, MA (US); Surender Kharbanda, Natick, MA (US)

(73) Assignees: Dana-Farber Cancer Institute, Inc., Boston, MA (US); Genus Oncology, LLC., Chicago, IL (US)

( * ) Notice: Subject to any disclaimer, the term of this patent is extended or adjusted under 35 U.S.C. 154(b) by 232 days.

This patent is subject to a terminal disclaimer.

(21) Appl. No.: 13/026,858

(22) Filed: Feb. 14, 2011

(65) Prior Publication Data
US 2012/0045502 A1 Feb. 23, 2012

Related U.S. Application Data

(60) Provisional application No. 61/303,928, filed on Feb. 12, 2010.

(51) Int. Cl.
*A61K 38/00* (2006.01)
*A61P 35/00* (2006.01)
*A61K 9/127* (2006.01)
*A61K 38/16* (2006.01)

(52) U.S. Cl.
USPC ........... 514/19.3; 424/450; 514/1.1; 514/21.3

(58) Field of Classification Search
None
See application file for complete search history.

(56) References Cited

U.S. PATENT DOCUMENTS

| | | | |
|---|---|---|---|
| 5,595,756 A | 1/1997 | Bally et al. | |
| 5,912,232 A | 6/1999 | Talmadge | |
| 6,261,569 B1 | 7/2001 | Comis et al. | 424/204.1 |
| 6,548,643 B1 | 4/2003 | McKenzie et al. | |
| 7,118,862 B2 | 10/2006 | Kufe et al. | |
| 7,183,059 B2 | 2/2007 | Verdine et al. | 435/7.1 |
| 7,192,713 B1 | 3/2007 | Verdine et al. | 435/7.1 |
| 7,247,297 B2 | 7/2007 | Weichselbaum et al. | |
| 7,556,935 B2 | 7/2009 | Kufe et al. | |
| 7,576,057 B2 | 8/2009 | Scribner et al. | 514/1.1 |
| 7,589,170 B1 | 9/2009 | Smythe et al. | 530/317 |
| 7,705,012 B2 | 4/2010 | Pisano et al. | 514/283 |
| 8,524,669 B2 * | 9/2013 | Kufe et al. | 514/19.3 |
| 2002/0044943 A1 | 4/2002 | Longenecker et al. | |
| 2002/0086829 A1 | 7/2002 | Gefter | |
| 2005/0042209 A1 | 2/2005 | Kufe et al. | |
| 2005/0053606 A1 | 3/2005 | Kufe et al. | |
| 2005/0089957 A1 | 4/2005 | Goddard et al. | |
| 2005/0271650 A1 | 12/2005 | Freimark et al. | |
| 2005/0282744 A1 | 12/2005 | Hollingsworth et al. | |
| 2006/0293234 A1 | 12/2006 | Schroeder | |
| 2007/0071675 A1 | 3/2007 | Wu et al. | |
| 2007/0105767 A1 | 5/2007 | Kharbanda et al. | |
| 2007/0202134 A1 | 8/2007 | Kufe et al. | |
| 2007/0207209 A1 | 9/2007 | Murphy et al. | |
| 2008/0286264 A1 | 11/2008 | Kufe | |
| 2009/0047307 A1 | 2/2009 | Harrop et al. | |
| 2009/0087437 A1 | 4/2009 | Kufe | 424/139.1 |
| 2009/0092600 A1 | 4/2009 | Kufe | |
| 2009/0098054 A1 | 4/2009 | Kufe | |
| 2009/0136520 A1 | 5/2009 | Kufe | |
| 2009/0232812 A1 | 9/2009 | Kufe et al. | |
| 2009/0326192 A1 | 12/2009 | Nash et al. | 530/317 |
| 2010/0125055 A1 * | 5/2010 | Kufe et al. | 514/13 |
| 2011/0015138 A1 * | 1/2011 | Kufe et al. | 514/21.4 |
| 2011/0125055 A1 | 5/2011 | Privitera et al. | |
| 2011/0251246 A1 | 10/2011 | Kufe et al. | |
| 2012/0172312 A1 * | 7/2012 | Kufe et al. | 514/19.3 |
| 2013/0039974 A1 * | 2/2013 | Kufe et al. | 424/450 |

FOREIGN PATENT DOCUMENTS

| | | | | |
|---|---|---|---|---|
| EP | 1538164 A1 | 6/2005 | | |
| WO | WO 00/034468 | 6/2000 | | |
| WO | WO 01/18035 | 3/2001 | | |
| WO | WO 01/57068 | 8/2001 | | |
| WO | WO2005101021 | * 10/2005 | ............ | G01N 33/74 |
| WO | WO 2008/121767 | 10/2008 | | |

OTHER PUBLICATIONS

National Cancer Institute—Types of Leukemia, Published Nov. 25, 2008. Accessed online at http://www.cancer.gov/cancertopics/wyntk/leukemia/page3 on Apr. 12, 2013, 2 pages.*
Agata et al.,"MUC1 oncoportein blocks death receptor-mediated apoptosis by inhibiting recruitment of caspase-8," *Cancer Res.*, 68(15):6136-6144, 2008.
Ahmad et al.,"MUC1-C oncoprotein functions as a direct activator of the nuclear factor-kappaB p65 transcription factor," *Cancer Res.*, 69(17):7013-21, 2009.
Ahmad et al.,"MUC1-C oncoprotein promotes STAT3 activation in an autoinductive regulatory loop," *Sci. Signal.*, 4(160):ra9, Feb. 15, 2011.
Fischer, "Cellular Update Mechanisms and Potential Therapeutic Utility of Peptidic Cell Delivery Vectors: Progress 2001-2006," *Med. Res. Rev.*, 27(6):755-796, 2007.
International Search Report and Written Opinion issued in International application No. PCT/US11/24760, dated May 27, 2011.
Joshi et al.,"MUC1 oncoprotein is a druggable target in human prostate cancer cells," *Mol. Cancer Ther.*, 8(110:3056-3065, 2009.
Li et al., "DF3/MUC1 signaling in multiple myeloma cells is regulated by interleukin-7," *Cancer Biol. Ther.*, 2(2):I87-193, 2003.
Li et al., "Interaction of glycogen synthase kinase 3β with DF3/MUC1 carcinoma-associated antigen and β-catenin," *Molecular and Cellular Biology*, 18(12):7216-7224, 1998.
Mukherjee et al., "Progression of pancreatic adenocarcinoma is significantly impeded with a combination of vaccine and COX-2 inhibition," *J. Immunol.*, 182(1):216-224, 2009.

(Continued)

*Primary Examiner* — Marcela M Cordero Garcia
(74) *Attorney, Agent, or Firm* — Parker Highlander PLLC

(57) ABSTRACT

The present invention is directed to improved compositions for cellular delivery of peptides. Using segments of only 3-5 positively-charged residues, one can effectively transfer peptides, including therapeutic peptides, into cells. Also provided are modified peptides such as those include stapled and cyclized peptide technology, as well as peptoids/peptidomimetics.

27 Claims, 7 Drawing Sheets

(56) References Cited

OTHER PUBLICATIONS

Raina et al., "Dependence on the MUC1-C oncoprotein in non-small cell lung cancer cells," Mol. Cancer Ther., 10(5):806-816, May 2011. E-published Mar. 18, 2011.
Raina et al., "Direct targeting of the mucin 1 oncoprotein blocks survival and tumorigenicity of human breast carcinoma cells," Cancer Res., 69(12):5133-5141, 2009.
Raina et al.,"MUC1 oncoprotein suppresses activation of the ARF-MDM2-p53 pathway," Cancer Biol. Ther., 7(12):1959-1967, Dec. 7, 2008.
Shepherd et al., "Modular alpha-helical mimetics with antiviral activity against respiratory syncitial virus," JACS, 128(40):13284-13289, 2006.
Yin et al.,"MUC1 oncoprotein promotes autophagy in a survival response to glucose deprivation," Int. J. Oncol., 34(6):1691-1699, 2009.
Yin et al.,"MUC1-C oncoprotein suppresses reactive oxygen species-induced terminal differentiation of acute myelogenous leukemia cells," Blood., 1 17(18):4863-4870, May 5, 2011. E-published Mar. 21, 2011.
Yin et al., "Survival of human multiple myeloma cells is dependent on MUC1 C-terminal transmembrane subunit oncoprotein function," Mol. Pharmacol., 78(2):166-174, 2010.
Zhou et al.,"MUC1 oncoprotein is a target for small molecule inhibitors," Molecular Pharmacology, Published online before print Feb. 23, 2011, doi: 10.1124/mol.110.070797.
Abe and Kufe, "Structural analysis of the DF3 human breast carcinoma-associated protein," Cancer Res., 49(1):2834-2839, 1989.
Ahmad et al., "MUC1 oncoprotein activates the IkappaB kinase beta complex and constitutive NF-kappaB signalling," Nat. Cell Biol., 9:1419-1427, 2007.
Ahmad et al., "Triterpenoid CDDO-Me blocks the NF-kappaB pathway by direct inhibition of IKKbeta on Cys-179," J. Biol. Chem., 281:35764-9, 2006.
Anderson et al., "Multiple myeloma: New insights and therapeutic approaches," Hematology, 1:147-165, 2000.
Arkin et al.. "Structural aspects of oligomerization taking place between the transmembrane a-helices of bitopic membrane proteins," Biochimica et Biophysica Acta, 1565:347-363.2002.
Aurerbach et al., "Angiogenesis assays: Problems and pitfalls," Cancer and Metastasis Reviews, 19:167-172,2000.
Baldus et al., "MUC1 and nuclear beta-catenin are coexpressed at the invasion front of colorectal carcinomas and are both correlated with tumor prognosis," Clin. Cancer Res., 10(8):2790-2796, 2004.
Beatty et al., "Cutting edge: Transgenic expression of human MUC1 in IL-10 -/- Mice accelerates inflammatory bowel disease and progression to colon cancer," J. Immunol., 179:735-739, 2007.
Begum et al., "MUC1 based breast cancer vaccines: role of post translational modifications," J. Ayub. Med Coll. Abbottabad., 20(4):130-133, 2008.
Bitler et al., "Intracellular MUC1 peptides inhibit cancer progression," Clin. Canc. Res., 15 (1): 100-109, 2009.
English Translation of Ling et al. "MUC1 C-terminal Heterodimer and Its Tumorgenicity," Progress in Biochemistry and Biophysics, 34(4): 375-381, 2007.
English Translation of Office Communication issued in corresponding Chinese Patent Application 200980149998.9, dated Mar. 4, 2013.
Gura, "Systems for identifying new drugs are often faulty," Science, 278:1041-1042, 1997.
Hodel ei al., "The three-dimensional structure of the autoproteolytic, nuclear pore-targeting domain of the human nucleoporin Nup98," Mol. Cell, 10(2):347-58, 2002.
Hruby, "Designing peptide receptor agonists and antagonists," Nature Reviews. Drug Discovery, 1:847-585, 2002.
Hu at al.,"MUC1 cytoplasmic tail: a potential therapeutic target for ovarian cancer," Future Drugs, 6(8).1261-1271, 2006.
Huang at al., "MUC1 cytoplasmic domain coactivates Wnt target gene transcription and confers transformation." Cancer Biol. Ther., 2(6): 702-706, 2003.
Huang at al., "MUC1 oncoprotein blocks glycogen synthase kinase 3beta-mediated phosphorylation and degradation of beta-catenin," Cancer Res., 65:10413-10422, 2005.
Jain, "Barriers to drug delivery in solid tumors," Scientific American, 271(1): 58-65, 1994.
Kau et al., "Nuclear transport and cancer: from mechanism to intervention," Nat. Rev. Cancer, 4(2):106-17, 2004.
Kawano et al.,"MUC1 oncoprotein promotes growth and survival of human multiple myeloma cells," International Journal of Oncology, 33:153-159, 2008.
Khodarev et al., "Cooperativity of the MUC1 oncoprotein and STAT1 pathway in poor prognosis human breast cancer," Oncogene, 29(6):920-929, 2010. B-published Nov. 16, 2009.
Kinkiugh et al., "Recycling of MUC1 is dependent on its palmitoylation," The Journal of Biological Chemistry, 281(17):12112-12122, 2006.
Kufe et al., "Differential reactivity of a novel monoclonal antibody (DF3) with human malignant versus benign breast tumors," Hybridoma, 3 (3):223-232, 1984.
Kufe, "Functional targeting of the MUC1 oncogene in human cancers," Cancer Biology & Therapy, 8 (13): 1201-1207, 2009.
Kufe, "Human MUC1 oncoprotein is of functional importance fo the development of prostate cancer," Award No. W81XWH-08-1-0093, Annual Report, prepared for U.S. Army Medical Research and Materiel Command, Mar. 2009.
Kufe, "Mucins in cancer: function, prognosis and therapy," Nat. Rev. Cancer, 9 (12); 874-885, 2009.
Kufe, "Targeting the human MUC1 oncoprotein: a tale of two proteins," Cancer Biol. Ther., 7 (1): 81-84, 2008.
Leng et al., "Nuclear import of the MUC1-C oncoprotein is mediated by nucleoporin-Nup62," The Journal of Biological Chemistry, 282 (27): 19321-19330, 2007.
Levitin et al., "The MUC1 SEA module is a self-cleaving domain," J. Biol. Chem., 280:33374-33386, 2005.
Li and Cozzi, "MUC1 is a promising therapeutic target for prostate cancer therapy," Current Cancer Drugs Targets, 7:259-271, 2007.
Li et al., "Heregulin targets ganinia-catenin to the nucleolus by a mechanism dependent on the DF3/MUC1 oncoprotein," Mol. Cancer Res., 1 (10):765-775, 2003.
Li et al., "Human DE3/MUC1 carcinoma-associated protein functions as an oncogene," Oncogene, 22 (38): 6107-6110, 2003.
Li et al., "The c-Src tyrosine kinase regulates signaling of the human DF3/MUC1 carcinoma-associated antigen with GSK3 beta and beta-catenin," J. Biol. Chem., 276(9):6061-6064, 2001.
Li et al., "The epidermal growth factor receptor regulates interaction of the human DF3/MUC1 carcinoma antigen with c-Src and beta-catenin," J. Biol. Chem., 276:35239-35242, 2001.
Ligtenberg et al., "Cell-associated episialin is a complex containing two proteins derived from a common precursor," J. Biol. Chem., 267 (9), 6171-6177, 1992.
Ling et al. "MUC1 C-terminal Heterodimer and Its Tumorgenicity," Progress in Biochemistry and Biophysics, 34(4): 375-381, 2007. (Chinese publication; English abstract).
Macao, "Autoproteolysis coupled to protein folding in the SEA domain of the membrane-bound MUC1 mucin," Nat. Struct. Mol. Biol., 13 (1), 71-76, 2006.
Neidle, Stephen, Ed., "Failure modes in the discovery process," In: Cancer Drug Design and Discovery. Elsevier/Academic Press, Chapter 18, pp. 427-431, 2008.
Notice of Allowance (Corrected Notice of Allowability) issued in U.S. Appl. No. 12/789,127, dated Mar. 6, 2013.
Notice of Allowance issued in U.S. Appl. No. 12/789,127, dated Jan. 23, 2012.
Office Communication issued in Australian Patent Application No. 2010253834, dated Mar. 8, 2013.
Office Communication issued in European Patent Application No. 09740811.6, dated Jun. 22, 2012.
Office Communication issued in U.S. Appl. No. 12/580,865, dated May 24, 2012.
Office Communication issued in U.S. Appl. No. 12/580,865, dated Dec. 27, 2011.
Office Communication issued in U.S. Appl. No. 12/580,865, dated Nov. 2, 2012.

(56) References Cited

OTHER PUBLICATIONS

Office Communication issued in U.S. Appl. No. 12/789,127, dated Mar. 28, 2012.
Office Communication issued in U.S. Appl. No. 12/789,127, dated Jul. 5, 2012.
PCT International Search Report and Written Opinion, issued in International application No. PCT/US2009/061051, dated Nov. 26. 2010.
PCT International Search Report and Written Opinion, issued in International patent Application No. PCT/US10/36436, dated Oct. 19, 2010.
Peczuh et al., "Peptide and protein recognition by designed molecules," *Chem. Rev.*, 100:2479-2494, 2000.
Raina et al., "MUC1 oncoprotein blocks nuclear targeting of c-Abl in the apoptotic response to DNA damage," *EMBO J.*, 25:3774-3783, 2006.
Raina et al., "The MUC1 oncoprotein activates the anti-apoptotic phosphoinositide 3-kinase/AKT and Bcl-xL pathways in rat 3Y1 fibroblasts," *J. Biol. Chem.*, 279 (20):20607-20612, 2004.
Ramasamy et al., "The MUC1 and galectin-3 oncoproteins function in a microRNA-dependent regulatory loop," *Mol. Cell*, 27 (6):992-1004, 2007.
Ren et al., "Human MUC1 carcinoma-associated protein confers resistance to genotoxic anticancer agents," *Cancer Cell*. 5 (2):163-175, 2004.
Ren et al., "MUC1 oncoprotein functions in activation of fibroblast growth factor receptor signaling," *Mol. Cancer Res.*, 4 (11): 873-883, 2006.
Ren et al., "MUC1 oncoprotein is targeted to mitochondria by heregulin-induced activation of c-Src and the molecular chaperone HSP90," *Oncogene*, 25 (1):20-31, 2006,.
Ren et al., "Protein kinase C delta regulates function of the DE3/MUC1 carcinoma antigen in beta-catenin signaling," *J. Biol. Chem.*, 277 (20):17616-17622, 2002.
Response to Office Communication issued in U.S. Appl. No. 12/580,865, dated Feb. 23, 2012.
Response to Office Communication issued in U.S. Appl. No. 12/580,865, dated Sep. 24, 2012.
Response to Office Communication issued in U.S. Appl. No. 12/580,865, dated Feb. 4, 2013.
Response to Office Communication issued in U.S. Appl. No. 12/789,177, dated Apr. 30, 2012.
Response to Office Communication issued in U.S. Appl. No. 12/789,127, dated Jan. 4, 2013.
Schroeder et al.,"MUC1 overexpression results in mammary gland tumorieenesis and prolonged alveolar differentiation," *Oncogene*, 23 (34):5739-5747, 2004.
Schroeder et al., "Transgenic MUC1 interacts with epidermal growth factor receptor and correlates with mitogen-activated protein kinase activation in the mouse mammary gland." *J. Biol. Chem.*, 276(16):13057-13064 2001.
Spicer et al., "Molecular cloning and analysis of the mouse homologue of the tumor-associated mucin, MUC1, reveals conservation of potential O-glycosylation.sites, transmembrance, and cytoplasmic domains, and a loss of minisatellite—like polymorphism," *J. Biol. Chem.*, 266(23): 15099-15109, 1991.
Sporn and Suh, "Chemoprevention of cancer," *Carciogenesis*, 21:525-530, 2000.
Supplementary European Search Report issued in European Patent Application No. 10781227.3, dated Dec. 3, 2012.
Truscott et al., "A J.-protein is an essential subunit of the presequence translocase-associated protein import motor of mitochondria," *J. Cell Biol.*, 163(4):707-713, 2003.
Tsutsumida et. al., "RNA interference suppression of MUC1 reduced the growth rate and metastatic phenotype of human pancreatic cancer cells," *Clin. Cancer Rev.*, 12(10):2976-2987, 2006.
Vermeer et al.. "Segregation of receptor and ligand regulates activation of epithelial growth factor receptor," *Nature*, 422(6929):322-6, 2003.
Wei et al., "Human MUC1 oncoprotein regulates p53-responsive gene transcription in the genotoxic stress response," *Cancer Cell*, 7 (2):167-178, 2005.
Wei et al., "MUC1 oncoprotein stabilizes and activates estrogen receptor alpha," *Mol. Cell*. 21 (2): 295-305, 2006.
Weis, "Regulating access to the genome: nucleocytoplasmic transport throughout the cell cycle," *Cell*, 112(4):441-51, 2003.
Wen et al., "Nuclear association of the cytoplasmic tail of MUC1 and beta-catenin," *J Biol. Chem.*, 278 (39):38029-38039, 2003.
Yamamoto et al., "Interaction of the DF3/MUC1 breast carcinoma-associated antigen and beta-catenin in cell adhesion," *J. Biol. Chem.*, 272 (19):12492-12494, 1997.
Yin et al., "Human MUC1 carcinoma antigen regulates intracellular oxidant levels and the apoptotic response to oxidative stress," *J. Biol. Chem.*, 278 (37):35458-35464, 2003.
Yin et al., "MUC1 oneoptotein activates the FOXO3a transcription factor in a survival response to oxidative stress," *J. Biol. Chem.*, 279 (44):45721-45727, 2004.
Yin et al., "Mucin 1 oncoprotein blocks hypoxia-inducible factor lalpha activation in a survival response to hypoxia," *J. Biol. Chem.*, 282 (1):257-266, 2007.
Young et al., "Molecular chaperones Hsp90 and Hsp70 deliver preproteins to the mitochondrial import receptor Tom70," *Cell*. 112 (1): 41-50, 2003.

\* cited by examiner

| MUC1-CD | | |
|---|---|---|
| CQCRRKNYGQLDIFPARDTYHPMSEYPTYHTHGRYVPPSSTDRSPYEKVSAGNGGSSLYTNPAVAAASL | | |
| GO-201: | NH2-[dR]9- C Q C R R K N Y G Q L D I F P –COOH | TFA |
| GO-202: | NH2-[dR]9- C Q C R R K N –COOH | TFA |
| GO-203: | NH2-[dR]9- dC dQ dC dR dR dK dN-COOH | TFA |
| GO-203-1: | Acetyl- [dR]9 - dC dQ dC dR dR dK dN –NH2 | TFA |
| GO-203-2: | Acetyl- [dR]9 - dC dQ dC dR dR dK dN –NH2 | HCL |
| GO-203a: | NH2-dR- dR- dR - dC dQ dC dR dR dK dN dR -COOH | TFA |
| GO-203b: | NH2-dR- dR- dC dQ dC dR dR dK dN dR -COOH | TFA |
| GO-203c: | Acetyl-dR- dR - dC dQ dC dR dR dK dN- NH2 | TFA |
| GO-203-cyc: | Acetyl- [dR]9 - dC dQ dC dR dR dK dN –NH2 | TFA |
| GO-203-cyc-1: | Acetyl-dR- dR - dC dQ dC dR dR dK dN- NH2 | TFA |
| GO-204: | NH2- dC dQ dC dR dR dK dN-[dR]9 -COOH | TFA |
| GO-205: | Acetyl- [dR]9 - dN dK dR dR dC dQ dC –NH2 | TFA |
| GO-206: | NH2- dN dK dR dR dC dQ dC--[dR]9 -COOH | TFA |
| GO-207: | NH2-[dR]9- dC dQ dC dR dR dK -COOH | TFA |
| GO-208: | NH2-[dR]9- dC dQ dC dR dR -COOH | TFA |
| GO-209: | NH2-[dR]9- dC dQ dC dR -COOH | TFA |
| GO-210: | NH2-[dR]9- dC dQ dC-COOH | TFA |
| CP-1: | NH2-[dR]9- A Q A R R K N Y G Q L D I F P –COOH | TFA |
| CP-2: | NH2-[dR]9- dA dQ dA dR dR dK dN-COOH | TFA |

FIG. 3

MUC1 Peptoid
Ac-CQCRRKN-NH₂
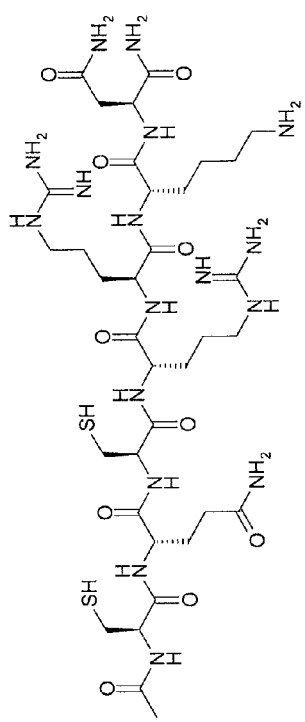
Me-CQCRRKN Peptoids
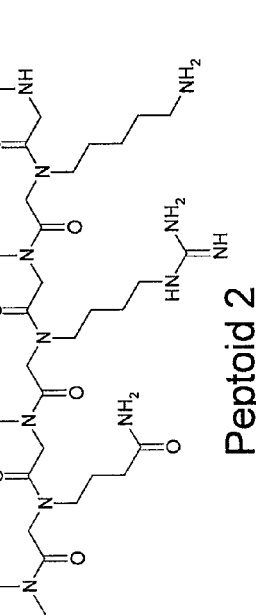
Peptoid 2
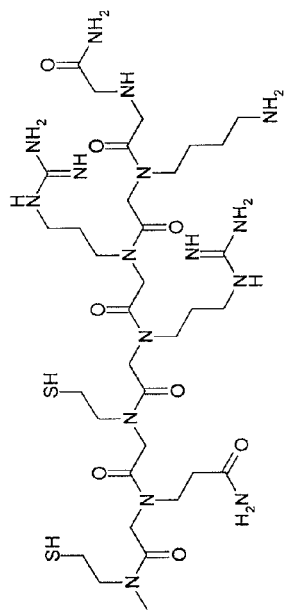
Peptoid 1
FIG. 10

SEQUENCE LISTING

<160> NUMBER OF SEQ ID NOS: 94

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide

```
<400> SEQUENCE: 1

Cys Gln Cys Arg
1

<210> SEQ ID NO 2
<211> LENGTH: 5
<212> TYPE: PRT
<213> ORGANISM: Artificial Sequence
<220> FEATURE:
<223> OTHER INFORMATION: Synthetic peptide

<400> SEQUENCE: 2

Cys Gln Cys Arg Arg
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic peptide

<400> SEQUENCE: 3

Cys Gln Cys Arg Arg Arg
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic peptide

<400> SEQUENCE: 4

Cys Gln Cys Arg Arg Arg Arg
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic peptide

<400> SEQUENCE: 5

Cys Gln Cys Arg Arg Lys
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic peptide

<400> SEQUENCE: 6

Cys Gln Cys Arg Arg Lys Asn
1               5

<210> SEQ ID NO 7
<211> LENGTH: 159
<212> TYPE: PRT
<213> ORGANISM: Artificial Sequence
<220> FEATURE:
<223> OTHER INFORMATION: Synthetic peptide

<400> SEQUENCE: 7
```

```
Gly Ser Val Val Gln Leu Thr Leu Ala Phe Arg Glu Gly Thr Ile
1               5                   10                  15

Asn Val His Asp Val Glu Thr Gln Phe Asn Gln Tyr Lys Thr Glu Ala
            20                  25                  30

Ala Ser Arg Tyr Asn Leu Thr Ile Ser Asp Val Ser Val Ser Asp Val
        35                  40                  45

Pro Phe Pro Phe Ser Ala Gln Ser Gly Ala Gly Val Pro Gly Trp Gly
    50                  55                  60

Ile Ala Leu Leu Val Leu Val Cys Val Leu Val Ala Leu Ala Ile Val
65                  70                  75                  80

Tyr Leu Ile Ala Leu Ala Val Cys Gln Cys Arg Arg Lys Asn Tyr Gly
                85                  90                  95

Gln Leu Asp Ile Phe Pro Ala Arg Asp Thr Tyr His Pro Met Ser Glu
            100                 105                 110

Tyr Pro Thr Tyr His Thr His Gly Arg Tyr Val Pro Pro Ser Ser Thr
        115                 120                 125

Asp Arg Ser Pro Tyr Glu Lys Val Ser Ala Gly Asn Gly Gly Ser Ser
    130                 135                 140

Leu Ser Tyr Thr Asn Pro Ala Val Ala Ala Thr Ser Ala Asn Leu
145                 150                 155

<210> SEQ ID NO 8
<211> LENGTH: 23
<212> TYPE: PRT
<213> ORGANISM: Artificial Sequence
<220> FEATURE:
<223> OTHER INFORMATION: Synthetic peptide

<400> SEQUENCE: 8

Gly Ala Leu Phe Leu Gly Trp Leu Gly Ala Ala Gly Ser Thr Met Gly
1               5                   10                  15

Ala Lys Lys Lys Arg Lys Val
            20

<210> SEQ ID NO 9
<211> LENGTH: 16
<212> TYPE: PRT
<213> ORGANISM: Artificial Sequence
<220> FEATURE:
<223> OTHER INFORMATION: Synthetic peptide

<400> SEQUENCE: 9

Arg Gln Ile Lys Ile Trp Phe Gln Asn Arg Arg Met Lys Trp Lys Lys
1               5                   10                  15

<210> SEQ ID NO 10
<211> LENGTH: 7
<212> TYPE: PRT
<213> ORGANISM: Artificial Sequence
<220> FEATURE:
<223> OTHER INFORMATION: Synthetic peptide

<400> SEQUENCE: 10

Arg Arg Met Lys Trp Lys Lys
1               5

<210> SEQ ID NO 11
<211> LENGTH: 16
<212> TYPE: PRT
<213> ORGANISM: Artificial Sequence
<220> FEATURE:
<223> OTHER INFORMATION: Synthetic peptide
```

<400> SEQUENCE: 11

Arg Arg Trp Arg Arg Trp Trp Arg Arg Trp Trp Arg Trp Arg Arg
1               5                   10                  15

<210> SEQ ID NO 12
<211> LENGTH: 18
<212> TYPE: PRT
<213> ORGANISM: Artificial Sequence
<220> FEATURE:
<223> OTHER INFORMATION: Synthetic peptide

<400> SEQUENCE: 12

Arg Gly Gly Arg Leu Ser Tyr Ser Arg Arg Arg Phe Ser Thr Ser Thr
1               5                   10                  15

Gly Arg

<210> SEQ ID NO 13
<211> LENGTH: 11
<212> TYPE: PRT
<213> ORGANISM: Artificial Sequence
<220> FEATURE:
<223> OTHER INFORMATION: Synthetic peptide

<400> SEQUENCE: 13

Tyr Gly Arg Lys Lys Arg Arg Gln Arg Arg
1               5                   10

<210> SEQ ID NO 14
<211> LENGTH: 9
<212> TYPE: PRT
<213> ORGANISM: Artificial Sequence
<220> FEATURE:
<223> OTHER INFORMATION: Synthetic peptide

<400> SEQUENCE: 14

Arg Lys Lys Arg Arg Gln Arg Arg
1               5

<210> SEQ ID NO 15
<211> LENGTH: 11
<212> TYPE: PRT
<213> ORGANISM: Artificial Sequence
<220> FEATURE:
<223> OTHER INFORMATION: Synthetic peptide

<400> SEQUENCE: 15

Tyr Ala Arg Ala Ala Ala Arg Gln Ala Arg Ala
1               5                   10

<210> SEQ ID NO 16
<211> LENGTH: 8
<212> TYPE: PRT
<213> ORGANISM: Artificial Sequence
<220> FEATURE:
<223> OTHER INFORMATION: Synthetic peptide

<400> SEQUENCE: 16

Arg Arg Arg Arg Arg Arg Arg Arg
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic peptide

<400> SEQUENCE: 17

Lys Lys Lys Lys Lys Lys Lys Lys
1               5

<210> SEQ ID NO 18
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (25)..(25)
<223> OTHER INFORMATION: Xaa can be any naturally occurring amino acid

<400> SEQUENCE: 18

Gly Trp Thr Leu Asn Ser Ala Gly Tyr Leu Leu Gly Lys Ile Asn Leu
1               5                   10                  15

Lys Ala Leu Ala Ala Leu Ala Lys Xaa Ile Leu
            20                  25

<210> SEQ ID NO 19
<211> LENGTH: 18
<212> TYPE: PRT
<213> ORGANISM: Artificial Sequence
<220> FEATURE:
<223> OTHER INFORMATION: Synthetic peptide

<400> SEQUENCE: 19

Leu Leu Ile Leu Leu Arg Arg Arg Ile Arg Lys Gln Ala Asn Ala His
1               5                   10                  15

Ser Lys

<210> SEQ ID NO 20
<211> LENGTH: 16
<212> TYPE: PRT
<213> ORGANISM: Artificial Sequence
<220> FEATURE:
<223> OTHER INFORMATION: Synthetic peptide

<400> SEQUENCE: 20

Ser Arg Arg His His Cys Arg Ser Lys Ala Lys Arg Ser Arg His His
1               5                   10                  15

<210> SEQ ID NO 21
<211> LENGTH: 11
<212> TYPE: PRT
<213> ORGANISM: Artificial Sequence
<220> FEATURE:
<223> OTHER INFORMATION: Synthetic peptide

<400> SEQUENCE: 21

Asn Arg Ala Arg Arg Asn Arg Arg Arg Val Arg
1               5                   10

<210> SEQ ID NO 22
<211> LENGTH: 15
<212> TYPE: PRT
<213> ORGANISM: Artificial Sequence
<220> FEATURE:
<223> OTHER INFORMATION: Synthetic peptide

<400> SEQUENCE: 22

Arg Gln Leu Arg Ile Ala Gly Arg Arg Leu Arg Gly Arg Ser Arg
1               5                   10                  15

```
<210> SEQ ID NO 23
<211> LENGTH: 13
<212> TYPE: PRT
<213> ORGANISM: Artificial Sequence
<220> FEATURE:
<223> OTHER INFORMATION: Synthetic peptide

<400> SEQUENCE: 23

Lys Leu Ile Lys Gly Arg Thr Pro Ile Lys Phe Gly Lys
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Synthetic peptide

<400> SEQUENCE: 24

Arg Arg Ile Pro Asn Arg Arg Pro Arg Arg
1               5                   10

<210> SEQ ID NO 25
<211> LENGTH: 18
<212> TYPE: PRT
<213> ORGANISM: Artificial Sequence
<220> FEATURE:
<223> OTHER INFORMATION: Synthetic peptide

<400> SEQUENCE: 25

Lys Leu Ala Leu Lys Leu Ala Leu Lys Ala Leu Lys Ala Ala Leu Lys
1               5                   10                  15

Leu Ala

<210> SEQ ID NO 26
<211> LENGTH: 14
<212> TYPE: PRT
<213> ORGANISM: Artificial Sequence
<220> FEATURE:
<223> OTHER INFORMATION: Synthetic peptide

<400> SEQUENCE: 26

Lys Leu Ala Lys Leu Ala Lys Lys Leu Ala Lys Leu Ala Lys
1               5                   10

<210> SEQ ID NO 27
<211> LENGTH: 27
<212> TYPE: PRT
<213> ORGANISM: Artificial Sequence
<220> FEATURE:
<223> OTHER INFORMATION: Synthetic peptide

<400> SEQUENCE: 27

Gly Ala Leu Phe Leu Gly Phe Leu Gly Ala Ala Gly Ser Thr Asn Gly
1               5                   10                  15

Ala Trp Ser Gln Pro Lys Lys Lys Arg Lys Val
            20                  25

<210> SEQ ID NO 28
<211> LENGTH: 21
<212> TYPE: PRT
<213> ORGANISM: Artificial Sequence
<220> FEATURE:
<223> OTHER INFORMATION: Synthetic peptide

<400> SEQUENCE: 28
```

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 29
<211> LENGTH: 20
<212> TYPE: PRT
<213> ORGANISM: Artificial Sequence
<220> FEATURE:
<223> OTHER INFORMATION: Synthetic peptide

<400> SEQUENCE: 29

Leu Lys Lys Leu Leu Lys Lys Leu Leu Lys Lys Leu Leu Lys Lys Leu
1               5                   10                  15

Leu Lys Lys Leu
            20

<210> SEQ ID NO 30
<211> LENGTH: 34
<212> TYPE: PRT
<213> ORGANISM: Artificial Sequence
<220> FEATURE:
<223> OTHER INFORMATION: Synthetic peptide

<400> SEQUENCE: 30

Gln Ala Ala Thr Ala Thr Arg Gly Arg Ser Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 31
<211> LENGTH: 23
<212> TYPE: PRT
<213> ORGANISM: Artificial Sequence
<220> FEATURE:
<223> OTHER INFORMATION: Synthetic peptide

<400> SEQUENCE: 31

Met Gly Leu Gly Leu His Leu Leu Val Leu Ala Ala Ala Leu Gln Gly
1               5                   10                  15

Ala Lys Ser Lys Arg Lys Val
            20

<210> SEQ ID NO 32
<211> LENGTH: 26
<212> TYPE: PRT
<213> ORGANISM: Artificial Sequence
<220> FEATURE:
<223> OTHER INFORMATION: Synthetic peptide

<400> SEQUENCE: 32

Ala Ala Val Ala Leu Leu Pro Ala Val Leu Leu Ala Leu Leu Ala Pro
1               5                   10                  15

Ala Ala Ala Asn Tyr Lys Lys Pro Lys Leu
            20                  25

<210> SEQ ID NO 33
<211> LENGTH: 28
<212> TYPE: PRT
<213> ORGANISM: Artificial Sequence
<220> FEATURE:
<223> OTHER INFORMATION: Synthetic peptide

```
<400> SEQUENCE: 33

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 34
<211> LENGTH: 24
<212> TYPE: PRT
<213> ORGANISM: Artificial Sequence
<220> FEATURE:
<223> OTHER INFORMATION: Synthetic peptide

<400> SEQUENCE: 34

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 35
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (24)..(24)
<223> OTHER INFORMATION: Xaa can be any naturally occurring amino acid

<400> SEQUENCE: 35

Asp Pro Lys Gly Asp Pro Lys Gly Val Thr Val Thr Val Thr Val Thr
1               5                   10                  15

Val Thr Gly Lys Gly Asp Pro Xaa Pro Asp
            20                  25

<210> SEQ ID NO 36
<211> LENGTH: 14
<212> TYPE: PRT
<213> ORGANISM: Artificial Sequence
<220> FEATURE:
<223> OTHER INFORMATION: Synthetic peptide

<400> SEQUENCE: 36

Pro Pro Pro Pro Pro Pro Pro Pro Pro Pro Pro Pro Pro Pro
1               5                   10

<210> SEQ ID NO 37
<211> LENGTH: 18
<212> TYPE: PRT
<213> ORGANISM: Artificial Sequence
<220> FEATURE:
<223> OTHER INFORMATION: Synthetic peptide

<400> SEQUENCE: 37

Val Arg Leu Pro Pro Pro Val Arg Leu Pro Pro Pro Val Arg Leu Pro
1               5                   10                  15

Pro Pro

<210> SEQ ID NO 38
<211> LENGTH: 10
<212> TYPE: PRT
<213> ORGANISM: Artificial Sequence
<220> FEATURE:
<223> OTHER INFORMATION: Synthetic peptide
```

```
<400> SEQUENCE: 38

Pro Arg Pro Leu Pro Pro Pro Arg Pro Gly
1               5                  10

<210> SEQ ID NO 39
<211> LENGTH: 30
<212> TYPE: PRT
<213> ORGANISM: Artificial Sequence
<220> FEATURE:
<223> OTHER INFORMATION: Synthetic peptide

<400> SEQUENCE: 39

Ser Val Arg Arg Arg Pro Arg Pro Pro Tyr Leu Pro Arg Pro Arg Pro
1               5                   10                  15

Pro Pro Phe Phe Pro Pro Arg Leu Pro Pro Arg Ile Pro Pro
            20                  25                  30

<210> SEQ ID NO 40
<211> LENGTH: 21
<212> TYPE: PRT
<213> ORGANISM: Artificial Sequence
<220> FEATURE:
<223> OTHER INFORMATION: Synthetic peptide

<400> SEQUENCE: 40

Thr Arg Ser Ser Arg Ala Gly Leu Gln Phe Pro Val Gly Arg Val His
1               5                   10                  15

Arg Leu Leu Arg Lys
            20

<210> SEQ ID NO 41
<211> LENGTH: 23
<212> TYPE: PRT
<213> ORGANISM: Artificial Sequence
<220> FEATURE:
<223> OTHER INFORMATION: Synthetic peptide

<400> SEQUENCE: 41

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 42
<211> LENGTH: 37
<212> TYPE: PRT
<213> ORGANISM: Artificial Sequence
<220> FEATURE:
<223> OTHER INFORMATION: Synthetic peptide

<400> SEQUENCE: 42

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Val Val Gly Gln Ala
            20                  25                  30

Thr Gln Ile Ala Lys
        35

<210> SEQ ID NO 43
<211> LENGTH: 28
<212> TYPE: PRT
<213> ORGANISM: Artificial Sequence
<220> FEATURE:
<223> OTHER INFORMATION: Synthetic peptide
```

-continued

```
<400> SEQUENCE: 43

Ala Leu Trp Met Thr Leu Leu Lys Lys Val Leu Lys Ala Ala Ala Lys
1               5                   10                  15

Ala Ala Leu Asn Ala Val Leu Val Gly Ala Asn Ala
            20                  25

<210> SEQ ID NO 44
<211> LENGTH: 26
<212> TYPE: PRT
<213> ORGANISM: Artificial Sequence
<220> FEATURE:
<223> OTHER INFORMATION: Synthetic peptide

<400> SEQUENCE: 44

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 45
<211> LENGTH: 14
<212> TYPE: PRT
<213> ORGANISM: Artificial Sequence
<220> FEATURE:
<223> OTHER INFORMATION: Synthetic peptide

<400> SEQUENCE: 45

Ile Asn Leu Lys Ala Leu Ala Ala Leu Ala Lys Lys Ile Leu
1               5                   10

<210> SEQ ID NO 46
<211> LENGTH: 33
<212> TYPE: PRT
<213> ORGANISM: Artificial Sequence
<220> FEATURE:
<223> OTHER INFORMATION: Synthetic peptide

<400> SEQUENCE: 46

Gly Phe Phe Ala Leu Ile Pro Lys Ile Ile Ser Ser Pro Leu Pro Lys
1               5                   10                  15

Thr Leu Leu Ser Ala Val Gly Ser Ala Leu Gly Gly Ser Gly Gly Gln
            20                  25                  30

Glu

<210> SEQ ID NO 47
<211> LENGTH: 15
<212> TYPE: PRT
<213> ORGANISM: Artificial Sequence
<220> FEATURE:
<223> OTHER INFORMATION: Synthetic peptide

<400> SEQUENCE: 47

Leu Ala Lys Trp Ala Leu Lys Gln Gly Phe Ala Lys Leu Lys Ser
1               5                   10                  15

<210> SEQ ID NO 48
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (23)..(23)
<223> OTHER INFORMATION: Xaa can be any naturally occurring amino acid
```

```
<400> SEQUENCE: 48

Ser Met Ala Gln Asp Ile Ile Ser Thr Ile Gly Asp Leu Val Lys Trp
1               5                   10                  15

Ile Ile Gln Thr Val Asn Xaa Phe Thr Lys Lys
            20                  25

<210> SEQ ID NO 49
<211> LENGTH: 41
<212> TYPE: PRT
<213> ORGANISM: Artificial Sequence
<220> FEATURE:
<223> OTHER INFORMATION: Synthetic peptide

<400> SEQUENCE: 49

Leu Leu Gly Asp Phe Phe Arg Lys Ser Lys Glu Lys Ile Gly Lys Glu
1               5                   10                  15

Phe Lys Arg Ile Val Gln Arg Ile Lys Gln Arg Ile Lys Asp Phe Leu
            20                  25                  30

Ala Asn Leu Val Pro Arg Thr Glu Ser
            35                  40

<210> SEQ ID NO 50
<211> LENGTH: 18
<212> TYPE: PRT
<213> ORGANISM: Artificial Sequence
<220> FEATURE:
<223> OTHER INFORMATION: Synthetic peptide

<400> SEQUENCE: 50

Pro Ala Trp Arg Lys Ala Phe Arg Trp Ala Trp Arg Met Leu Lys Lys
1               5                   10                  15

Ala Ala

<210> SEQ ID NO 51
<211> LENGTH: 18
<212> TYPE: PRT
<213> ORGANISM: Artificial Sequence
<220> FEATURE:
<223> OTHER INFORMATION: Synthetic peptide

<400> SEQUENCE: 51

Lys Leu Lys Leu Lys Leu Lys Leu Lys Leu Lys Leu Lys Leu Lys Leu
1               5                   10                  15

Lys Leu

<210> SEQ ID NO 52
<211> LENGTH: 4
<212> TYPE: PRT
<213> ORGANISM: Artificial Sequence
<220> FEATURE:
<223> OTHER INFORMATION: Synthetic peptide

<400> SEQUENCE: 52

Lys Lys Lys Lys
1

<210> SEQ ID NO 53
<211> LENGTH: 4
<212> TYPE: PRT
<213> ORGANISM: Artificial Sequence
<220> FEATURE:
```

<223> OTHER INFORMATION: Synthetic peptide

<400> SEQUENCE: 53

Arg Arg Arg Arg
1

<210> SEQ ID NO 54
<211> LENGTH: 4
<212> TYPE: PRT
<213> ORGANISM: Artificial Sequence
<220> FEATURE:
<223> OTHER INFORMATION: Synthetic peptide

<400> SEQUENCE: 54

Arg Lys Lys Lys
1

<210> SEQ ID NO 55
<211> LENGTH: 4
<212> TYPE: PRT
<213> ORGANISM: Artificial Sequence
<220> FEATURE:
<223> OTHER INFORMATION: Synthetic peptide

<400> SEQUENCE: 55

Arg Arg Lys Lys
1

<210> SEQ ID NO 56
<211> LENGTH: 4
<212> TYPE: PRT
<213> ORGANISM: Artificial Sequence
<220> FEATURE:
<223> OTHER INFORMATION: Synthetic peptide

<400> SEQUENCE: 56

Arg Arg Arg Lys
1

<210> SEQ ID NO 57
<211> LENGTH: 4
<212> TYPE: PRT
<213> ORGANISM: Artificial Sequence
<220> FEATURE:
<223> OTHER INFORMATION: Synthetic peptide

<400> SEQUENCE: 57

Lys Arg Arg Arg
1

<210> SEQ ID NO 58
<211> LENGTH: 4
<212> TYPE: PRT
<213> ORGANISM: Artificial Sequence
<220> FEATURE:
<223> OTHER INFORMATION: Synthetic peptide

<400> SEQUENCE: 58

Lys Lys Arg Arg
1

<210> SEQ ID NO 59
<211> LENGTH: 4
<212> TYPE: PRT

<213> ORGANISM: Artificial Sequence
<220> FEATURE:
<223> OTHER INFORMATION: Synthetic peptide

<400> SEQUENCE: 59

Lys Lys Lys Arg
1

<210> SEQ ID NO 60
<211> LENGTH: 4
<212> TYPE: PRT
<213> ORGANISM: Artificial Sequence
<220> FEATURE:
<223> OTHER INFORMATION: Synthetic peptide

<400> SEQUENCE: 60

Lys Arg Lys Arg
1

<210> SEQ ID NO 61
<211> LENGTH: 4
<212> TYPE: PRT
<213> ORGANISM: Artificial Sequence
<220> FEATURE:
<223> OTHER INFORMATION: Synthetic peptide

<400> SEQUENCE: 61

Arg Lys Arg Lys
1

<210> SEQ ID NO 62
<211> LENGTH: 4
<212> TYPE: PRT
<213> ORGANISM: Artificial Sequence
<220> FEATURE:
<223> OTHER INFORMATION: Synthetic peptide

<400> SEQUENCE: 62

Lys Arg Arg Lys
1

<210> SEQ ID NO 63
<211> LENGTH: 4
<212> TYPE: PRT
<213> ORGANISM: Artificial Sequence
<220> FEATURE:
<223> OTHER INFORMATION: Synthetic peptide

<400> SEQUENCE: 63

Arg Lys Lys Arg
1

<210> SEQ ID NO 64
<211> LENGTH: 4
<212> TYPE: PRT
<213> ORGANISM: Artificial Sequence
<220> FEATURE:
<223> OTHER INFORMATION: Synthetic peptide

<400> SEQUENCE: 64

Lys Arg Lys Lys
1

<210> SEQ ID NO 65
<211> LENGTH: 4
<212> TYPE: PRT
<213> ORGANISM: Artificial Sequence
<220> FEATURE:

<223> OTHER INFORMATION: Synthetic peptide

<400> SEQUENCE: 65

Lys Lys Arg Lys
1

<210> SEQ ID NO 66
<211> LENGTH: 4
<212> TYPE: PRT
<213> ORGANISM: Artificial Sequence
<220> FEATURE:
<223> OTHER INFORMATION: Synthetic peptide

<400> SEQUENCE: 66

Arg Lys Arg Arg
1

<210> SEQ ID NO 67
<211> LENGTH: 4
<212> TYPE: PRT
<213> ORGANISM: Artificial Sequence
<220> FEATURE:
<223> OTHER INFORMATION: Synthetic peptide

<400> SEQUENCE: 67

Arg Arg Lys Arg
1

<210> SEQ ID NO 68
<211> LENGTH: 10
<212> TYPE: PRT
<213> ORGANISM: Artificial Sequence
<220> FEATURE:
<223> OTHER INFORMATION: Synthetic peptide

<400> SEQUENCE: 68

Arg Arg Arg Cys Gln Cys Arg Arg Asn Lys
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Synthetic peptide

<400> SEQUENCE: 69

Cys Gln Cys Arg Arg Asn Lys Arg Arg Arg
1               5                   10

<210> SEQ ID NO 70
<211> LENGTH: 10
<212> TYPE: PRT
<213> ORGANISM: Artificial Sequence
<220> FEATURE:
<223> OTHER INFORMATION: Synthetic peptide

<400> SEQUENCE: 70

Arg Cys Gln Cys Arg Arg Asn Lys Arg Arg
1               5                   10

<210> SEQ ID NO 71
<211> LENGTH: 10
<212> TYPE: PRT
<213> ORGANISM: Artificial Sequence
<220> FEATURE:
<223> OTHER INFORMATION: Synthetic peptide

```
<400> SEQUENCE: 71

Arg Arg Cys Gln Cys Arg Arg Asn Lys Arg
1               5                   10

<210> SEQ ID NO 72
<211> LENGTH: 11
<212> TYPE: PRT
<213> ORGANISM: Artificial Sequence
<220> FEATURE:
<223> OTHER INFORMATION: Synthetic peptide

<400> SEQUENCE: 72

Arg Arg Cys Gln Cys Arg Arg Asn Lys Arg Arg
1               5                   10

<210> SEQ ID NO 73
<211> LENGTH: 11
<212> TYPE: PRT
<213> ORGANISM: Artificial Sequence
<220> FEATURE:
<223> OTHER INFORMATION: Synthetic peptide

<400> SEQUENCE: 73

Arg Arg Arg Arg Cys Gln Cys Arg Arg Asn Lys
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Synthetic peptide

<400> SEQUENCE: 74

Cys Gln Cys Arg Arg Asn Lys Arg Arg Arg Arg
1               5                   10

<210> SEQ ID NO 75
<211> LENGTH: 11
<212> TYPE: PRT
<213> ORGANISM: Artificial Sequence
<220> FEATURE:
<223> OTHER INFORMATION: Synthetic peptide

<400> SEQUENCE: 75

Arg Cys Gln Cys Arg Arg Asn Lys Arg Arg Arg
1               5                   10

<210> SEQ ID NO 76
<211> LENGTH: 11
<212> TYPE: PRT
<213> ORGANISM: Artificial Sequence
<220> FEATURE:
<223> OTHER INFORMATION: Synthetic peptide

<400> SEQUENCE: 76

Arg Arg Arg Cys Gln Cys Arg Arg Asn Lys Arg
1               5                   10

<210> SEQ ID NO 77
<211> LENGTH: 12
<212> TYPE: PRT
<213> ORGANISM: Artificial Sequence
<220> FEATURE:
<223> OTHER INFORMATION: Synthetic peptide
```

<400> SEQUENCE: 77

Arg Arg Arg Arg Arg Cys Gln Cys Arg Arg Asn Lys
1               5                   10

<210> SEQ ID NO 78
<211> LENGTH: 12
<212> TYPE: PRT
<213> ORGANISM: Artificial Sequence
<220> FEATURE:
<223> OTHER INFORMATION: Synthetic peptide

<400> SEQUENCE: 78

Cys Gln Cys Arg Arg Asn Lys Arg Arg Arg Arg Arg
1               5                   10

<210> SEQ ID NO 79
<211> LENGTH: 12
<212> TYPE: PRT
<213> ORGANISM: Artificial Sequence
<220> FEATURE:
<223> OTHER INFORMATION: Synthetic peptide

<400> SEQUENCE: 79

Arg Cys Gln Cys Arg Arg Asn Lys Arg Arg Arg Arg
1               5                   10

<210> SEQ ID NO 80
<211> LENGTH: 12
<212> TYPE: PRT
<213> ORGANISM: Artificial Sequence
<220> FEATURE:
<223> OTHER INFORMATION: Synthetic peptide

<400> SEQUENCE: 80

Arg Arg Arg Arg Cys Gln Cys Arg Arg Asn Lys Arg
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Synthetic peptide

<400> SEQUENCE: 81

Arg Arg Cys Gln Cys Arg Arg Asn Lys Arg Arg Arg
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Synthetic peptide

<400> SEQUENCE: 82

Arg Arg Arg Cys Gln Cys Arg Arg Asn Lys Arg Arg
1               5                   10

<210> SEQ ID NO 83
<211> LENGTH: 7
<212> TYPE: PRT
<213> ORGANISM: Artificial Sequence
<220> FEATURE:
<223> OTHER INFORMATION: Synthetic peptide

<400> SEQUENCE: 83

```
Cys Gln Cys Arg Arg Asn Lys
1               5

<210> SEQ ID NO 84
<211> LENGTH: 69
<212> TYPE: PRT
<213> ORGANISM: Artificial Sequence
<220> FEATURE:
<223> OTHER INFORMATION: Synthetic peptide

<400> SEQUENCE: 84

Cys Gln Cys Arg Arg Lys Asn Tyr Gly Gln Leu Asp Ile Phe Pro Ala
1               5                   10                  15

Arg Asp Thr Tyr His Pro Met Ser Glu Tyr Pro Thr Tyr His Thr His
            20                  25                  30

Gly Arg Tyr Val Pro Pro Ser Ser Thr Asp Arg Ser Pro Tyr Glu Lys
        35                  40                  45

Val Ser Ala Gly Asn Gly Gly Ser Ser Leu Tyr Thr Asn Pro Ala Val
    50                  55                  60

Ala Ala Ala Ser Leu
65

<210> SEQ ID NO 85
<211> LENGTH: 15
<212> TYPE: PRT
<213> ORGANISM: Artificial Sequence
<220> FEATURE:
<223> OTHER INFORMATION: Synthetic peptide

<400> SEQUENCE: 85

Cys Gln Cys Arg Arg Lys Asn Tyr Gly Gln Leu Asp Ile Phe Pro
1               5                   10                  15

<210> SEQ ID NO 86
<211> LENGTH: 7
<212> TYPE: PRT
<213> ORGANISM: Artificial Sequence
<220> FEATURE:
<223> OTHER INFORMATION: Synthetic peptide

<400> SEQUENCE: 86

Cys Gln Cys Arg Arg Lys Asn
1               5

<210> SEQ ID NO 87
<211> LENGTH: 11
<212> TYPE: PRT
<213> ORGANISM: Artificial Sequence
<220> FEATURE:
<223> OTHER INFORMATION: Synthetic peptide

<400> SEQUENCE: 87

Arg Arg Arg Cys Gln Cys Arg Arg Lys Asn Arg
1               5                   10

<210> SEQ ID NO 88
<211> LENGTH: 10
<212> TYPE: PRT
<213> ORGANISM: Artificial Sequence
<220> FEATURE:
<223> OTHER INFORMATION: Synthetic peptide

<400> SEQUENCE: 88

Arg Arg Cys Gln Cys Arg Arg Lys Asn Arg
1               5                   10
```

```
<210> SEQ ID NO 89
<211> LENGTH: 9
<212> TYPE: PRT
<213> ORGANISM: Artificial Sequence
<220> FEATURE:
<223> OTHER INFORMATION: Synthetic peptide

<400> SEQUENCE: 89

Arg Arg Cys Gln Cys Arg Arg Lys Asn
1               5

<210> SEQ ID NO 90
<211> LENGTH: 7
<212> TYPE: PRT
<213> ORGANISM: Artificial Sequence
<220> FEATURE:
<223> OTHER INFORMATION: Synthetic peptide

<400> SEQUENCE: 90

Asn Lys Arg Arg Cys Gln Cys
1               5

<210> SEQ ID NO 91
<211> LENGTH: 6
<212> TYPE: PRT
<213> ORGANISM: Artificial Sequence
<220> FEATURE:
<223> OTHER INFORMATION: Synthetic peptide

<400> SEQUENCE: 91

Cys Gln Cys Arg Arg Lys
1               5

<210> SEQ ID NO 92
<211> LENGTH: 4
<212> TYPE: PRT
<213> ORGANISM: Artificial Sequence
<220> FEATURE:
<223> OTHER INFORMATION: Synthetic peptide

<400> SEQUENCE: 92

Cys Gln Cys Arg
1

<210> SEQ ID NO 93
<211> LENGTH: 15
<212> TYPE: PRT
<213> ORGANISM: Artificial Sequence
<220> FEATURE:
<223> OTHER INFORMATION: Synthetic peptide

<400> SEQUENCE: 93

Ala Gln Ala Arg Arg Lys Asn Tyr Gly Gln Leu Asp Ile Phe Pro
1               5                   10                  15

<210> SEQ ID NO 94
<211> LENGTH: 7
<212> TYPE: PRT
<213> ORGANISM: Artificial Sequence
<220> FEATURE:
<223> OTHER INFORMATION: Synthetic peptide

<400> SEQUENCE: 94

Ala Gln Ala Arg Arg Lys Asn
1               5
```

ANTAGONISTS OF MUC1

This application claims benefit of priority to U.S. Provisional Application 61/303,928, filed Feb. 12, 2010, the entire contents of which are hereby incorporated by reference.

BACKGROUND OF THE INVENTION

1. Field of the Invention

This invention relates to regulation of inflammatory signaling. In particular, MUC1 peptides having 3-4 heterologous Arginine residues have been shown to effectively penetrate cell membranes, and thus inhibit MUC1 oligomerization and MUC1-mediated inflammatory signaling.

2. Related Art

A. MUC1

Mucins are extensively β-glycosylated proteins that are predominantly expressed by epithelial cells. The secreted and membrane-bound mucins form a physical barrier that protects the apical borders of epithelial cells from damage induced by toxins, microorganisms and other forms of stress that occur at the interface with the external environment. The transmembrane mucin 1 (MUC1) can also signal to the interior of the cell through its cytoplasmic domain. MUC1 has no sequence similarity with other membrane-bound mucins, except for the presence of a sea urchin sperm protein-enterokinase-agrin (SEA) domain (Duraisamy et al., 2006). In that regard, MUC1 is translated as a single polypeptide and then undergoes autocleavage at the SEA domain Macao, 2006).

The transmembrane MUC1 C-terminal subunit (MUC1-C) functions as a receptor (Ramasamy et al., 2007) and contains a 72-amino acid cytoplasmic domain (MUC1-CD) that is sufficient for inducing transformation (Huang et al., 2005). The MUC1-C subunit is also targeted to the nucleus by a process dependent on its oligomerization (Leng et al., 2007). MUC1-CD functions as a substrate for phosphorylation by the epidermal growth factor receptor (Li et al. 2001), c-Src (Li et al., 2001), glycogen synthase kinase 3β (GSK3β) (Li et al., 1998) and c-Abl (Ahmad et al., 2006). MUC1-CD also stabilizes the Wnt effector, β-catenin, through a direct interaction and thereby contributes to transformation (Huang et al., 2005). Other studies have demonstrated that MUC1-CD interacts directly with IKKβ and IKKγ, and contributes to activation of the IKK complex (Ahmad et al., 2007). Significantly, constitutive activation of NF-κB p65 in human carcinoma cells is downregulated by silencing MUC1, indicating that MUC1-CD has a functional role in regulation of the NF-κB p65 pathway (Ahmad et al., 2007). These findings have also suggested that MUC1-CD function could be targeted with small molecules to disrupt NF-κB signaling in carcinoma cells.

B. Poly-Arginine Tails

Transdermal or transmucosal drug delivery is an attractive route of drug delivery for several reasons. However, the advantages of transdermal and transmucosal delivery have not led to many clinical applications because of the low permeability of epithelial membranes, the skin in particular, to drugs. The difficulties in delivering drugs across the skin result from the barrier property of skin. Skin is a structurally complex thick membrane that represents the body's border to the external hostile environment.

Compounds that move from the environment into and through intact skin must first penetrate the stratum corneum, the outermost layer of skin, which is compact and highly keratinized. The stratum corneum is composed of several layers of keratin-filled skin cells that are tightly bound together by a "glue" composed of cholesterol and fatty acids. The thickness of the stratum corneum varies depending upon body location. It is the presence of stratum corneum that results in the impermeability of the skin to pharmaceutical agents. The stratum corneum is formed naturally by cells migrating from the basal layer toward the skin surface where they are eventually sloughed off. As the cells progress toward the surface, they become progressively more dehydrated and keratinized. The penetration across the stratum corneum layer is generally the rate-limiting step of drug permeation across skin. See, e.g., Flynn, 1985.

After penetration through the stratum corneum layer, systemically acting drug molecules then must pass into and through the epidermis, the dermis, and finally through the capillary walls of the bloodstream. The epidermis, which lies under the stratum corneum, is composed of three layers. The outermost of these layers is the stratum granulosum, which lies adjacent to the stratum corneum, is composed of cells that are differentiated from basal cells and keratinocytes, which make up the underlying layers. Having acquired additional keratin and a more flattened shape. The cells of this layer of the epidermis, which contain granules that are composed largely of the protein filaggrin. This protein is believed to bind to the keratin filaments to form the keratin complex. The cells also synthesize lipids that function as a "cement" to hold the cells together. The epidermis, in particular the stratum granulosum, contains enzymes such as aminopeptidases.

The next-outermost layer of the epidermis is the stratum spinosum, the principal cells of which are keratinocytes, which are derived from basal cells that comprise the basal cell layer. Langerhans cells, which are also found in the stratum spinosum, are antigen-presenting cells and thus are involved in the mounting of an immune response against antigens that pass into the skin. The cells of this layer are generally involved in contact sensitivity dermatitis.

The innermost epidermal layer is the stratum basale, or basal cell layer, which consists of one cell layer of cuboidal cells that are attached by hemi-desmosomes to a thin basement membrane which separates the basal cell layer from the underlying dermis. The cells of the basal layer are relatively undifferentiated, proliferating cells that serve as a progenitor of the outer layers of the epidermis. The basal cell layer includes, in addition to the basal cells, melanocytes.

The dermis is found under the epidermis, which is separated from the dermis by a basement membrane that consists of interlocking rete ridges and dermal papillae. The dermis itself is composed of two layers, the papillary dermis and the reticular dermis. The dermis consists of fibroblasts, histiocytes, endothelial cells, perivascular macrophages and dendritic cells, mast cells, smooth muscle cells, and cells of peripheral nerves and their endorgan receptors. The dermis also includes fibrous materials such as collagen and reticulin, as well as a ground substance (principally glycosaminoglycans, including hyaluronic acid, chondroitin sulfate, and dermatan sulfate).

Transport of drugs and other molecules across the blood-brain barrier is also problematic. The brain capillaries that make up the blood-brain barrier are composed of endothelial cells that form tight junctions between themselves (Goldstein et al., 1986; Pardridge, 1986). The endothelial cells and the tight intercellular junctions that join the cells form a barrier against the passive movement of many molecules from the blood to the brain. The endothelial cells of the blood-brain barrier have few pinocytotic vesicles, which in other tissues can allow somewhat unselective transport across the capillary wall. Nor is the blood-brain barrier interrupted by continuous gaps or channels that run through the cells, thus allowing for unrestrained passage of drugs and other molecules.

U.S. Pat. No. 6,593,292 provides compositions and methods for enhancing delivery of drugs and other agents across epithelial tissues, including the skin, gastrointestinal tract, pulmonary epithelium, and the like. The compositions and methods are also useful for delivery across endothelial tissues, including the blood brain barrier. The compositions and methods employ a delivery enhancing transporter that has sufficient guanidino or amidino sidechain moieties to enhance delivery of a compound conjugated to the reagent across one or more layers of the tissue, compared to the non-conjugated compound. The delivery-enhancing polymers include, for example, poly-Arginine molecules that are between 6 and 25 residues in length.

SUMMARY OF THE INVENTION

Thus, in accordance with the present invention, there is provided a method of inhibiting a MUC1-positive cancer cell comprising contacting the cell with a MUC1 peptide of at least 4 consecutive MUC1 residues and no more than 20 consecutive MUC1 residues and comprising the sequence CQC, wherein (i) the amino-terminal cysteine of CQC is covered on its $NH_2$-terminus by at least one amino acid residue that need not correspond to the native MUC1 transmembrane sequence; and (ii) the peptide comprises 3-5 consecutive positively-charged amino acid residues in addition to those positively-charged amino acid residues corresponding to native MUC1 residues. The MUC1-positive cell may be a solid tumor cell, such as a lung cancer cell, a brain cancer cell, a head & neck cancer cell, a breast cancer cell, a skin cancer cell, a liver cancer cell, a pancreatic cancer cell, a stomach cancer cell, a colon cancer cell, a rectal cancer cell, a uterine cancer cell, a cervical cancer cell, an ovarian cancer cell, a testicular cancer cell, a skin cancer cell or a esophageal cancer cell. The MUC1-positive cell may be a leukemia or myeloma cell, such as acute myeloid leukemia, chronic myelogenous leukemia or multiple myeloma. The peptide may be a stapled peptide, a cyclized peptide, a peptidomimetic or peptoid. The method may further comprise contacting the cell with a second anti-cancer agent, such as where the second anti-cancer agent is contacted prior to the peptide, after the peptide or at the same time as the peptide. Inhibiting may comprise inhibiting cancer cell growth, cancer cell proliferation or inducing cancer cell death, such as by apoptosis.

The peptide may comprise at least 5, 6 or 7 consecutive MUC1 residues. The sequence may comprise CQCR (SEQ ID NO:1), CQCRR (SEQ ID NO:2), CQCRRR (SEQ ID NO:3), CQCRRRR (SEQ ID NO:4), CQCRRK (SEQ ID NO:5), or CQCRRKN (SEQ ID NO:6). The peptide may contain no more than 10 consecutive residues, 11 consecutive residues, 12 consecutive residues, 13 consecutive residues, 14 consecutive residues, 15 consecutive residues, 16 consecutive residues, 17 consecutive residues, 18 consecutive residues or 19 consecutive residues of MUC1. The 3-5 positively-charged residues may be located at the C-terminus of the peptide, may be located at the N-terminus of the peptide, or may be split between the N- and C-termini of the peptide. The peptide may comprise 1, 2, 3 or 4 positively-charged amino acid residues corresponding to native MUC1 residues. The 3-5 positively-charged amino acid residues may be arginine and/or lysine, and/or the positively-charged amino acid residues corresponding to native MUC1 residues may be arginine and/or lysine. The peptide may comprise all L amino acids, all D amino acids or a mix of L and D amino acids. The peptide may be encapsulated or embedded in a delivery vehicle, such as a liposome, a lysosome, a microcapsule or a nanoparticle. The peptide may be PEG-ylated.

In another embodiment, there is provided a method of inhibiting MUC1-positive cancer in a subject comprising administering to the subject a MUC1 peptide of at least 4 consecutive MUC1 residues and no more than 20 consecutive MUC1 residues and comprising the sequence CQC (SEQ ID NO:4), wherein (i) the amino-terminal cysteine of CQC is covered on its $NH_2$-terminus by at least one amino acid residue that need not correspond to the native MUC1 transmembrane sequence; and (ii) the peptide comprises 3-5 consecutive positively-charged amino acid residues in addition to those positively-charged amino acid residues corresponding to native MUC1 residues. Inhibiting may comprise inhibiting growth of a cancer cell, inhibiting proliferation of a cancer cell, inhibiting cancer cell metastasis or reducing tumor burden.

The peptide may comprise at least 5, 6 or 7 consecutive MUC1 residues, and/or may comprise CQCR, CQCRR, CQCRRR, CQCRRRR, CQCRRK, or CQCRRKN. The peptide may contain no more than 10 consecutive residues, 11 consecutive residues, 12 consecutive residues, 13 consecutive residues, 14 consecutive residues, 15 consecutive residues, 16 consecutive residues, 17 consecutive residues, 18 consecutive residues or 19 consecutive residues of MUC1. The 3-5 positively-charged amino acid residues may be located at the C-terminus of the peptide, may be located at the N-terminus of the peptide, or may be split between the N- and C-termini of the peptide. The peptide may comprise 1, 2, 3 or 4 positively-charged amino acids corresponding to native MUC1 residues. The 3-5 positively-charged amino acid residues are arginine and/or lysine, and/or the positively-charged amino acid residues corresponding to native MUC1 residues are arginine and/or lysine. The peptide may be a stapled peptide, a cyclized peptide, a peptidomimetic or peptoid. The peptide may be encapsulated or embedded in a delivery vehicle, such as a liposome, a lysosome, a microcapsule or a nanoparticle. The peptide may be PEG-ylated.

The cancer may be a solid tumor, such as lung cancer, brain cancer, head & neck cancer, breast cancer, skin cancer, liver cancer, pancreatic cancer, stomach cancer, colon cancer, rectal cancer, uterine cancer, cervical cancer, ovarian cancer, testicular cancer, skin cancer or esophageal cancer. The MUC1-positive cell may be a leukemia or myeloma cell, such as acute myeloid leukemia, chronic myelogenous leukemia or multiple myeloma. Administering may comprise intravenous, intra-arterial, oral, intratumoral, subcutaneous, topical or intraperitoneal administration, or may comprise local, regional, systemic, or continual administration. The method may further comprise administering to the subject a second cancer-cancer therapy. The second anti-cancer therapy may be administered prior to the peptide, after the peptide or at the same time as the peptide. The subject may be a human.

The peptide may be administered at 0.1-500 mg/kg/d. The may be administered at 10-100 mg/kg/d. The peptide may be administered daily, such as 7 days, 2 weeks, 3 weeks, 4 weeks, one month, 6 weeks, 8 weeks, two months, 12 weeks, or 3 months. The peptide may be administered weekly, such as for 2 weeks, 3 weeks, 4 weeks, 6 weeks, 8 weeks, 10 weeks, or 12 weeks. The peptide may comprise all L amino acids, all D amino acids, or a mix of L and D amino acids.

In addition, there is provided a method of inhibiting inflammatory signaling in a MUC1-expressing cell comprising contacting said cell with a MUC1 peptide of at least 4 consecutive MUC1 residues and no more than 20 consecutive MUC1 residues and comprising the sequence CQC, wherein (i) the amino-terminal cysteine of CQC is covered on its $NH_2$-terminus by at least one amino acid residue that need not correspond to the native MUC1 transmembrane sequence;

and (ii) the peptide comprises 3-5 consecutive positively-charged amino acid residues in addition to those positively-charged amino acid residues corresponding to native MUC1 residues. The peptide may comprise at least 5, 6 or 7 consecutive MUC1 residues, such as CQCR (SEQ ID NO:1), CQCRR (SEQ ID NO:2), CQCRRR (SEQ ID NO:3), CQCRRRR (SEQ ID NO:4), CQCRRK (SEQ ID NO:5), or CQCRRKN (SEQ ID NO:6). The MUC1-positive cell is a tumor cell, an endothelial cell or an inflammatory cell, such as a macrophage, a B cell, at T cell, a dendritic cell, a myeloid-derived suppressor cell, an NK cell or a neutrophil.

The peptide may contains no more than 10 consecutive residues, 11 consecutive residues, 12 consecutive residues, 13 consecutive residues, 14 consecutive residues, 15 consecutive residues, 16 consecutive residues, 17 consecutive residues, 18 consecutive residues or 19 consecutive residues of MUC1. The 3-5 positively-charged residues may be located at the C-terminus of said peptide, may be located at the N-terminus of said peptide, or may be split between the N- and C-termini of said peptide. The peptide may comprise 1, 2, 3 or 4 positively-charged amino acid residues corresponding to native MUC1 residues. The 3-5 positively-charged amino acid residues may be Arginine and/or Lysine, and/or the positively-charged amino acid residues corresponding to native MUC1 residues may be Arginine and/or Lysine. The peptide may comprise all L amino acids, all D amino acids, or a mix of L and D amino acids. The peptide may be a stapled peptide, a cyclized peptide, a peptidomimetic or peptoid. The peptide may be encapsulated or embedded in a delivery vehicle, such as a liposome, a lysosome, a microcapsule or a nanoparticle. The peptide may be PEG-ylated.

The method may further comprise contacting said cell with a second anti-inflammatory agent. The second anti-inflammatory agent may be contacted prior to said peptide, after said peptide, or at the same time as said peptide. The inflammatory signaling may comprise NF-κB-mediated signaling or STAT-mediated signaling, such as NF-κB-mediated inflammatory signaling comprising NF-κB activation of a target gene selected from the group consisting of Bcl-xL and MUC1, or STAT-mediated inflammatory signaling comprising STAT3 activation (e.g., STAT3 activation of a target gene selected from the group consisting of cyclin D1, survivin, Idp1, Idp2, Cdkn1C, Lefty1, Mest, Aes1, Zfp57, Zfp3611, Sh3bp1, Ccnd3 and MUC1).

In another embodiment, there is provided a method of inhibiting MUC1 binding to NF-κB or a STAT comprising in a MUC1-expressing cell comprising contacting said cell with a MUC1 peptide of at least 4 consecutive MUC1 residues and no more than 20 consecutive MUC1 residues and comprising the sequence CQC, wherein (i) the amino-terminal cysteine of CQC is covered on its $NH_2$-terminus by at least one amino acid residue that need not correspond to the native MUC1 transmembrane sequence; and (ii) the peptide comprises 3-5 consecutive positively-charged amino acid residues in addition to those positively-charged amino acid residues corresponding to native MUC1 residues. The peptide may be a stapled peptide, a cyclized peptide, a peptidomimetic or peptoid. The peptide may be encapsulated or embedded in a delivery vehicle, such as a liposome, a lysosome, a microcapsule or a nanoparticle. The peptide may be PEG-ylated.

In still another embodiment, there is provided a method of inhibiting MUC1 competition with IκBα for binding to NF-κB in a MUC1-expressing cell comprising contacting said cell with a MUC1 peptide of at least 4 consecutive MUC1 residues and no more than 20 consecutive MUC1 residues and comprising the sequence CQC, wherein (i) the amino-terminal cysteine of CQC is covered on its $NH_2$-terminus by at least one amino acid residue that need not correspond to the native MUC1 transmembrane sequence; and (ii) the peptide comprises 3-5 consecutive positively-charged amino acid residues in addition to those positively-charged amino acid residues corresponding to native MUC1 residues. The peptide may be a stapled peptide, a cyclized peptide, a peptidomimetic or peptoid. The peptide may be encapsulated or embedded in a delivery vehicle, such as a liposome, a lysosome, a microcapsule or a nanoparticle. The peptide may be PEG-ylated.

In a further embodiment, there is provided a method of inhibiting MUC1-induced nuclear translocation of NF-κB in a MUC1-expressing cell comprising contacting said cell with a MUC1 peptide of at least 4 consecutive MUC1 residues and no more than 20 consecutive MUC1 residues and comprising the sequence CQC, wherein (i) the amino-terminal cysteine of CQC is covered on its $NH_2$-terminus by at least one amino acid residue that need not correspond to the native MUC1 transmembrane sequence; and (ii) the peptide comprises 3-5 consecutive positively-charged amino acid residues in addition to those positively-charged amino acid residues corresponding to native MUC1 residues. The peptide may be a stapled peptide, a cyclized peptide, a peptidomimetic or peptoid. The peptide may be encapsulated or embedded in a delivery vehicle, such as a liposome, a lysosome, a microcapsule or a nanoparticle. The peptide may be PEG-ylated.

In still a further embodiment, there is provided a method of inhibiting an inflammatory response in a subject comprising administering to said subject a MUC1 peptide of at least 4 consecutive MUC1 residues and no more than 20 consecutive MUC1 residues and comprising the sequence CQC, wherein (i) the amino-terminal cysteine of CQC is covered on its $NH_2$-terminus by at least one amino acid residue that need not correspond to the native MUC1 transmembrane sequence; and (ii) the peptide comprises 3-5 consecutive positively-charged amino acid residues in addition to those positively-charged amino acid residues corresponding to native MUC1 residues. The peptide may comprise at least 5, 6 or 7 consecutive MUC1 residues, such as CQCR, CQCRR, CQCRRR, CQCRRRR, CQCRRK, or CQCRRKN. The peptide may contain no more than 10 consecutive residues, 11 consecutive residues, 12 consecutive residues, 13 consecutive residues, 14 consecutive residues, 15 consecutive residues, 16 consecutive residues, 17 consecutive residues, 18 consecutive residues or 19 consecutive residues of MUC1. The inflammatory response may be caused by NF-κB-mediated signaling or STAT-mediated signaling.

The 3-5 positively-charged amino acid residues may be located at the C-terminus of said peptide, may be located at the N-terminus of said peptide, or may be split between the N- and C-termini of said peptide. The peptide may comprise 1, 2, 3 or 4 positively-charged amino acid corresponding to native MUC1 residues. The 3-5 positively-charged amino acid residues may be arginine and/or lysine, and/or the positively-charged amino acid residues corresponding to native MUC1 residues may be arginine and/or lysine. The peptide may comprise all L amino acids, all D amino acids, or a mix of L and D amino acids. The peptide may be a stapled peptide, a cyclized peptide, a peptidomimetic or peptoid. The peptide may be encapsulated or embedded in a delivery vehicle, such as a liposome, a lysosome, a microcapsule or a nanoparticle. The peptide may be PEG-ylated.

Administering may comprise intravenous, intra-arterial, oral, intratumoral, subcutaneous, topical or intraperitoneal administration, and/or may comprise local, regional, systemic, or continual administration. Inhibiting may comprise inhibition or resolution of the inflammatory response. The method may further comprise administering to said subject a second anti-inflammatory therapy. The second anti-inflammatory therapy may be administered prior to said peptide, after said peptide or at the same time as said peptide.

The subject may be a human. The peptide may be administered at 0.1-500 mg/kg/d, or at 10-100 mg/kg/d. The peptide may be administered daily, such as for 7 days, 2 weeks, 3 weeks, 4 weeks, one month, 6 weeks, 8 weeks, two months, 12 weeks, or 3 months. Alternatively, the peptide may be administered weekly, such as for 2 weeks, 3 weeks, 4 weeks, 6 weeks, 8 weeks, 10 weeks, or 12 weeks.

In an additional embodiment, there is provided a pharmaceutical composition comprising (a) a MUC1 peptide of at least 4 consecutive MUC1 residues and no more than 20 consecutive MUC1 residues and comprising the sequence CQC:
  (i) the amino-terminal cysteine of CQC is covered on its NH$_2$-terminus by at least one amino acid residue that need not correspond to the native MUC1 transmembrane sequence;
  (ii) the peptide comprises 3-5 consecutive positively-charged amino acid residues in addition to those positively-charged amino acid residues corresponding to native MUC1 residues; and
(b) a second anti-inflammatory agent other than (a). The second anti-inflammatory agent may be a steroid or COX-2 inhibitor. The peptide may be a stapled peptide, a cyclized peptide, a peptidomimetic or peptoid. The peptide may be encapsulated or embedded in a delivery vehicle, such as a liposome, a lysosome, a microcapsule or a nanoparticle. The peptide may be PEG-ylated.

In still an additional embodiment, there is provided a pharmaceutical composition comprising (a) a MUC1 peptide of at least 4 consecutive MUC1 residues and no more than 20 consecutive MUC1 residues and comprising the sequence CQC, wherein:
  (i) the amino-terminal cysteine of CQC is covered on its NH$_2$-terminus by at least one amino acid residue that need not correspond to the native MUC1 transmembrane sequence;
  (ii) the peptide comprises 3-5 consecutive positively-charged amino acid residues in addition to those positively-charged amino acid residues corresponding to native MUC1 residues; and
(b) a pharmaceutically acceptable carrier, buffer or diluent. The peptide may be at least 5, 6, 7 or 8 consecutive MUC1 residues. The peptide may comprise no more than 10 consecutive residues, 11 consecutive residues, 12 consecutive residues, 13 consecutive residues, 14 consecutive residues, 15 consecutive residues, 16 consecutive residues, 17 consecutive residues, 18 consecutive residues or 19 consecutive residues of MUC1.

The said 3-5 positively-charged amino acid residues may be located at the C-terminus of said peptide, may be located at the N-terminus of said peptide, or may be split between the N- and C-termini of said peptide. The peptide may comprise 1, 2, 3 or 4 positively-charged amino acid resides corresponding to native MUC1 residues. The −5 positively-charged amino acid residues may be arginine and/or lysine, and/or the positively-charged amino acid residues corresponding to native MUC1 residues may be arginine and/or lysine. The peptide may be a stapled peptide, a cyclized peptide, a peptidomimetic or peptoid. The peptide may be encapsulated or embedded in a delivery vehicle, such as a liposome, a lysosome, a microcapsule or a nanoparticle. The peptide may be PEG-ylated.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

The following drawings form part of the present specification and are included to further demonstrate certain aspects of the present invention. The invention may be better understood by reference to one or more of these drawings in combination with the detailed.

FIG. 3—Sequences Of MUC1-CD Peptides (SEQ ID NOS. 84-94).

FIG. 10—MUC-1 CQC Peptoids.

DESCRIPTION OF ILLUSTRATIVE EMBODIMENTS

Figure 1:
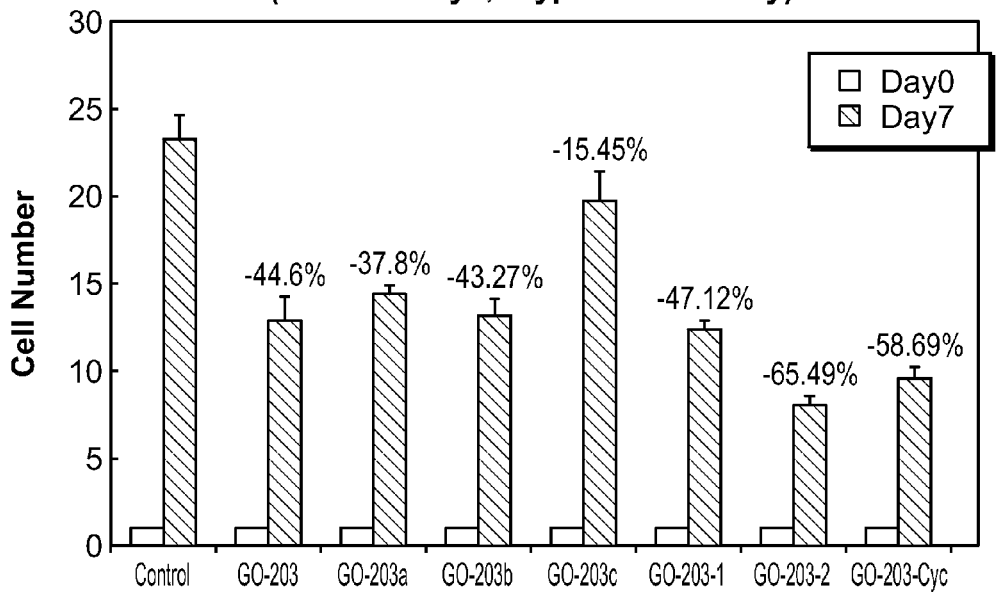
FIG. 1—Effect of CQC peptides on ZR-75-1 breast cancer cells. Graphic version of the peptide inhibition data from Table 1.

MUC1 has been studied extensively by the inventors and others for its role in cancer. As discussed above, human MUC1 is heterodimeric glycoprotein, translated as a single polypeptide and cleaved into N- and C-terminal subunits in the endoplasmic reticulum (Ligtenberg et al., 1992; Macao et al., 2006; Levitin et al., 2005). Aberrant overexpression of MUC1, as found in most human carcinomas (Kufe et al., 1984), confers anchorage-independent growth and tumorigenicity (Li et al., 2003a; Huang et al., 2003; Schroeder et al., 2004; Huang et al., 2005). Other studies have demonstrated that overexpression of MUC1 confers resistance to apoptosis induced by oxidative stress and genotoxic anti-cancer agents (Yin and Kufe, 2003; Ren et al., 2004; Raina et al., 2004; Yin et al., 2004; Raina et al., 2006; Yin et al., 2007).

The family of tethered and secreted mucins functions in providing a protective barrier of the epithelial cell surface. With damage to the epithelial layer, the tight junctions between neighboring cells are disrupted, and polarity is lost as the cells initiate a heregulin-induced repair program (Vermeer et al., 2003). MUC1-N is shed from the cell surface (Abe and Kufe, 1989), leaving MUC1-C to function as a transducer of environmental stress signals to the interior of the cell. In this regard, MUC1-C forms cell surface complexes with members of the ErbB receptor family, and MUC1-C is targeted to the nucleus in the response to heregulin stimulation (Li et al., 2001; Li et al., 2003c). MUC1-C also functions in integrating the ErbB receptor and Wnt signaling pathways through direct interactions between the MUC1 cytoplasmic domain (CD) and members of the catenin family (Huang et al., 2005; Li et al., 2003c; Yamamoto et al., 1997; Li et al., 1998; Li et al., 2001; Li and Kufe, 2001). Other studies have demonstrated that MUC1-CD is phosphorylated by glycogen synthase kinase 3β, c-Src, protein kinase Cδ, and c-Abl (Raina et al., 2006; Li et al., 1998; Li et al., 2001; Ren et al., 2002).

The mechanisms responsible for nuclear targeting of MUC1-C are unclear. Proteins containing a classical nuclear localization signal (NLS) are imported into the nucleus by first binding to importin α and then, in turn, importin β (Weis, 2003). The cargo-importin α/β complex docks to the nuclear pore by binding to nucleoporins and is transported through the pore by a mechanism dependent on the Ran GTPase. Classical NLSs are monopartite with a single cluster of 4-5 basic amino acids or bipartite with two clusters of basic amino acids separated by a linker of 10-12 amino acids. MUC1-CD contains a RRK motif that does not conform to a prototypical monopartite NLS (Hodel et al., 2002). However, certain proteins containing non-classical NLSs are transported through the nuclear pore by binding directly to importin β (Kau et al., 2004). Importin β associates with several nucleoporins (Ryan and Wente, 2000), including Nup62, which is located on both the cytoplasmic and nucleoplasmic faces of nuclear pore complexes (Percipalle et al., 1997). Other studies have indicated that β-catenin is imported into the nucleus by an importin- and nucleoporin-independent mechanism (Suh and Gumbiner, 2003).

In 2006, the inventors reported that MUC1 is imported into the nucleus by a mechanism involving binding to Nup62 (Leng et al., 2007). They also demonstrate that MUC1 forms oligomers through a CQC motif in the MUC1 cytoplasmic domain and that MUC1 oligomerization is necessary for nuclear import. In 2007, they also demonstrated that overexpression of MUC1 in human carcinoma cells is associated with constitutive activation of NF-kappaB p65 (Ahmad et al. 2007). MUC1 was shown to interact with the high-molecular-weight IκB kinase (IKK) complex in vivo, and that the MUC1 cytoplasmic domain binds directly to IKKβ and IKKγ. Interaction of MUC1 with both IKKβ and IKKγ is necessary for IKKβ activation, resulting in phosphorylation and degradation of IκBα. These findings indicated that MUC1 is important for physiological activation of IKKβ and that overexpression of MUC1, as found in human cancers, confers sustained induction of the IKKβ-NF-κB p65 pathway.

In additional unpublished work, the inventors have extended their research to encompass a further elucidation of the role that the CQC motif plays in oligomer formation. They also have demonstrated that short peptides corresponding to this region are able to disrupt MUC1 oligomer formation, preventing transport into the nucleus of tumor cells. These peptides are able to inhibit tumor cell growth, as well as induce apoptosis in such cells and even necrosis of tumor tissue.

The inventors have also examined the emerging role for MUC1 in inflammatory disease states, seeking to determine whether the same peptides would find use in treating inflammatory disorders. Studies described in U.S. Provisional Patent Application 61/253,730 demonstrate that MUC1-CD binds directly to NF-κB p65 and blocks the interaction between NF-κB p65 and IκBα. The inventors also showed that the MUC1-C subunit associates with NF-κB p65 on the promoters of NF-κB target genes and promotes NF-κB-mediated transcription. These results also demonstrated that an inhibitor of MUC1-C oligomerization blocks the MUC1 interaction with NF-κB p65 and constitutive activation of the inflammatory NF-κB pathway. In addition, a similar interaction with STAT3, another inflammatory signaling factor, was demonstrated, even further implicating MUC1 in this process.

Here, the inventors report the finding that poly-Arg tails, used to improve transport of MUC1 peptides into cells, can be shorter than previously thought. While the reason behind this finding is not clear, it may be the fact that other positively-charged residues at or near the termini of the MUC1 peptides being used compensate for the reduced number of arginines in the added tails. In addition, variations including peptoid, peptidomimetics, stapled peptides and cyclic peptides also are described. These and other aspects of the invention are described in detail below.

I. MUC1

A. Structure

MUC1 is a mucin-type glycoprotein that is expressed on the apical borders of normal secretory epithelial cells (Kufe et al., 1984). MUC1 forms a heterodimer following synthesis as a single polypeptide and cleavage of the precursor into two subunits in the endoplasmic reticulum (Ligtenberg et al., 1992). The cleavage may be mediated by an autocatalytic process (Levitan et al., 2005). The >250 kDa MUC1 N-terminal (MUC1 N-ter, MUC1-N) subunit contains variable numbers of 20 amino acid tandem repeats that are imperfect with highly conserved variations and are modified by O-linked glycans (Gendler et al., 1988; Siddiqui et al., 1988). MUC1-N is tethered to the cell surface by dimerization with the ~23 kDa C-terminal subunit (MUC1 C-ter, MUC1-C), which includes a 58 amino acid extracellular region, a 28 amino acid transmembrane domain and a 72 amino acid cytoplasmic domain (CD) (Merlo et al., 1989). The human MUC1 sequence is shown below:

(SEQ ID NO: 7)
GSVVVQLTLAFREGTINVHDVETQFNQYKTEAASRYNLTISDVSVSDVP

FPFSAQSGAGVPGWGIALLVLVCVLVALAIVYLIALAVCQCRRKNYGQL

DIFPARDTYHPMSEYPTYHTHGRYVPPSSTDRSPYEKVSAGNGGSSLSY

TNPAVAATSANL

The bold sequence indicates the CD, and the underlined portion is an oligomer-inhibiting peptide. With transformation of normal epithelia to carcinomas, MUC1 is aberrantly overexpressed in the cytosol and over the entire cell membrane (Kufe et al., 1984; Perey et al., 1992). Cell membrane-associated MUC1 is targeted to endosomes by clathrin-mediated endocytosis (Kinlough et al., 2004). In addition, MUC1-C, but not MUC1-N, is targeted to the nucleus (Baldus et al., 2004; Huang et al., 2003; Li et al., 2003a; Li et al., 2003b; Li et al., 2003c; Wei et al., 2005; Wen et al., 2003) and mitochondria (Ren et al., 2004).

B. Function

MUC1 interacts with members of the ErbB receptor family (Li et al., 2001b; Li et al., 2003c; Schroeder et al., 2001) and with the Wnt effector, β-catenin (Yamamoto et al., 1997). The epidermal growth factor receptor and c-Src phosphorylate the MUC1 cytoplasmic domain (MUC1-CD) on Y-46 and thereby increase binding of MUC1 and β-catenin (Li et al., 2001a; Li et al., 2001b). Binding of MUC1 and β-catenin is also regulated by glycogen synthase kinase 3β and protein kinase Cδ (Li et al., 1998; Ren et al., 2002). MUC1 colocalizes with β-catenin in the nucleus (Baldus et al., 2004; Li et al., 2003a; Li et al., 2003c; Wen et al., 2003) and coactivates transcription of Wnt target genes (Huang et al., 2003). Other studies have shown that MUC1 also binds directly to p53 and regulates transcription of p53 target genes (Wei et al., 2005). Notably, overexpression of MUC1 is sufficient to induce anchorage-independent growth and tumorigenicity (Huang et al., 2003; Li et al., 2003b; Ren et al., 2002; Schroeder et al., 2004).

Most mitochondrial proteins are encoded in the nucleus and are imported into mitochondria by translocation complexes in the outer and inner mitochondrial membranes. Certain mitochondrial proteins contain N-terminal mitochondrial targeting sequences and interact with Tom20 in the outer mitochondrial membrane (Truscott et al., 2003). Other mitochondrial proteins contain internal targeting sequences and interact with the Tom70 receptor (Truscott et al., 2003). Recent work showed that mitochondrial proteins without internal targeting sequences are delivered to Tom70 by a complex of HSP70 and HSP90 (Young et al., 2003).

II. MUC1 Peptides

A. Structure

The present invention contemplates the design, production and use of various MUC1 peptides. The structural features of these peptides are as follows. First, the peptides have no more than 20 consecutive residues of MUC1. Thus, the term "a peptide having no more than 20 consecutive residues," even when including the term "comprising," cannot be understood to comprise a greater number of consecutive MUC1 residues. Second, the peptides will contain the CQC motif, and may further comprise the CQCR, CQCRR, or CQCRRK motifs. Thus, the peptides will have, at a minimum, these four, five or six consecutive residues of the MUC1-C domain. Third, the peptides will have at least one amino acid residue attached to the $NH_2$-terminal side of the first C residue in the CQCRRK motif, such that the first C residue is "covered" by that at least one amino acid attached thereto. This residue may be native to MUC1 (i.e., from the transmembrane domain), may be selected at random (any of the twenty naturally-occurring amino acids or analogs thereof), or may be part of another peptide sequence (e.g., a tag sequence for purification, a stabilizing sequence, or a cell delivery domain).

In general, the peptides will be 50 residues or less, again, comprising no more than 20 consecutive residues of MUC1. The overall length may be 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 residues. Ranges of peptide length of 4-50 residues, 7-50 residues, 4-25 residues 7-25, residues, 4-20 residues, 7-20 residues, and 3-15 residues, and 7-15 residues are contemplated. The number of consecutive MUC1 residues may be 3, 4, 5, 6, 7, 8, 9, 10, 11, 12, 13, 14, 15, 16, 17, 18, 19 or 20. Ranges of consecutive residues of 4-20 residues, 5-20 residues, 6-20 residues, 7-20 residues, 4-15 residues, 5-15 residues, 6-15 residues and 7-15 residues are contemplated.

The present invention may utilize L-configuration amino acids, D-configuration amino acids, or a mixture thereof. While L-amino acids represent the vast majority of amino acids found in proteins, D-amino acids are found in some proteins produced by exotic sea-dwelling organisms, such as cone snails. They are also abundant components of the peptidoglycan cell walls of bacteria. D-serine may act as a neurotransmitter in the brain. The L and D convention for amino acid configuration refers not to the optical activity of the amino acid itself, but rather to the optical activity of the isomer of glyceraldehyde from which that amino acid can theoretically be synthesized (D-glyceraldehyde is dextrorotary; L-glyceraldehyde is levorotary).

One form of an "all-D" peptide is a retro-inverso peptide. Retro-inverso modification of naturally occurring polypeptides involves the synthetic assemblage of amino acids with α-carbon stereochemistry opposite to that of the corresponding L-amino acids, i.e., D-amino acids in reverse order with respect to the native peptide sequence. A retro-inverso analogue thus has reversed termini and reversed direction of peptide bonds (NH—CO rather than CO—NH) while approximately maintaining the topology of the side chains as in the native peptide sequence. See U.S. Pat. No. 6,261,569, incorporated herein by reference.

As mentioned above, peptides modified for in vivo use by the addition, at the amino- and/or carboxyl-terminal ends, of a blocking agent to facilitate survival of the peptide in vivo are contemplated. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. These agents can be added either chemically during the synthesis of the peptide, or by recombinant DNA technology by methods familiar in the art. Alternatively, blocking agents such as pyroglutamic acid or other molecules known in the art can be attached to the amino and/or carboxyl terminal residues.

B. Cell Penetrating Domains

The present invention contemplates the use of a cell delivery domain (also called a cell delivery vector, or cell transduction domain) linked to MUC1 peptides. Such domains have been described in the art and are generally characterized as short amphipathic or cationic peptides and peptide derivatives, often containing multiple lysine and arginine resides (Fischer, 2007). Other examples are shown in Table 1, below.

TABLE

| CDD/CTD PEPTIDES | SEQ ID NO: |
|---|---|
| GALFLGWLGAAGSTMGAKKKRKV | 8 |
| RQIKIWFQNRRMKWKK | 9 |
| RRMKWKK | 10 |
| RRWRRWWRRWWRRWRR | 11 |
| RGGRLSYSRRRFSTSTGR | 12 |
| YGRKKRRQRRR | 13 |
| RKKRRQRRR | 14 |
| YARAAARQARA | 15 |
| RRRRRRRR | 16 |
| KKKKKKKK | 17 |
| GWTLNSAGYLLGKINLKALAALAKXIL | 18 |
| LLILLRRRIRKQANAHSK | 19 |
| SRRHHCRSKAKRSRHH | 20 |
| NRARRNRRRVR | 21 |
| RQLRIAGRRLRGRSR | 22 |
| KLIKGRTPIKFGK | 23 |
| RRIPNRRPRR | 24 |
| KLALKLALKALKAALKLA | 25 |
| KLAKLAKKLAKLAK | 26 |
| GALFLGFLGAAGSTNGAWSQPKKKRKV | 27 |
| KETWWETWWTEWSQPKKKRKV | 28 |
| LKKLLKKLLKKLLKKLLKKL | |

TABLE-continued

| CDD/CTD PEPTIDES | SEQ ID NO: |
|---|---|
| QAATATRGRSAASRPTERPRAPARSASRPRRPVE | 30 |
| MGLGLHLLVLAAALQGAKSKRKV | 31 |
| AAVALLPAVLLALLAPAAANYKKPKL | 32 |
| MANLGYWLLALFVTMWTDVGLCKKRPKP | 33 |
| LGTYTQDFNKFHTFPQTAIGVGAP | 34 |
| DPKGDPKGVTVTVTVTVTGKGDPXPD | 35 |
| PPPPPPPPPPPPPPP | 36 |
| VRLPPPVRLPPPVRLPPP | 37 |
| PRPLPPPRPG | 38 |
| SVRRRPRPPYLPRPRPPPFFPPRLPPRIPP | 39 |
| TRSSRAGLQFPVGRVHRLLRK | 40 |
| GIGKFLHSAKKFGKAFVGEIMNS | 41 |
| KWKLFKKIEKVGQNIRDGIIKAGPAVAVVGQATQIAK | 42 |
| ALWMTLLKKVLKAAAKAALNAVLVGANA | 43 |
| GIGAVLKVLTTGLPALISWIKRKRQQ | 44 |
| INLKALAALAKKIL | 45 |
| GFFALIPKIISSPLPKTLLSAVGSALGGSGGQE | 46 |
| LAKWALKQGFAKLKS | 47 |
| SMAQDIISTIGDLVKWIIQTVNXFTKK | 48 |
| LLGDFFRKSKEKIGKEFKRIVQRIKQRIKDFLANLVPRTES | 49 |
| PAWRKAFRWAWRMLKKAA | 50 |
| KLKLKLKLKLKLKLKLKL | 51 |

However, the present inventors have determined that such extended tail sequences are not required for delivery of MUC1 peptides. Rather, using as few as three or four Arginine residues, or optionally other positively-charged residues such as Lysine or Histidine, it is possible to achieve effective cell penetration of MUC1 peptides. Thus, combinations such as the following would be of particular interest here:

KKK   KKKK   RRR   RRRR   KRR   KKR
      (SEQ ID NO: 52)   (SEQ ID NO: 53)

RKK   RRK   RKKK   RRKK   RRRK   KRRR
            (SEQ ID NO: 54)(SEQ ID NO: 55)(SEQ ID NO: 56)(SEQ ID NO: 57)

KKRR   KKKR   KRKR   RKRK   KRRK   RKKR
(SEQ ID NO: 58)(SEQ ID NO: 59)(SEQ ID NO: 60)(SEQ ID NO: 61)(SEQ ID NO:62) ID NO:63)

RKR   KRK   KRKK   KKRK   RKRR   RRKR
            (SEQ ID NO: 64)(SEQ ID NO: 65)(SEQ ID NO: 66)(SEQ ID NO: 67)

Though it is not known for certain, the presence of "native" postively-charged residues in the proximity of the peptide terminus, i.e., in proximity to the tail, may provide an important function in replacing the missing positively-charged residues in the shortened tail segment. These native residues may include Arginine, Lysine, Histidine and combinations thereof. Of particular interest are two Arginines and one Lysine (RRK) in the native MUC1 sequence and adjacent to the CQC motif.

In addition, the included 3-5 positively charged residues may not be contiguous, but instead may be split between the N- and C-termini. For example, where X is a non-MUC1 positively-charged residue, the location may be as follows:

| XXX-peptide-X | XX-peptide-XX | X-peptide-XXX |
| XX-peptide-X | X-peptide-XX | XXX-peptide |
| peptide-XXX | XXXX-peptide | peptide-XXXX |
| XXXX-peptide-X | XXX-peptide-XX | XX-peptide-XXX |
| XXXXX-peptide | X-peptide-XXXX | peptide-XXXXX |

So, for the peptide CQCRRNK (SEQ ID NO:83), and using all Arginine residues, exemplary peptides include:

| RRR-CQCRRNK | CQCRRNK-RRR | R-CQCRRNK-RR |
| (SEQ ID NO: 68) | (SEQ ID NO: 69) | (SEQ ID NO: 70) |
| RR-CQCRRNK-R | RR-CQCRRNK-RR | RRRR-CQCRRNK |
| (SEQ ID NO: 71) | (SEQ ID NO: 72) | (SEQ ID NO: 73) |
| CQCRRNK-RRRR | R-CQCRRNK-RRR | RRR-CQCRRNK-R |
| (SEQ ID NO: 74) | (SEQ ID NO: 75) | (SEQ ID NO: 76) |
| RRRRR-CQCRRNK | CQCRRNK-RRRRR | R-CQCRRNK-RRRR |
| (SEQ ID NO: 77) | (SEQ ID NO: 78) | (SEQ ID NO: 79) |
| RRRR-CQCRRNK-R | RR-CQCRRNK-RRR | RRR-CQCRRNK-RR |
| (SEQ ID NO: 80) | (SEQ ID NO: 81) | (SEQ ID NO: 82) |

C. Synthesis

It will be advantageous to produce peptides using the solid-phase synthetic techniques (Merrifield, 1963). Other peptide synthesis techniques are well known to those of skill in the art (Bodanszky et al., 1976; Peptide Synthesis, 1985; Solid Phase Peptide Synthelia, 1984). Appropriate protective groups for use in such syntheses will be found in the above texts, as well as in Protective Groups in Organic Chemistry, 1973. These synthetic methods involve the sequential addition of one or more amino acid residues or suitable protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, such as lysine.

Using solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptides of the invention are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

Aside from the twenty standard amino acids can be used, there are a vast number of "non-standard" amino acids. Two of these can be specified by the genetic code, but are rather rare in proteins. Selenocysteine is incorporated into some proteins at a UGA codon, which is normally a stop codon. Pyrrolysine is used by some methanogenic archaea in enzymes that they use to produce methane. It is coded for with the codon UAG. Examples of non-standard amino acids that are not found in proteins include lanthionine, 2-aminoisobutyric acid, dehydroalanine and the neurotransmitter gamma-aminobutyric acid. Non-standard amino acids often occur as intermediates in the metabolic pathways for standard amino acids—for example ornithine and citrulline occur in the urea cycle, part of amino acid catabolism. Non-standard amino acids are usually formed through modifications to standard amino acids. For example, homocysteine is formed through the transsulfuration pathway or by the demethylation of methionine via the intermediate metabolite S-adenosyl methionine, while hydroxyproline is made by a posttranslational modification of proline.

D. Linkers

Linkers or cross-linking agents may be used to fuse MUC1 peptides to other proteinaceous sequences. Bifunctional cross-linking reagents have been extensively used for a variety of purposes including preparation of affinity matrices, modification and stabilization of diverse structures, identification of ligand and receptor binding sites, and structural studies. Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino-, sulfhydryl-, guanidino-, indole-, or carboxyl-specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

In another example, heterobifunctional cross-linking reagents and methods of using the cross-linking reagents are described in U.S. Pat. No. 5,889,155, specifically incorporated herein by reference in its entirety. The cross-linking reagents combine a nucleophilic hydrazide residue with an electrophilic maleimide residue, allowing coupling in one example, of aldehydes to free thiols. The cross-linking reagent can be modified to cross-link various functional groups and is thus useful for cross-linking polypeptides. In instances where a particular peptide does not contain a residue amenable for a given cross-linking reagent in its native sequence, conservative genetic or synthetic amino acid changes in the primary sequence can be utilized.

Another use of linkers in the context of peptides as therapeutics is the so-called "Stapled Peptide" technology of Aileron Therapeutics. The general approach for "stapling" a peptide is that two key residues within the peptide are modified by attachment of linkers through the amino acid side chains. Once synthesized, the linkers are connected through a catalyst, thereby creating a bridge the physically constrains the peptide into its native α-helical shape. In addition to helping retain the native structure needed to interact with a target molecule, this conformation also provides stability against peptidases as well as cell-permeating properties. U.S. Pat. Nos. 7,192,713 and 7,183,059, describing this technology, are hereby incorporated by reference. See also Schafmeister et al. (2000). Particular stapled peptides (R8, B5 and S5 are stapling bridges) are shown below.

Oligomerized MUC1 is an oncoprotein involved in the transformation and metastasis of tumor cells (Raina et al., 2009; Joshi et al., 2009; Yin et al., 2010). To impart resistance to protease degradation, GO-203-2c was designed as a D-amino acid with amidated C-terminal and acetylated N-terminal (Dintzis et al., 1993, Guichard et al., 1994, Hamamoto et al., 2002). In addition, a polyarginine sequence was included at the N-terminal to enhance cell penetration (Jones et al., 2005).

```
Ac-Arg-Arg-Arg-Arg-Arg-R8-Cys-Gln-Cys-Arg-Arg-Lys-S5-Tyr-NH₂(R8&S5 bridge)
Ac-Ala-Lys-Lys-Tyr-Leu-S5-Ala-Leu-Ala-B5-Cys-Gln-Cys-S5-Arg-Arg-Lys-Asn-NH₂
Ac-Arg-Arg-Arg-Arg-Arg-R8-Cys-Arg-Cys-Arg-Arg-Lys-S5-Tyr-NH2
Ac-Arg-Arg-Arg-Arg-Arg-R8-Cys-Arg-Cys-Arg-Arg-Lys-S5-NH2
Ac-Arg-Arg-Arg-Arg-Arg-R8-Cys-Arg-Cys-Arg-Arg-Lys-S5-Arg-NH2
Ac-Arg-Arg-R8-Arg-Arg-Arg-Cys-Gln-Cys-S5-Arg-Lys-NH2
Ac-Arg-Arg-R8-Arg-Arg-Arg-Cys-Arg-Cys-S5-Arg-Lys-NH2
Ac-Ala-Lys-Lys-Tyr-Leu-S5-Ala-Leu-Ala-B5-Cys-Gln-Cys-S5-Arg-Lys-Asn-Tyr-NH₂
Ac-Ile-Val-Try-S5-Ile-Ala-Leu-S5-Val-Cys-Gln-Cys-Arg-Arg-Lys-Asn-Tyr-NH₂
Ac-Arg-Arg-Arg-Arg-Arg-R8-Cys-Gln-Cys-Arg-Arg-Lys-S5-NH₂
Ac-Arg-Arg-Arg-Arg-Arg-R8-Cys-Gln-Cys-Arg-Arg-Lys-S5-Gly-NH₂
Ac-Arg-Arg-Arg-Arg-Arg-R8-Cys-Gln-Cys-Arg-Arg-Lys-S5-(Lys)ₙ-NH₂,
     wherein n=1=14
```

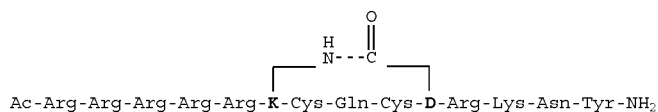

Ac-Arg-Arg-Arg-Arg-Arg-K-Cys-Gln-Cys-D-Arg-Lys-Asn-Tyr-NH₂

See Shepherd et al., JACS, 128(40), 13284-13289.

E. Cyclized Peptides

Cyclized peptides are peptides that are stabilized by virtue of a linkage rendering at least a portion of the peptide nonlinear, i.e., creating a closed loop. Exemplary cyclic peptide technologies are disclosed in U.S. Pat. Nos. 7,705,012, 7,589,170, 7,576,057, 6,818,659, 6,569,993, 6,184,345, 5,990,273, 5,939,383, 5,726,287, 5,723,575, 5,633,346 5,633,345, 5,616,684, and 5,596,078.

In a particular embodiment, the peptide of the present invention is cyclized. This may be achieved by generating a disulfide bond between the sulfur containing side changes of the Cys residues that are separated by Gln.

One particular cyclized peptide, GO-203-2c is a stable, rationally designed peptide that binds to the mucin-1 (MUC1) cytoplasmic domain to prevent oligomerization of MUC1.

GO-203-2c is a 16 residue D-amino acid peptide (2353.8 Da) containing a disulfide: Ac-(D)Arg-(D)Arg-(D)Arg-(D)Arg-(D)Arg-(D)Arg-(D)Arg-(D)Arg-(D)Arg-(D)Cys-(D)Gln-(D)Cys-(D)Arg-(D)Arg-(D)Lys-(D)Asn-NH₂ disulfide. GO-203-2c is the final design from a series of peptides synthesized to bind the MUC1 cytoplasmic domain and block formation of MUC1 oligomers. The cyclic peptide form was chosen in part because it could be manufactured in higher yield than the reduced species GO-203-2 and was more stable to interconversion during storage. All efficacious peptides in the series contained the same amino acid sequence (Cys-Gln-Cys-Arg-Arg-Lys-Asn) needed for binding the MUC1 cytoplasmic domain. The structure is shown below:

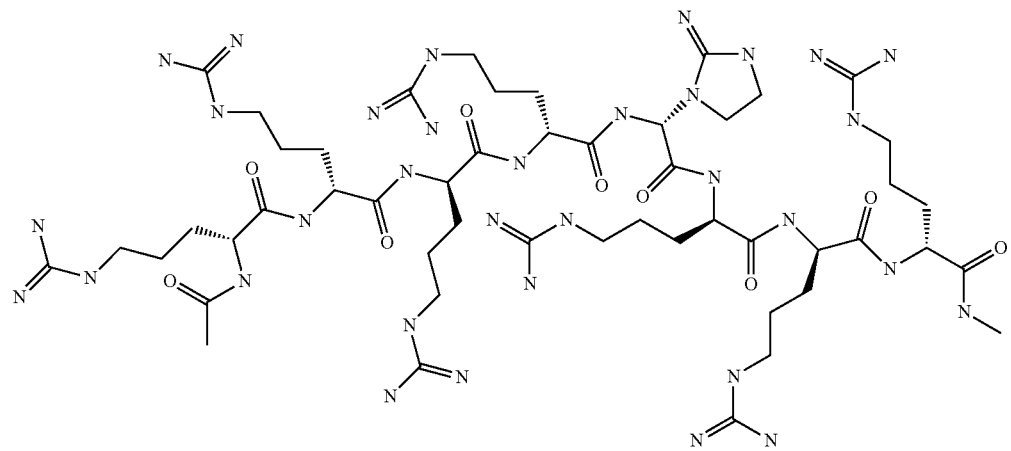

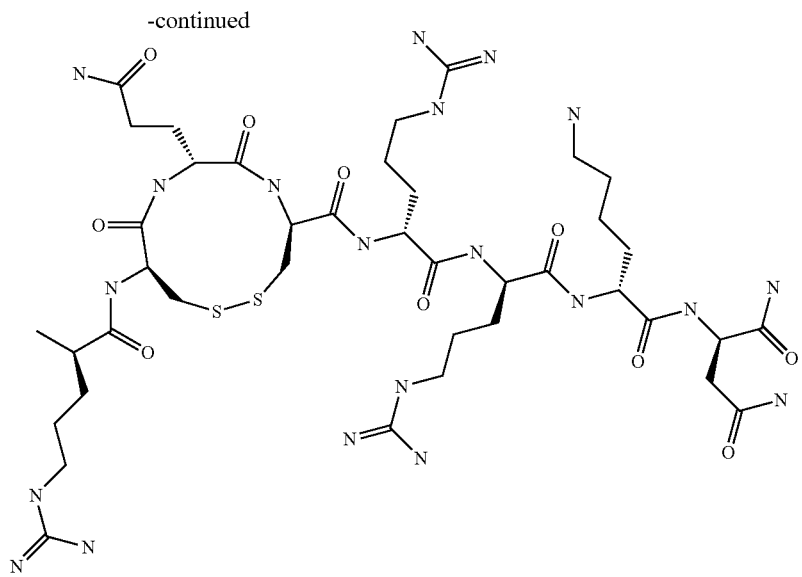

GO-203-2c is the stable oxidized disulfide form of the reduced dithiol GO-203-2, the redox form that ultimately binds to the MUC1 cytoplasmic domain. The oxidized form (GO-203-2c) readily converts to the reduced form (GO-203-2) in biological systems (see below). GO-203-2c is at least as efficacious as the reduced form (GO-203-2) when administered to either cell-based systems or xenograft tumor animal models. GO-203-2c has been tested on a variety of tumor cells expressing MUC1, both in vitro and in vivo.

Synthesis.

Resin-bound and fully protected linear GO-203-2c peptide is prepared by Solid Phase Peptide Synthesis (SPPS). SPPS immobilizes the growing peptide on an insoluble polymer (in this case Rink AM resin or Rink MBHA resin). The α-amino group protected amino acid Fmoc-D-Asn (Trt)-OH, which will form the C-terminal residue of the peptide, is attached through an amide bond to the Rink resin. By utilizing the Rink resin the cleavage of peptide from the resin will produce a C-terminal amide. A reagent is then applied to the protected aminoacyl polymer to selectively remove the blocking group from the amino acid residue. This reagent does not harm the link of the C-terminal residue to the polymer in any way. Stable blocking groups also protect reactive functional groups that are present on any of the amino acid residues of the final peptide sequence. By selectively protecting reactive side-chain functional groups, those groups remain completely intact throughout the synthesis, but may be removed to yield the free peptide. Following the removal of the labile protecting group, the next α-amino group protected amino acid is coupled to the aminoacyl polymer by use of a suitable coupling reaction. The Ninhydrin (Kaiser) test for free amine demonstrates completeness of reaction at the end of each coupling reaction. This cycle of deprotection and coupling is then repeated with each amino acid which is to be incorporated into the peptide chain. After all the amino acids have been attached, the α-amino protecting group is removed and the peptide is acetylated. After washing with methanol, the peptide-resin is removed from the SPPS reactor and dried under vacuum. At this stage, the peptide-resin is ready for further processing.

GO-203-2c peptide is cleaved from the resin and deprotected by acidolysis using TFA. To prevent side reactions, scavengers are added to react with intermediates generated by the TFA cleavage reactions. After completion of the cleavage, the resin is filtered and washed with TFA solution. The TFA filtrate is evaporated and the peptide is precipitated with ethyl ether, filtered and washed with ether. The N- and C-terminals of the free peptide both remain blocked (or "capped"): the N-terminal is acetylated by utilizing the Rink resin, the cleavage of peptide from the resin produces a C-terminal amide. RP-HPLC chromatography is used to check the identity, purity and yield of crude GO-203-2 product.

GO-203-2c peptide is cleaved from the resin and deprotected by acidolysis using TFA. To prevent side reactions, scavengers are added to react with intermediates generated by the TFA cleavage reactions. After completion of the cleavage, the resin is filtered and washed with TFA solution. The TFA filtrate is evaporated and the peptide is precipitated with ethyl ether, filtered and washed with ether. The N- and C-terminals of the free peptide both remain blocked (or "capped"): the N-terminal is acetylated by utilizing the Rink resin, the cleavage of peptide from the resin produces a C-terminal amide. RP-HPLC chromatography is used to check the identity, purity and yield of crude GO-203-2 product.

Salt Form:

Molar ratios of counterion:peptide were determined for Lot #P371010, produced under cGMP: Hydrochloride (approximate molar ratio 9:1 HCl:GO-203-2c); Trifluoroacetate (approximate molar ratio 2:1 TFA:GO-203-2c). There are 11 D-arg and 1D-lys residues in GO-203-2c available to form salts with counterions.

Hygroscopicity:

There is no evidence to support an isolable hydrate. GO-203-2c HCl is hygroscopic, and precautions must be taken to avoid moisture uptake while handling the drug substance powder.

Solubility:

The API is freely soluble in water (>240 mg/mL peptide), and 1% (v/v) aqueous acetic acid or 10% (v/v) aqueous acetonitrile (>110 mg/mL peptide). In these cases there was no gel formation for at least 5 days. The API is also soluble in acetate solutions, although observable precipitation or gelation may occur after 5 days at 5-25° C. or after 3 freeze-thaw cycles: 10 mM acetate pH 3.0-4.0, 0.9% NaCl (>50 mg/mL peptide) or 10 mM acetate pH 4.0 (7-37 mg/mL peptide).

UV/VIS Absorbance:

The extinction coefficient for GO-203-2c at 220 nm is 3.66 $(mg/ml)^{-1} cm^{-1}$ in water (determined for Reference Standard Lot #048G10). No significant absorbance was recorded for a 1 mg/mL aqueous solution of GO-203-2c in the range of 290-700 nm of the electromagnetic spectrum, indicating that photosafety does not need to be assessed.

The drug substance is isolated as the disulfide, with the disulfide bond cyclizing the D-cys10 and D-cys12 residues. The synthesis, cleavage, oxidation and purification steps use standard solid phase procedures as described in the literature. A solution phase procedure for converting the peptide to the cyclic disulfide was developed. Development experiments and stability studies demonstrated that the cyclic disulfide (GO-203-2c) of the peptide had yield and purity advantages over the dithiol redox related substance, GO-203-2. The biological properties of GO-203-2c will in part be governed by glutathione, which provides a significant portion of in vivo redox buffering capacity as mentioned above. Total glutathione levels approximate 20-30 µM in blood plasma, 0.5 mM in whole blood, and 5-10 mM intracellularly. GO-203-2c, in the presence of low levels of glutathione, readily re-forms the reduced (dithiol) GO-203-2 peptide and corresponding mixed disulfide products. Intracellular glutathione concentrations are sufficient to convert GO-203-2c (disulfide) to the GO-203-2 (dithiol) species that binds to the biological target, MUC1-CD.

Drug Product. GO-203-2c injection is a non-preserved, sterile, ready-to-use liquid dosage form provided in a glass vial with rubber closure and crimp seal. The only formulation ingredients are 10 mM acetate buffer, adjusted to pH 4.0 with sodium hydroxide, and Sterile Water for Injection. The drug product strength is 1 mg/mL, filled at a nominal 25 mL/vial in 30-mL, clear, type I borosilicate glass tubing vials with Teflon-lined stoppers. GO-203-2c injection will be added to the contents of an intravenous bag and administered as a single agent intravenously over 60 minutes. A daily dose will be administered for 21 consecutive days followed by a seven day rest. This cycle will be repeated every 28 days as long as there is no evidence of progressive disease and the treatment is associated with acceptable toxicity.

F. Design, Variants and Analogs

In one aspect, the present invention focuses on peptides comprising the sequence CQCRRK. Having identified this key structure in MUC1 oligomer formation, the inventors also contemplate that variants of the CQCRRK sequence may be employed. For example, certain non-natural amino acids that satisfy the structural constraints of the CQCRRK sequence may be substituted without a loss, and perhaps with an improvement in, biological function. In addition, the present inventors also contemplate that structurally similar compounds may be formulated to mimic the key portions of peptide or polypeptides of the present invention. Such compounds, which may be termed peptidomimetics, may be used in the same manner as the peptides of the invention and, hence, also are functional equivalents.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Methods for generating specific structures have been disclosed in the art. For example, α-helix mimetics are disclosed in U.S. Pat. Nos. 5,446,128; 5,710,245; 5,840,833; and 5,859,184. Methods for generating conformationally restricted β-turns and β-bulges are described, for example, in U.S. Pat. Nos. 5,440,013; 5,618,914; and 5,670,155. Other types of mimetic turns include reverse and γ-turns. Reverse turn mimetics are disclosed in U.S. Pat. Nos. 5,475,085 and 5,929,237, and γ-turn mimetics are described in U.S. Pat. Nos. 5,672,681 and 5,674,976.

By "molecular modeling" is meant quantitative and/or qualitative analysis of the structure and function of protein-protein physical interaction based on three-dimensional structural information and protein-protein interaction models. This includes conventional numeric-based molecular dynamic and energy minimization models, interactive computer graphic models, modified molecular mechanics models, distance geometry and other structure-based constraint models. Molecular modeling typically is performed using a computer and may be further optimized using known methods. Computer programs that use X-ray crystallography data are particularly useful for designing such compounds. Programs such as RasMol, for example, can be used to generate three dimensional models. Computer programs such as INSIGHT (Accelrys, Burlington, Mass.), GRASP (Anthony Nicholls, Columbia University), Dock (Molecular Design Institute, University of California at San Francisco), and Auto-Dock (Accelrys) allow for further manipulation and the ability to introduce new structures. The methods can involve the additional step of outputting to an output device a model of the 3-D structure of the compound. In addition, the 3-D data of candidate compounds can be compared to a computer database of, for example, 3-D structures.

Compounds of the invention also may be interactively designed from structural information of the compounds described herein using other structure-based design/modeling techniques (see, e.g., Jackson, 1997; Jones et al., 1996). Candidate compounds can then be tested in standard assays familiar to those skilled in the art. Exemplary assays are described herein.

The 3-D structure of biological macromolecules (e.g., proteins, nucleic acids, carbohydrates, and lipids) can be determined from data obtained by a variety of methodologies. These methodologies, which have been applied most effectively to the assessment of the 3-D structure of proteins, include: (a) x-ray crystallography; (b) nuclear magnetic resonance (NMR) spectroscopy; (c) analysis of physical distance constraints formed between defined sites on a macromolecule, e.g., intramolecular chemical crosslinks between residues on a protein (e.g., PCT/US00/14667, the disclosure of which is incorporated herein by reference in its entirety), and (d) molecular modeling methods based on a knowledge of the primary structure of a protein of interest, e.g., homology modeling techniques, threading algorithms, or ab initio structure modeling using computer programs such as MONSSTER (Modeling Of New Structures from Secondary and Tertiary Restraints) (see, e.g., International Application No. PCT/US99/11913, the disclosure of which is incorporated herein by reference in its entirety). Other molecular modeling techniques may also be employed in accordance with this invention (e.g., Cohen et al., 1990; Navia et al., 1992), the disclosures of which are incorporated herein by reference in their entirety). All these methods produce data that are amenable to computer analysis. Other spectroscopic methods that can also be useful in the method of the invention, but that do not currently provide atomic level structural detail about biomolecules, include circular dichroism and fluorescence and ultraviolet/visible light absorbance spectroscopy. A preferred method of analysis is x-ray crystallography. Descriptions of this procedure and of NMR spectroscopy are provided below.

X-ray Crystallography.

X-ray crystallography is based on the diffraction of x-radiation of a characteristic wavelength by electron clouds surrounding the atomic nuclei in a crystal of a molecule or molecular complex of interest. The technique uses crystals of purified biological macromolecules or molecular complexes (but these frequently include solvent components, co-factors, substrates, or other ligands) to determine near atomic resolution of the atoms making up the particular biological macromolecule. A prerequisite for solving 3-D structure by x-ray crystallography is a well-ordered crystal that will diffract x-rays strongly. The method directs a beam of x-rays onto a regular, repeating array of many identical molecules so that the x-rays are diffracted from the array in a pattern from which the structure of an individual molecule can be retrieved. Well-ordered crystals of, for example, globular protein molecules are large, spherical or ellipsoidal objects with irregular surfaces. The crystals contain large channels between the individual molecules. These channels, which normally occupy more than one half the volume of the crystal, are filled with disordered solvent molecules, and the protein molecules are in contact with each other at only a few small regions. This is one reason why structures of proteins in crystals are generally the same as those of proteins in solution.

Methods of obtaining the proteins of interest are described below. The formation of crystals is dependent on a number of different parameters, including pH, temperature, the concentration of the biological macromolecule, the nature of the solvent and precipitant, as well as the presence of added ions or ligands of the protein. Many routine crystallization experiments may be needed to screen all these parameters for the combinations that give a crystal suitable for x-ray diffraction analysis. Crystallization robots can automate and speed up work of reproducibly setting up a large number of crystallization experiments (see, e.g., U.S. Pat. No. 5,790,421, the disclosure of which is incorporated herein by reference in its entirety).

Polypeptide crystallization occurs in solutions in which the polypeptide concentration exceeds its solubility maximum (i.e., the polypeptide solution is supersaturated). Such solutions may be restored to equilibrium by reducing the polypeptide concentration, preferably through precipitation of the polypeptide crystals. Often polypeptides may be induced to crystallize from supersaturated solutions by adding agents that alter the polypeptide surface charges or perturb the interaction between the polypeptide and bulk water to promote associations that lead to crystallization.

Crystallizations are generally carried out between 4° C. and 20° C. Substances known as "precipitants" are often used to decrease the solubility of the polypeptide in a concentrated solution by forming an energetically unfavorable precipitating depleted layer around the polypeptide molecules (Weber, 1991). In addition to precipitants, other materials are sometimes added to the polypeptide crystallization solution. These include buffers to adjust the pH of the solution and salts to reduce the solubility of the polypeptide. Various precipitants are known in the art and include the following: ethanol, 3-ethyl-2-4 pentanediol, and many of the polyglycols, such as polyethylene glycol (PEG). The precipitating solutions can include, for example, 13-24% PEG 4000, 5-41% ammonium sulfate, and 1.0-1.5 M sodium chloride, and a pH ranging from 5.0-7.5. Other additives can include 0.1 M Hepes, 2-4% butanol, 20-100 mM sodium acetate, 50-70 mM citric acid, 120-130 mM sodium phosphate, 1 mM ethylene diamine tetraacetic acid (EDTA), and 1 mM dithiothreitol (DTT). These agents are prepared in buffers and are added dropwise in various combinations to the crystallization buffer. Proteins to be crystallized can be modified, e.g., by phosphorylation or by using a phosphate mimic (e.g., tungstate, cacodylate, or sulfate).

Commonly used polypeptide crystallization methods include the following techniques: batch, hanging drop, seed initiation, and dialysis. In each of these methods, it is important to promote continued crystallization after nucleation by maintaining a supersaturated solution. In the batch method, polypeptide is mixed with precipitants to achieve supersaturation, and the vessel is sealed and set aside until crystals appear. In the dialysis method, polypeptide is retained in a sealed dialysis membrane that is placed into a solution containing precipitant. Equilibration across the membrane increases the polypeptide and precipitant concentrations, thereby causing the polypeptide to reach supersaturation levels.

In the preferred hanging drop technique (McPherson, 1976), an initial polypeptide mixture is created by adding a precipitant to a concentrated polypeptide solution. The concentrations of the polypeptide and precipitants are such that in this initial form, the polypeptide does not crystallize. A small drop of this mixture is placed on a glass slide that is inverted and suspended over a reservoir of a second solution. The system is then sealed. Typically, the second solution contains a higher concentration of precipitant or other dehydrating agent. The difference in the precipitant concentrations causes the protein solution to have a higher vapor pressure than the second solution. Since the system containing the two solutions is sealed, an equilibrium is established, and water from the polypeptide mixture transfers to the second solution. This equilibrium increases the polypeptide and precipitant concentration in the polypeptide solution. At the critical concentration of polypeptide and precipitant, a crystal of the polypeptide may form.

Another method of crystallization introduces a nucleation site into a concentrated polypeptide solution. Generally, a concentrated polypeptide solution is prepared and a seed crystal of the polypeptide is introduced into this solution. If the concentrations of the polypeptide and any precipitants are correct, the seed crystal will provide a nucleation site around which a larger crystal forms.

Yet another method of crystallization is an electrocrystallization method in which use is made of the dipole moments of protein macromolecules that self-align in the Helmholtz layer adjacent to an electrode (see, e.g., U.S. Pat. No. 5,597,457, the disclosure of which is incorporated herein by reference in its entirety).

Some proteins may be recalcitrant to crystallization. However, several techniques are available to the skilled artisan to induce crystallization. For example, the removal of flexible polypeptide segments at the amino or carboxyl terminal end of the protein may facilitate production of crystalline protein samples. Removal of such segments can be done using molecular biology techniques or treatment of the protein with proteases such as trypsin, chymotrypsin, or subtilisin.

In diffraction experiments, a narrow and parallel beam of x-rays is taken from the x-ray source and directed onto the crystal to produce diffracted beams. The incident primary beams cause damage to both the macromolecule and solvent molecules. The crystal is, therefore, cooled (e.g., to between −220° C. and −50° C.) to prolong its lifetime. The primary beam must strike the crystal from many directions to produce all possible diffraction spots, so the crystal is rotated in the beam during the experiment. The diffracted spots are recorded on a film or by an electronic detector. Exposed film has to be digitized and quantified in a scanning device, whereas the electronic detectors feed the signals they detect directly into a computer. Electronic area detectors significantly reduce the time required to collect and measure diffraction data. Each diffraction beam, which is recorded as a spot on film or a detector plate, is defined by three properties: the amplitude, which is measured from the intensity of the spot; the wavelength, which is set by the x-ray source; and the phase, which is lost in x-ray experiments. All three properties are needed for all of the diffracted beams in order to determine the positions of the atoms giving rise to the diffracted beams. One way of determining the phases is called Multiple Isomorphous Replacement (MIR), which requires the introduction of exogenous x-ray scatterers (e.g., heavy atoms such metal atoms) into the unit cell of the crystal. For a more detailed description of MIR, see U.S. Pat. No. 6,093,573 (column 15) the disclosure of which is incorporated herein by reference in its entirety.

Atomic coordinates refer to Cartesian coordinates (x, y, and z positions) derived from mathematical equations involving Fourier synthesis of data derived from patterns obtained via diffraction of a monochromatic beam of x-rays by the atoms (scattering centers) of biological macromolecule of interest in crystal form. Diffraction data are used to calculate electron density maps of repeating units in the crystal (unit cell). Electron density maps are used to establish the positions (atomic coordinates) of individual atoms within a crystal's unit cell. The absolute values of atomic coordinates convey spatial relationships between atoms because the absolute values ascribed to atomic coordinates can be changed by rotational and/or translational movement along x, y, and/or z axes, together or separately, while maintaining the same relative spatial relationships among atoms. Thus, a biological macromolecule (e.g., a protein) whose set of absolute atomic coordinate values can be rotationally or translationally adjusted to coincide with a set of prior determined values from an analysis of another sample is considered to have the same atomic coordinates as those obtained from the other sample.

Further details on x-ray crystallography can be obtained from co-pending U.S. Application No. 2005/0015232, U.S. Pat. No. 6,093,573 and International Application Nos. PCT/US99/18441, PCT/US99/11913, and PCT/US00/03745. The disclosures of all these patent documents are incorporated herein by reference in their entirety.

NMR Spectroscopy.

Whereas x-ray crystallography requires single crystals of a macromolecule of interest, NMR measurements are carried out in solution under near physiological conditions. However, NMR-derived structures are not as detailed as crystal-derived structures.

While the use of NMR spectroscopy was until relatively recently limited to the elucidation of the 3-D structure of relatively small molecules (e.g., proteins of 100-150 amino acid residues), recent advances including isotopic labeling of the molecule of interest and transverse relaxation-optimized spectroscopy (TROSY) have allowed the methodology to be extended to the analysis of much larger molecules, e.g., proteins with a molecular weight of 110 kDa (Wider, 2000).

NMR uses radio-frequency radiation to examine the environment of magnetic atomic nuclei in a homogeneous magnetic field pulsed with a specific radio frequency. The pulses perturb the nuclear magnetization of those atoms with nuclei of nonzero spin. Transient time domain signals are detected as the system returns to equilibrium. Fourier transformation of the transient signal into a frequency domain yields a one-dimensional NMR spectrum. Peaks in these spectra represent chemical shifts of the various active nuclei. The chemical shift of an atom is determined by its local electronic environment. Two-dimensional NMR experiments can provide information about the proximity of various atoms in the structure and in three dimensional space. Protein structures can be determined by performing a number of two- (and sometimes 3- or 4-) dimensional NMR experiments and using the resulting information as constraints in a series of protein folding simulations.

More information on NMR spectroscopy including detailed descriptions of how raw data obtained from an NMR experiment can be used to determine the 3-D structure of a macromolecule can be found in: Protein NMR Spectroscopy, Principles and Practice, (1996); Gronenborn et al. (1990); and Wider (2000), supra., the disclosures of all of which are incorporated herein by reference in their entirety Also of interest are peptidomimetic compounds that are designed based upon the amino acid sequences of compounds of the invention that are peptides. Peptidomimetic compounds are synthetic compounds having a three-dimensional conformation "motif" that is substantially the same as the three-dimensional conformation of a selected peptide. The peptide motif provides the peptidomimetic compound with the ability to inhibit the oligomerization of MUC1. Peptidomimetic compounds can have additional characteristics that enhance their in vivo utility, such as increased cell permeability and prolonged biological half-life. The peptidomimetics typically have a backbone that is partially or completely non-peptide, but with side groups that are identical to the side groups of the amino acid residues that occur in the peptide on which the peptidomimetic is based. Several types of chemical bonds, e.g., ester, thioester, thioamide, retroamide, reduced carbonyl, dimethylene and ketomethylene bonds, are known in the art to be generally useful substitutes for peptide bonds in the construction of protease-resistant peptidomimetics.

G. Peptoids/Peptidomimetics

In accordance with the present invention, peptoids are provided that mimic the native structure of the peptides discussed above. In general, one creates an achiral peptoid by moving the amino acid sidechains over to the amide nitrogen. For chemical stability reasons, cysteine and serine residues need to be homologated. Other residue side chain lengths can remain as is or be homologated in order to assure proper alignment relative to the native peptide based on modeling experiments. Sometimes, chirality is introduced into one of these side chains to induce a handedness to an alpha-helix secondary structure, although the peptides described here do not include such a strategy. Also, certain residues favor helix formation while others may not, and since it has been reported that the alpha-helix of peptoids turns a somewhat more tightly than normal peptides, it has also been reported that some non-essential side chain residues must be deleted in order to maintain proper alignment of essential residues. Examples of peptoids are shown in FIG. 10.

Peptidomimetics are described in U.S. Pat. Nos. 5,939,268, 6,946,542, 7,166,568, 7,247,701, 7,589,170, 7,718,598, 7,863,239, 7,705,118, 7,202,332, 6,846,805, 6,706,862, 6,664,372, 6,566,493, 6,436,697, 6,197,963, 6,117,974, 5,817,879, 5,811,515, 5,811,512, 5,770,732, 5,552,534, 5,550,251, 5,288,707, and 5,250,564.

General design and methods of peptoid synthesis are described in U.S. Pat. Nos. 5,264,419, 5,801,148, 5,807,829, 5,811,387, 5,861,380, 5,869,455, 5,877,578, and 5,965,695, and U.S. Patent Publication 2003/0187188, 2005/0043509, which are exemplary in nature and incorporated herein by reference.

IV. Therapies

A. Pharmaceutical Formulations and Routes of Administration

Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. Such routes include oral, nasal, buccal, rectal, vaginal or topical route. Alternatively, administration may be by orthotopic, intradermal, subcutaneous, intramuscular, intratumoral, intraperitoneal, or intravenous injection. Such compositions would normally be administered as pharmaceutically acceptable compositions, described supra.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences," 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The peptides and mimetics thereof can be delivered by encapsulating or embedding in a delivery vehicle. For example, liposomes, which are artificially prepared vesicles made of lipid bilayers have been used to delivery a variety of drugs. Liposomes can be composed of naturally-derived phospholipids with mixed lipid chains (like egg phosphatidylethanolamine) or other surfactants. In particular, liposomes containing cationic or neutral lipids have been used in the formulation of drugs. Liposomes should not be confused with micelles and reverse micelles composed of monolayers, which also can be used for delivery.

Nanoparticles are generally considered to be particulate substances having a diameter of 100 nm or less. In contrast to liposomes, which are hollow, nanoparticles tend to be solid. Thus, the drug will be less entrapped and more either embedded in or coated on the nanoparticle. Nanoparticles can be made of metals including oxides, silica, polymers such as polymethyl methacrylate, and ceramics. Similarly, nanoshells are somewhat larger and encase the delivered substances with these same materials. Either nanoparticles or nanoshells permit sustained or controlled release of the peptide or mimetic, and can stabilize it to the effects of in vivo environment.

Another modification for delivery of peptides and peptidomimetics is PEG-ylation. PEG-ylation is the process of covalent attachment of polyethylene glycol polymer chains to another molecule, normally a drug or therapeutic protein. PEG-ylation is routinely achieved by incubation of a reactive derivative of PEG with the target macromolecule. The covalent attachment of PEG to a drug or therapeutic protein can "mask" the agent from the host's immune system (reduced immunogenicity and antigenicity), increase the hydrodynamic size (size in solution) of the agent which prolongs its circulatory time by reducing renal clearance. PEG-ylation can also provide water solubility to hydrophobic drugs and proteins. Exemplary PEG-ylation technologies are described in U.S. Pat. Nos. 7,666,400, 7,610,156, 7,587,286, 6,552,170 and 6,420,339.

B. Inflammatory Disease States and Conditions
i. Cancer

Cancer results from the outgrowth of a clonal population of cells from tissue. The development of cancer, referred to as carcinogenesis, can be modeled and characterized in a number of ways. An association between the development of cancer and inflammation has long-been appreciated. The inflammatory response is involved in the host defense against microbial infection, and also drives tissue repair and regeneration. Considerable evidence points to a connection between inflammation and a risk of developing cancer, i.e., chronic inflammation can lead to dysplasia.

Studies have estimated that nearly 15% of worldwide cancer is associated with microbial infection. Organisms such as human papilloma virus (HPV), hepatitis B and C virus, HIV, and *Helicobacter pylori* all have been linked to cancer. In other cases, environmental conditions causing chronic irritation and subsequent inflammation can also predispose to cancer, including cigarette smoke, asbestos and silica.

In the case of some types of viral infection, virally-encoded genes can contribute to cellular transformation. An example is the HPV oncoproteins E6 and E7. However, other microbes associated with cancer do not operate in this fashion as they are not transforming. For example, certain strains of *H. pylori* contain factors that affect host cell signaling but do not contain oncogenes. Interestingly, it has been observed that *H. pylori* induces MUC1.

Other ways in which chronic inflammatory states can lead to genomic lesions and tumor initiation are chemical. For example, host cells fight microbial infection by the production of free radicals. In addition to their anti-microbial effects, these molecules lead to oxidative damage and nitration of DNA bases which increases the risk of DNA mutations even in host cells.

Yet another path to cellular dysregulation may result from the cell death that occurs in infection or other inflammatory insult. Lost cells must be repopulated by the expansion of other cells, sometimes undifferentiated precursor cells such as tissue stem cells. Not surprisingly, many inflammatory pathways function to mediate survival and proliferation. Thus, in attempting to mediating tissue repair, the inflammatory response may unwittingly provide excessive survival and proliferative signals to cells, thus leading to tumorigenesis.

Because of the link between cancer and inflammation, the ability of the peptides and peptide analogs of the present invention to reduce inflammatory signalling pathways can be exploited in a pre-cancer or cancer risk situation to prevent or delay the onset of dysplastic growth. Cancer cells to which the methods of the present invention can be applied include generally any cell that expresses MUC1, and more particularly, that overexpresses MUC1. An appropriate cancer cell can be a breast cancer, lung cancer, colon cancer, pancreatic cancer, renal cancer, stomach cancer, liver cancer, bone cancer, hematological cancer (e.g., leukemia or lymphoma), neural tissue cancer, melanoma, ovarian cancer, testicular cancer, prostate cancer, cervical cancer, vaginal cancer, or bladder cancer cell. In addition, the methods of the invention can be applied to a wide range of species, e.g., humans, non-human primates (e.g., monkeys, baboons, or chimpanzees), horses, cattle, pigs, sheep, goats, dogs, cats, rabbits, guinea pigs, gerbils, hamsters, rats, and mice. Cancers may also be recurrent, metastatic and/or multi-drug resistant, and the methods of the present invention may be particularly applied to such cancers so as to prolong or re-induce remission, to prevent or limit metastasis, and/or to treat multi-drug resistant cancers.

The inventors propose that the local or regional delivery of MUC1 peptides to patients with cancer will be a very efficient method for treating the clinical disease. Similarly, the chemo- or radiotherapy (in combinations, as discussed below) may be directed to a particular, affected region of the subject's body. Alternatively, regional or systemic delivery of the agent(s) may be appropriate in certain circumstances, for example, where metastasis has occurred.

ii. Sepsis

Sepsis is a serious medical condition characterized by a whole-body inflammatory state caused by infection. Traditionally the term sepsis has been used interchangeably with septicaemia and septicemia ("blood poisoning"). However, these terms are no longer considered synonymous; septicemia is considered a subset of sepsis.

Symptoms of sepsis are often related to the underlying infectious process. When the infection crosses into sepsis, the resulting symptoms are that of systemic inflammatory response syndrome (SIRS): general inflammation, fever, elevated white blood cell count (leukocytosis), and raised heart rate (tachycardia) and breathing rate (tachypnea). Secondary to the above, symptoms also include flu like chills.

The immunological response that causes sepsis is a systemic inflammatory response causing widespread activation of inflammation and coagulation pathways. This may progress to dysfunction of the circulatory system and, even under optimal treatment, may result in the multiple organ dysfunction syndrome and eventually death.

Sepsis is considered present if infection is highly suspected or proven and two or more of the following systemic inflammatory response syndrome (SIRS) criteria are met:
  heart rate>90 beats per minute
  body temperature<36 (96.8° F.) or >38° C. (100.4° F.)
  hyperventilation (high respiratory rate)>20 breaths per minute or, on blood gas, a $P_aCO_2$ less than 32 mm Hg
  white blood cell count<4000 cells/mm$^3$ or >12000 cells/mm$^3$ (<4×10$^9$ or >12×10$^9$ cells/L), or greater than 10% band forms (immature white blood cells).
Consensus definitions however continue to evolve with the latest expanding the list of signs and symptoms of sepsis to reflect clinical bedside experience.

The more critical subsets of sepsis are severe sepsis (sepsis with acute organ dysfunction) and septic shock (sepsis with refractory arterial hypotension). Alternatively, when two or more of the systemic inflammatory response syndrome criteria are met without evidence of infection, patients may be diagnosed simply with "SIRS." Patients with SIRS and acute organ dysfunction may be termed "severe SIRS."

Patients are defined as having "severe sepsis" if they have sepsis plus signs of systemic hypoperfusion; either end organ dysfunction or a serum lactate greater than 4 mmol/dL. Patient are defined as having septic shock if they have sepsis plus hypotension after an appropriate fluid bolus (typically 20 ml/kg of crystaloid). The criteria for diagnosing an adult with sepsis do not apply to infants under one month of age. In infants, only the presence of infection plus a "constellation" of signs and symptoms consistent with the systemic response to infection are required for diagnosis.

The therapy of sepsis rests on antibiotics, surgical drainage of infected fluid collections, fluid replacement and appropriate support for organ dysfunction. This may include hemodialysis in kidney failure, mechanical ventilation in pulmonary dysfunction, transfusion of blood products, and drug and fluid therapy for circulatory failure. Ensuring adequate nutrition, if necessary by parenteral nutrition, is important during prolonged illness.

A problem in the adequate management of septic patients has been the delay in administering therapy after sepsis has been recognized. Published studies have demonstrated that for every hour delay in the administration of appropriate antibiotic therapy there is an associated 7% rise in mortality. A large international collaboration was established to educate people about sepsis and to improve patient outcomes with sepsis, entitled the "Surviving Sepsis Campaign." The Campaign has published an evidence-based review of management strategies for severe sepsis, with the aim to publish a complete set of guidelines in subsequent years.

Most therapies aimed at the inflammatory process itself have failed to improve outcome, however drotrecogin alfa (activated protein C, one of the coagulation factors) has been shown to decrease mortality from about 31% to about 25% in severe sepsis. To qualify for drotrecogin alfa, a patient must have severe sepsis or septic shock with an APACHE II score of 25 or greater and a low risk of bleeding. Low dose hydrocortisone treatment has shown promise for septic shock patients with relative adrenal insufficiency as defined by ACTH stimulation testing.

Standard treatment of infants with suspected sepsis consists of supportive care, maintaining fluid status with intravenous fluids, and the combination of a β-lactam antibiotic (such as ampicillin) with an aminoglycoside such as gentamicin.

iii. Trauma

Physical trauma is a serious and body-altering physical injury, such as the removal of a limb. Blunt force trauma, a type of physical trauma caused by impact or other force applied from or with a blunt object, whereas penetrating trauma is a type of physical trauma in which the skin or tissues are pierced by an object. Trauma can also be described as both unplanned, such as an accident, or planned, in the case of surgery. Both can be characterized by mild to severe tissue damage, blood loss and/or shock, and both may lead to subsequent infection, including sepsis. The present invention provides to treatment of trauma, including both pre-treatment (in the case of a medical procedure) and treatment after trauma injury as occurred.

Surgery.

Surgery uses operative manual and instrumental techniques on a patient to investigate and/or treat a pathological condition such as disease or injury, to help improve bodily function or appearance, or sometimes for some other reason. The present invention can address trauma resulting from surgeries, as defined further below.

As a general rule, a procedure is considered surgical when it involves cutting of a patient's tissues or closure of a previously sustained wound. Other procedures that do not necessarily fall under this rubric, such as angioplasty or endoscopy, may be considered surgery if they involve common surgical procedure or settings, such as use of a sterile environment, anesthesia, antiseptic conditions, typical surgical instruments, and suturing or stapling. All forms of surgery are considered invasive procedures; so-called noninvasive surgery usually refers to an excision that does not penetrate the structure being addressed (e.g., laser ablation of the cornea) or to a radiosurgical procedure (e.g., irradiation of a tumor). Surgery can last from minutes to hours.

Surgical procedures are commonly categorized by urgency, type of procedure, body system involved, degree of invasiveness, and special instrumentation. Elective surgery is done to correct a non-life-threatening condition, and is carried out at the patient's request, subject to the surgeon's and the surgical facility's availability. Emergency surgery is surgery which must be done quickly to save life, limb, or functional capacity. Exploratory surgery is performed to aid or confirm a diagnosis. Therapeutic surgery treats a previously diagnosed condition.

Amputation involves cutting off a body part, usually a limb or digit. Replantation involves reattaching a severed body part. Reconstructive surgery involves reconstruction of an injured, mutilated, or deformed part of the body. Cosmetic surgery is done to improve the appearance of an otherwise normal structure. Excision is the cutting out of an organ, tissue, or other body part from the patient. Transplant surgery is the replacement of an organ or body part by insertion of another from different human (or animal) into the patient. Removing an organ or body part from a live human or animal for use in transplant is also a type of surgery.

When surgery is performed on one organ system or structure, it may be classed by the organ, organ system or tissue involved. Examples include cardiac surgery (performed on the heart), gastrointestinal surgery (performed within the digestive tract and its accessory organs), and orthopedic surgery (performed on bones and/or muscles).

Minimally invasive surgery involves smaller outer incision(s) to insert miniaturized instruments within a body cavity or structure, as in laparoscopic surgery or angioplasty. By contrast, an open surgical procedure requires a large incision to access the area of interest. Laser surgery involves use of a laser for cutting tissue instead of a scalpel or similar surgical instruments. Microsurgery involves the use of an operating microscope for the surgeon to see small structures. Robotic surgery makes use of a surgical robot, such as Da Vinci or Zeus surgical systems, to control the instrumentation under the direction of the surgeon.

Traumatic Hemorrhage.

Traumatic hemorrhage accounts for much of the wide ranging international impact of injury, causing a large proportion of deaths and creating great morbidity in the injured. Despite differences in pre-hospital care, the acute management of traumatic hemorrhage is similar around the world and follows well accepted published guidelines. A critically injured patient's care occurs as four, often overlapping segments: the resuscitative, operative, and critical care phases. The diagnosis and control of bleeding should be a high priority during all of the phases of trauma care and is especially important in the patient who is in hemorrhagic shock. Early attempts at hemorrhage control include direct control of visible sources of severe bleeding with direct pressure, pressure dressings, or tourniquets; stabilization of long bone and pelvic fractures; and keeping the patient warm. During the resuscitative phase, warmed intravenous fluids, hypotensive resuscitation prior to surgical control of hemorrhage, and appropriate transfusion of blood and blood products are provided. In the operative phase, surgical control of the hemorrhage and any other injury, and additional transfusion is provide. Finally, the critical care phase provides for post-operative support and tissue perfusion.

iv. Acute Pancreatitis

Acute pancreatitis is rapidly-onset inflammation of the pancreas. Depending on its severity, it can have severe complications and high mortality despite treatment. While mild cases are often successfully treated with conservative measures or laparoscopy, severe cases require invasive surgery (often more than one intervention) to contain the disease process.

v. Acute Respiratory Distress Syndrome

Acute respiratory distress syndrome (ARDS), also known as respiratory distress syndrome (RDS) or adult respiratory distress syndrome (in contrast with IRDS) is a serious reaction to various forms of injuries to the lung. This is the most important disorder resulting in increased permeability pulmonary edema.

ARDS is a severe lung disease caused by a variety of direct and indirect insults. It is characterized by inflammation of the lung parenchyma leading to impaired gas exchange with concomitant systemic release of inflammatory mediators causing inflammation, hypoxemia and frequently resulting in multiple organ failure. This condition is life threatening and often lethal, usually requiring mechanical ventilation and admission to an intensive care unit. A less severe form is called acute lung injury (ALI).

ARDS can occur within 24 to 48 hours of an injury or attack of acute illness. In such a case the patient usually presents with shortness of breath, tachypnea, and symptoms related to the underlying cause, i.e., shock. Long term illnesses can also trigger it, such as malaria. The ARDS may then occur sometime after the onset of a particularly acute case of the infection.

An arterial blood gas analysis and chest X-ray allow formal diagnosis by inference using the aforementioned criteria. Although severe hypoxemia is generally included, the appropriate threshold defining abnormal $PaO_2$ has never been systematically studied. Any cardiogenic cause of pulmonary edema should be excluded. This can be done by placing a pulmonary artery catheter for measuring the pulmonary artery wedge pressure. However, this is not necessary and is now rarely done as abundant evidence has emerged demonstrating that the use of pulmonary artery catheters does not lead to improved patient outcomes in critical illness including ARDS. Plain chest X-rays are sufficient to document bilateral alveolar infiltrates in the majority of cases. While CT scanning leads to more accurate images of the pulmonary parenchyma in ARDS, its has little utility in the clinical management of patients with ARDS, and remains largely a research tool.

Acute respiratory distress syndrome is usually treated with mechanical ventilation in the Intensive Care Unit. Ventilation is usually delivered through oro-tracheal intubation, or tracheostomy whenever prolonged ventilation ($\geq 2$ weeks) is deemed inevitable. The possibilities of non-invasive ventilation are limited to the very early period of the disease or, better, to prevention in individuals at risk for the development of the disease (atypical pneumonias, pulmonary contusion, major surgery patients). Treatment of the underlying cause is imperative, as it tends to maintain the ARDS picture. Appropriate antibiotic therapy must be administered as soon as microbiological culture results are available. Empirical therapy may be appropriate if local microbiological surveillance is efficient. More than 60% ARDS patients experience a (nosocomial) pulmonary infection either before or after the onset of lung injury. The origin of infection, when surgically treatable, must be operated on. When sepsis is diagnosed, appropriate local protocols should be enacted.

vi. Ischemia-Reperfusion Injury

Reperfusion injury refers to damage to tissue caused when blood supply returns to the tissue after a period of ischemia. The absence of oxygen and nutrients from blood creates a condition in which the restoration of circulation results in inflammation and oxidative damage through the induction of oxidative stress rather than restoration of normal function.

The damage of reperfusion injury is due in part to the inflammatory response of damaged tissues. White blood cells carried to the area by the newly returning blood release a host of inflammatory factors such as interleukins as well as free radicals in response to tissue damage. The restored blood flow reintroduces oxygen within cells that damages cellular proteins, DNA, and the plasma membrane. Damage to the cell's membrane may in turn cause the release of more free radicals. Such reactive species may also act indirectly in redox signaling to turn on apoptosis. Leukocytes may also build up in small capillaries, obstructing them and leading to more ischemia.

Reperfusion injury plays a part in the brain's ischemic cascade, which is involved in stroke and brain trauma. Repeated bouts of ischemia and reperfusion injury also are thought to be a factor leading to the formation and failure to heal of chronic wounds such as pressure sores and diabetic foot ulcers. Continuous pressure limits blood supply and causes ischemia, and the inflammation occurs during reperfusion. As this process is repeated, it eventually damages tissue enough to cause a wound.

In prolonged ischemia (60 min or more), hypoxanthine is formed as breakdown product of ATP metabolism. The enzyme xanthine dehydrogenase is converted to xanthine oxidase as a result of the higher availability of oxygen. This oxidation results in molecular oxygen being converted into highly reactive superoxide and hydroxyl radicals. Xanthine oxidase also produces uric acid, which may act as both a prooxidant and as a scavenger of reactive species such as peroxinitrite. Excessive nitric oxide produced during reperfusion reacts with superoxide to produce the potent reactive species peroxynitrite. Such radicals and reactive oxygen species attack cell membrane lipids, proteins, and glycosaminoglycans, causing further damage. They may also initiate specific biological processes by redox signaling.

vii. Cardiovascular Disease

Cardiovascular disease refers to the class of diseases that involve the heart or blood vessels (arteries and veins). While the term technically refers to any disease that affects the cardiovascular system, it is usually used to refer to those related to atherosclerosis (arterial disease). These conditions have similar causes, mechanisms, and treatments. Treatment of cardiovascular disease depends on the specific form of the disease in each patient, but effective treatment always includes preventive lifestyle changes discussed above. Medications, such as blood pressure reducing medications, aspirin and the statin cholesterol-lowering drugs may be helpful. In some circumstances, surgery or angioplasty may be warranted to reopen, repair, or replace damaged blood vessels Most Western countries face high and increasing rates of cardiovascular disease. Each year, heart disease kills more Americans than cancer. Diseases of the heart alone caused 30% of all deaths, with other diseases of the cardiovascular system causing substantial further death and disability. Up until the year 2005, it was the number 1 cause of death and disability in the United States and most European countries. A large histological study (PDAY) showed vascular injury accumulates from adolescence, making primary prevention efforts necessary from childhood.

Some biomarkers are thought to offer a more detailed risk of cardiovascular disease. However, the clinical value of these biomarkers is questionable. Currently, biomarkers which may reflect a higher risk of cardiovascular disease include:

higher fibrinogen and PAI-1 blood concentrations
elevated homocysteine, or even upper half of normal
elevated blood levels of asymmetric dimethylarginine
high inflammation as measured by C-reactive protein
levated blood levels of B-type natriuretic peptide (BNP)

Various forms of cardiovascular disease include aneurysms, angina, arrhythmia, atherosclerosis, cardiomyopathy, cerebrovascular disease, congenital heart disease, congestive heart failure, myocarditis, valve disease, coronary artery disease, dilated cardiomyopathy, diastolic dysfunction, endocarditis, high blood pressure (hypertension), hypertrophic cardiomyopathy, nitral valve prolapse, myocardial infarction, and venous thromboembolism.

viii. Autoimmune/Inflammtory Disease

The present invention contemplates the treatment of a variety of autoimmune and/or inflammatory disease states such as spondyloarthropathy, ankylosing spondylitis, psoriatic arthritis, reactive arthritis, enteropathic arthritis, ulcerative colitis, Crohn's disease, irritable bowel disease, inflammatory bowel disease, rheumatoid arthritis, juvenile rheumatoid arthritis, familial Mediterranean fever, amyotrophic lateral sclerosis, Sjogren's syndrome, early arthritis, viral arthritis, multiple sclerosis, or psoriasis. The diagnosis and treatment of these diseases are well documented in the literature.

ix. Chemotherapy, Radiotherapy and Cytokine Therapy Toxicity

Various forms of cancer therapy, including chemotherapy, radiation, and cytokines, are associated with toxicity, sometimes severe, in the cancer patient. To the extent that the toxicity is caused at least in part by the extracellular actions of histones, the present invention seeks to reduce this toxicity using the pharmaceutical compositions of the present invention, thereby reducing or alleviating discomfort on the part of the patient, as well as permitting higher doses of the therapy.

x. Burns

In medicine, a burn may be an injury caused by heat, cold, electricity, chemicals, friction or radiation. First-degree burns are usually limited to redness (erythema), a white plaque, and minor pain at the site of injury. These burns usually extend only into the epidermis. Second-degree burns additionally fill with clear fluid, have superficial blistering of the skin, and can involve more or less pain depending on the level of nerve involvement. Second-degree burns involve the superficial (papillary) dermis and may also involve the deep (reticular) dermis layer. Third-degree burns additionally have charring of the skin, and produce hard, leather-like eschars. An eschar is a scab that has separated from the unaffected part of the body. Frequently, there is also purple fluid. These types of burns are often painless, because nerve endings have been destroyed in the burned areas. Serious burns, especially if they cover large areas of the body, can cause death; any hint of burn injury to the lungs (e.g., through smoke inhalation) is a medical emergency.

Burns that injure the tissues underlying the skin, such as the muscles or bones, are sometimes categorized as fourth-degree burns. These burns are broken down into three additional degrees: fourth-degree burns result in the skin being irretrievably lost, fifth-degree burns result in muscle being irretrievably lost, and sixth-degree burns result in bone being charred.

A newer classification of "Superficial Thickness," "Partial Thickness" (which is divided into superficial and deep categories) and "Full Thickness" relates more precisely to the epidermis, dermis and subcutaneous layers of skin and is used to guide treatment and predict outcome.

Chemical burns are usually caused by chemical compounds, such as sodium hydroxide (lye), silver nitrate, and more serious compounds (such as sulfuric acid). Most chemicals (but not all) that can cause moderate to severe chemical burns are strong acids or bases. Nitric acid, as an oxidizer, is possibly one of the worst burn-causing chemicals. Hydrofluoric acid can eat down to the bone and its burns are often not immediately evident. Most chemicals that can cause moderate to severe chemical burns are called caustic.

Electrical burns are generally symptoms of electric shock, being struck by lightning, being defibrillated or cardioverted without conductive gel, etc. The internal injuries sustained may be disproportionate to the size of the "burns" seen—as these are only the entry and exit wounds of the electrical current.

Burns are assessed in terms of total body surface area (TBSA), which is the percentage affected by partial thickness or full thickness burns (superficial thickness burns are not counted). The rule of nines is used as a quick and useful way to estimate the affected TBSA. The first step in managing a person with a burn is to stop the burning process. With dry powder burns, the powder should be brushed off first. With other burns, the affected area should be rinsed with a large amount of clean water to remove foreign bodies and help stop the burning process. Cold water should never be applied to any person with extensive burns, as it may severely compromise the burn victim's temperature status. At this stage of management, it is also critical to assess the airway status. If the patient was involved in a fire, then it must be assumed that he or she has sustained inhalation injury until proven otherwise, and treatment should be managed accordingly.

Once the burning process has been stopped, and airway status is ensured, the patient should be volume resuscitated according to the Parkland formula. This formula dictates that the amount of Lactated Ringer's solution to deliver in the first twenty four hours after time of injury is:

fluid=4 cc×% TBSA×weight in kg

% TBSA excludes any first degree burn

Half of this fluid should be given in the first eight hours post injury and the rest in the subsequent sixteen hours. The formula is a guide only and infusions must be tailored to urine output and central venous pressure. Inadequate fluid resuscitation causes renal failure and death. Severe edema in full thickness burns may be treated by escharotomy.

C. Treatment Methods

Peptides or analogs that inhibit MUC1 oligomer formation are generally useful as anti-inflammatories. They can be administered to mammalian subjects (e.g., human patients) alone or in conjunction with other drugs that modulate inflammation. The compounds can also be administered to subjects that are genetically and/or due to, for example, physiological and/or environmental factors, susceptible to inflammation, e.g., subjects with a family history of inflammatory disease, or subjects with chronic inflammation or subject to chronic stress.

The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.0001-100 mg/kg. Wide variations in the needed dosage are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization as is well understood in the art. Administrations can be single or multiple (e.g., 2-, 3-, 4-, 6-, 8-, 10-, 20-, 50-, 100-, 150-, or more times). Encapsulation of the polypeptide in a suitable delivery vehicle (e.g., polymeric microparticles or implantable devices) may increase the efficiency of delivery, particularly for oral delivery.

D. Combination Therapies

It is common in many fields of medicine to treat a disease with multiple therapeutic modalities, often called "combination therapies." Inflammatory disease are no exception.

To treat inflammatory disorders using the methods and compositions of the present invention, one would generally contact a target cell or subject with a MUC1 antagonist and at least one other therapy. These therapies would be provided in a combined amount effective to achieve a reduction in one or more disease parameter. This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes the MUC1 antagonist and the other includes the other agent.

Alternatively, the MUC1 antagonist may precede or follow the other treatment by intervals ranging from minutes to weeks. One would generally ensure that a significant period of time did not expire between the time of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 12 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the MUC1 antagonist or the other therapy will be desired. Various combinations may be employed, where the MUC1 antagonist is "A," and the other therapy is "B," as exemplified below:

| | | | | | | | |
|---|---|---|---|---|---|---|---|
| A/B/A | B/A/B | B/B/A | A/A/B | B/A/A | A/B/B | B/B/B/A | B/B/A/B |
| A/A/B/B | A/B/A/B | A/B/B/A | B/B/A/A | B/A/B/A | B/A/A/B | B/B/B/A | |
| A/A/A/B | B/A/A/A | A/B/A/A | A/A/B/A | A/B/B/B | B/A/B/B | B/B/A/B | |

Other combinations are contemplated. In particular, the invention may be applied as a combination to treat cancers, such as any of those discussed above. To kill cells, inhibit cell growth, inhibit metastasis, inhibit angiogenesis or otherwise reverse or reduce the malignant phenotype of tumor cells, using the methods and compositions of the present invention, one would generally contact a target cell with a MUC1 peptide and at least one other therapy. These therapies would be provided in a combined amount effective to kill or inhibit proliferation of the cell. This process may involve contacting the cells with the agents/therapies at the same time. This may be achieved by contacting the cell with a single composition or pharmacological formulation that includes both agents, or by contacting the cell with two distinct compositions or formulations, at the same time, wherein one composition includes the MUC1 peptide and the other includes the agent.

Agents or factors suitable for use in a combined therapy include any chemical compound or treatment method that induces DNA damage when applied to a cell. Such agents and factors include radiation and waves that induce DNA damage such as, irradiation, microwaves, electronic emissions, and the like. A variety of chemical compounds, also described as "chemotherapeutic" or "genotoxic agents," are intended to be of use in the combined treatment methods disclosed herein. In treating cancer according to the invention, one would contact the tumor cells with an agent in addition to the expression construct. This may be achieved by irradiating the localized tumor site; alternatively, the tumor cells may be contacted with the agent by administering to the subject a therapeutically effective amount of a pharmaceutical composition.

Various classes of chemotherapeutic agents are comtemplated for use with in combination with peptides of the present invention. For example, selective estrogen receptor antagonists ("SERMs"), such as Tamoxifen, 4-hydroxy Tamoxifen (Afimoxfene), Falsodex, Raloxifene, Bazedoxifene, Clomifene, Femarelle, Lasofoxifene, Ormeloxifene, and Toremifene.

Chemotherapeutic agents contemplated to be of use, include, e.g., camptothecin, actinomycin-D, mitomycin C. The invention also encompasses the use of a combination of one or more DNA damaging agents, whether radiation-based or actual compounds, such as the use of X-rays with cisplatin or the use of cisplatin with etoposide. The agent may be prepared and used as a combined therapeutic composition, or kit, by combining it with a MUC1 peptide, as described above.

Heat shock protein 90 is a regulatory protein found in many eukaryotic cells. HSP90 inhibitors have been shown to be useful in the treatment of cancer. Such inhibitors include Geldanamycin, 17-(Allylamino)-17-demethoxygeldanamycin, PU-H71 and Rifabutin.

Agents that directly cross-link DNA or form adducts are also envisaged. Agents such as cisplatin, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25-75 mg/m$^2$ at 21 day intervals for doxorubicin, to 35-50 mg/m$^2$ for etoposide intravenously or double the intravenous dose orally. Microtubule inhibitors, such as taxanes, also are contemplated. These molecules are diterpenes produced by the plants of the genus *Taxus*, and include paclitaxel and docetaxel.

Epidermal growth factor receptor inhibitors, such as Iressa, mTOR, the mammalian target of rapamycin, also known as FK506-binding protein 12-rapamycin associated protein 1 (FRAP1) is a serine/threonine protein kinase that regulates cell growth, cell proliferation, cell motility, cell survival, protein synthesis, and transcription. Rapamycin and analogs thereof ("rapalogs") are therefore contemplated for use in combination cancer therapy in accordance with the present invention.

Another possible combination therapy with the peptides claimed herein is TNF-α (tumor necrosis factor-alpha), a cytokine involved in systemic inflammation and a member of a group of cytokines that stimulate the acute phase reaction. The primary role of TNF is in the regulation of immune cells. TNF is also able to induce apoptotic cell death, to induce inflammation, and to inhibit tumorigenesis and viral replication.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, x-rays, and/or the directed delivery of radioisotopes to tumor cells. Other forms of DNA damaging factors are also contemplated such as microwaves and UV-irradiation. It is most likely that all of these factors effect a broad range of damage DNA, on the precursors of DNA, the replication and repair of DNA, and the assembly and maintenance of chromosomes. Dosage ranges for x-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

In addition to combining MUC1 therapies with chemo- and radiotherapies, it also is contemplated that combination with immunotherapy, hormone therapy, toxin therapy and surgery. In particular, one may employ targeted therapies such as Avastin, Erbitux, Gleevec, Herceptin and Rituxan.

It also should be pointed out that any of the foregoing therapies may prove useful by themselves in treating cancer.

Other agents or factors suitable for use in a combined therapy against an inflammatory disorder include steroids, glucocorticoids, non-steriodal anti-inflammatory drugs (NSAIDS; including COX-1 and COX-2 inhibitors), aspirin, ibuprofen, and naproxen. Analgesics are commonly associated with anti-inflammatory drugs but which have no anti-inflammatory effects. An example is paracetamol, called acetaminophen in the U.S. and sold under the brand name of Tylenol. As opposed to NSAIDS, which reduce pain and inflammation by inhibiting COX enzymes, paracetamol has recently been shown to block the reuptake of endocannabinoids, which only reduces pain, likely explaining why it has minimal effect on inflammation.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

It also should be pointed out that any of the foregoing therapies may prove useful by themselves in treating inflammation.

V. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Assay for Inhibition of Cell Proliferation.

Cells (ZR-75-1 breast carcinoma or H-1975 non-small cell lung carcinoma) were plated separately in 24-well plates for 24 hours prior to treatment with different peptides. The cells were then treated with 5 μM (final concentration) of different peptides every day for 4-6 days. On the day of termination, cells were washed two times with PBS and trypsinized with 0.3 ml of Trypsin/EDTA. Cell growth media was used to stop the trypsin reaction. Following washing, the cells were centrifuged and the cell pellets were re-suspended in PBS for counting in hemacytometer.

The trypan blue dye exclusion method was used to determine the number of viable cells present in a cell suspension. Cell suspension was mixed as 1:1 with the trypan blue dye and then visually examined in a hemacytometer. A viable cell will have a clear cytoplasm whereas a non-viable/dead cell will be stained with trypan blue dye. By doing this trypan blue exclusion method, viable cell numbers were counted and percent inhibition of proliferation was then calculated comparing with untreated controls.

Example 2

Results

Figure 2:
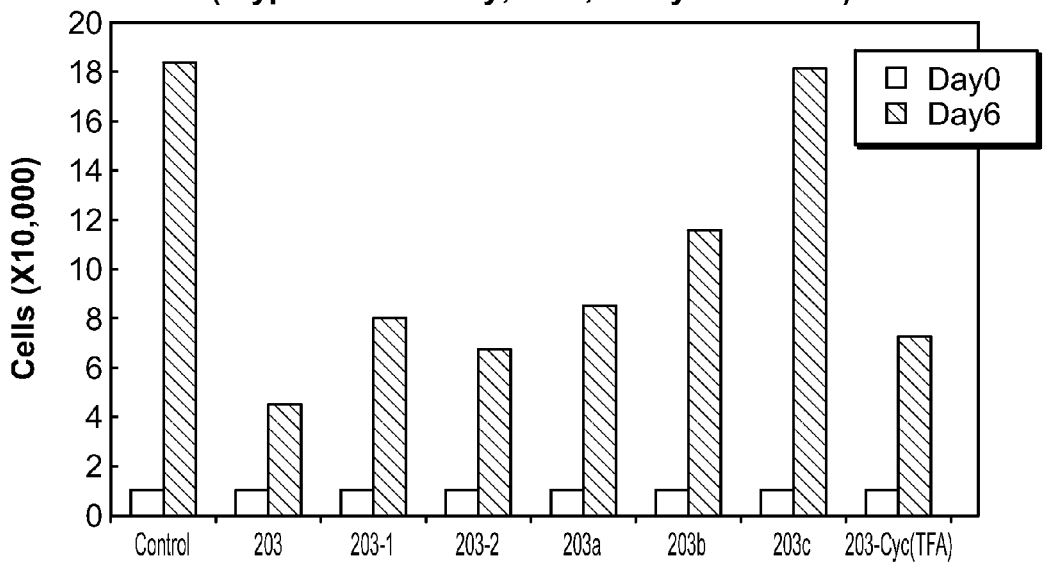
FIG. 2—Effect of CQC peptides on H1975 lung cancer cells. Graphic version of the peptide inhibition data from Table 2.
Figure 4:
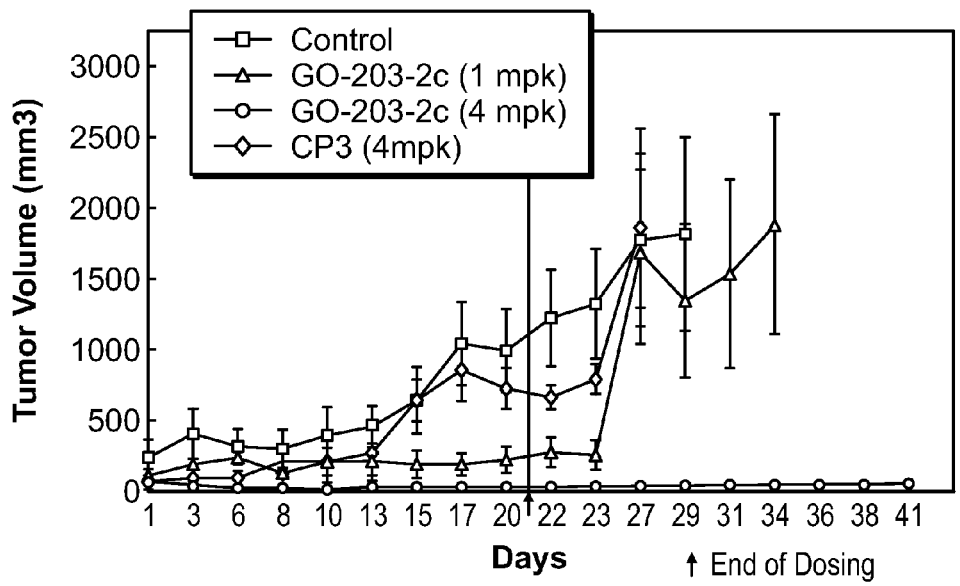
FIG. 4—Efficacy of GO-203-2c in a ZR-75-1 Human Breast Carcinoma Xenograft Model. Results are shown as mean±standard error of 5 mice per group.
Figure 5:
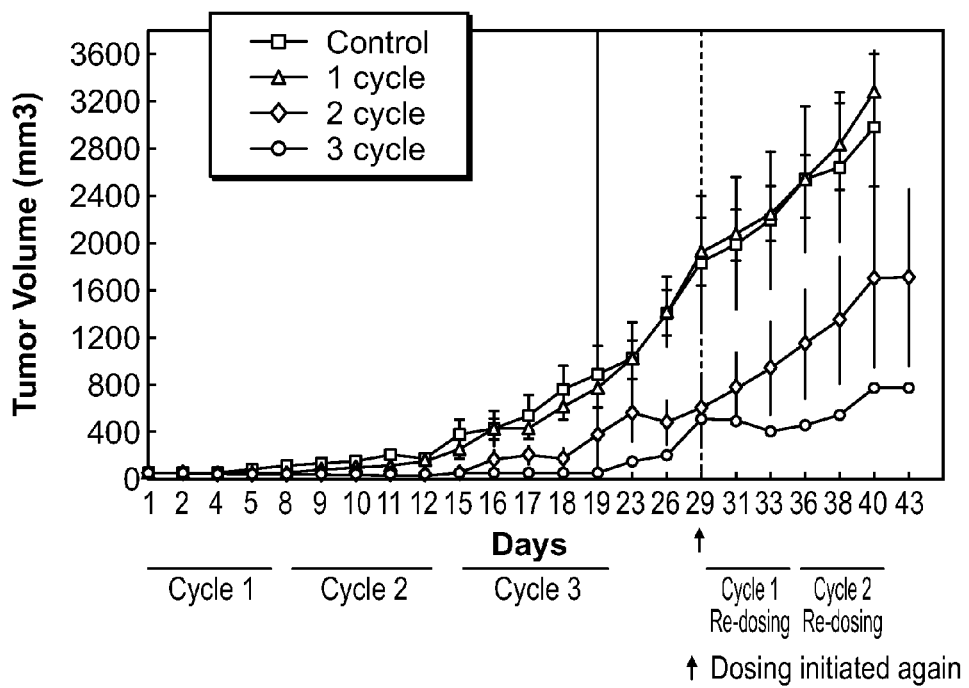
FIG. 5—Efficacy of GO-203-2c Using a 5 Days on/2 Days off IV Dosing Schedule for up to 3 Cycles in a ZR-75-1 Human Breast Carcinoma Xenograft Model. Results are shown as mean±standard error of eight mice per group. Group 4 mice with palpable tumors remaining after the third dosing cycle (N=5) received an additional 2 cycles of treatment beginning on Day 29.
Figure 6:
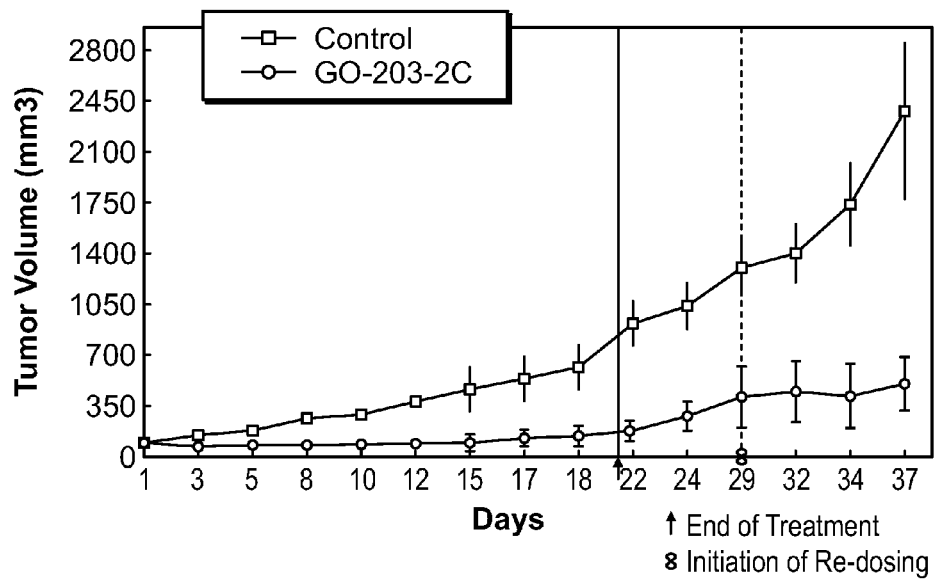
FIG. 6—Effect of GO-203-2c Treatment on MiaPaca Pancreatic Carcinoma Growth in Nude Mice. Results are shown as mean±standard error of eight mice per group. Daily dosing was resumed in group 2 mice after a one week interim period (on day 29) following the initial 21-day treatment period.
Figure 7:
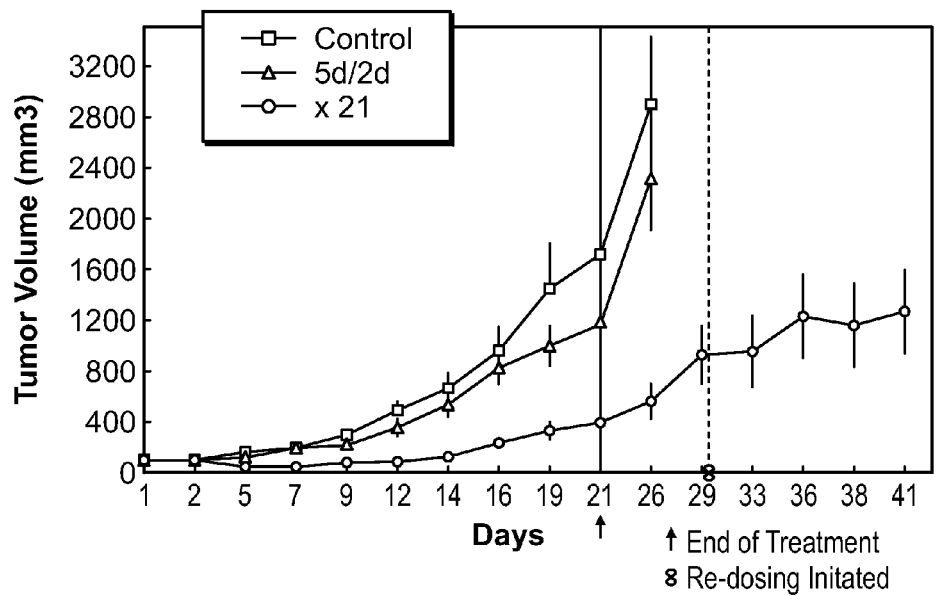
FIG. 7—Effect of GO-20-2c Treatment on A549 Non-Small Cell Lung Carcinoma Growth in Nude Mice. Results are shown as mean±SE of ten mice per group. Daily dosing was resumed in group 3 mice (N=5) after a one week interim period (on day 29) following the initial 21-day treatment period.
Figure 8:
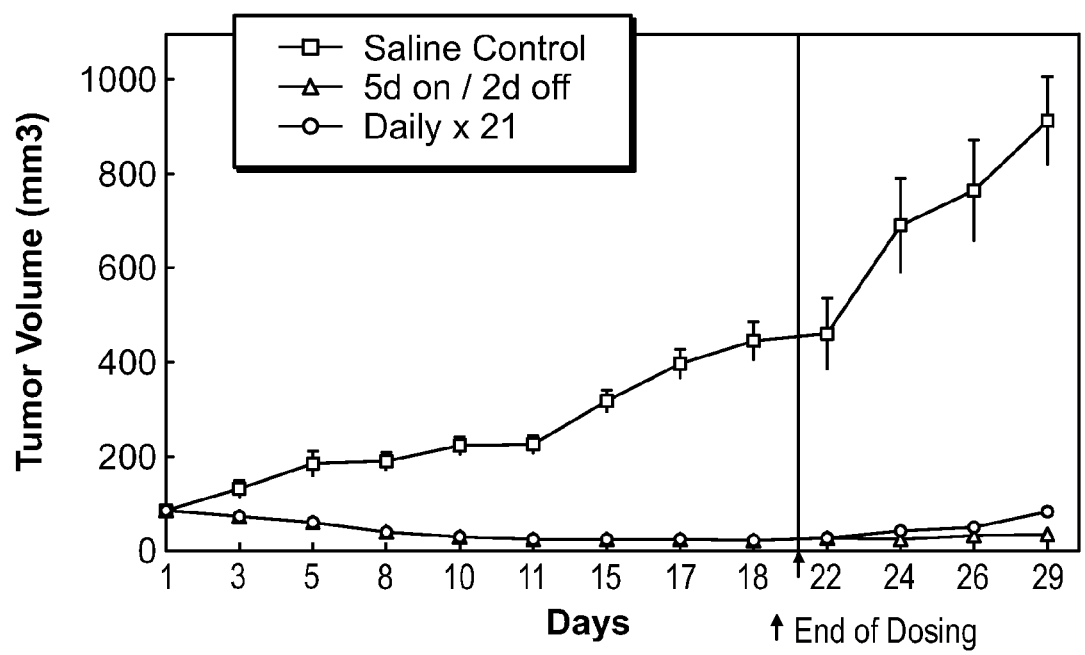
FIG. 8—Effect of GO-203-2c Treatment on PC3 Prostate Carcinoma Growth in Nude Mice. Results are shown as mean±SE of nine mice per group.
Figure 9:
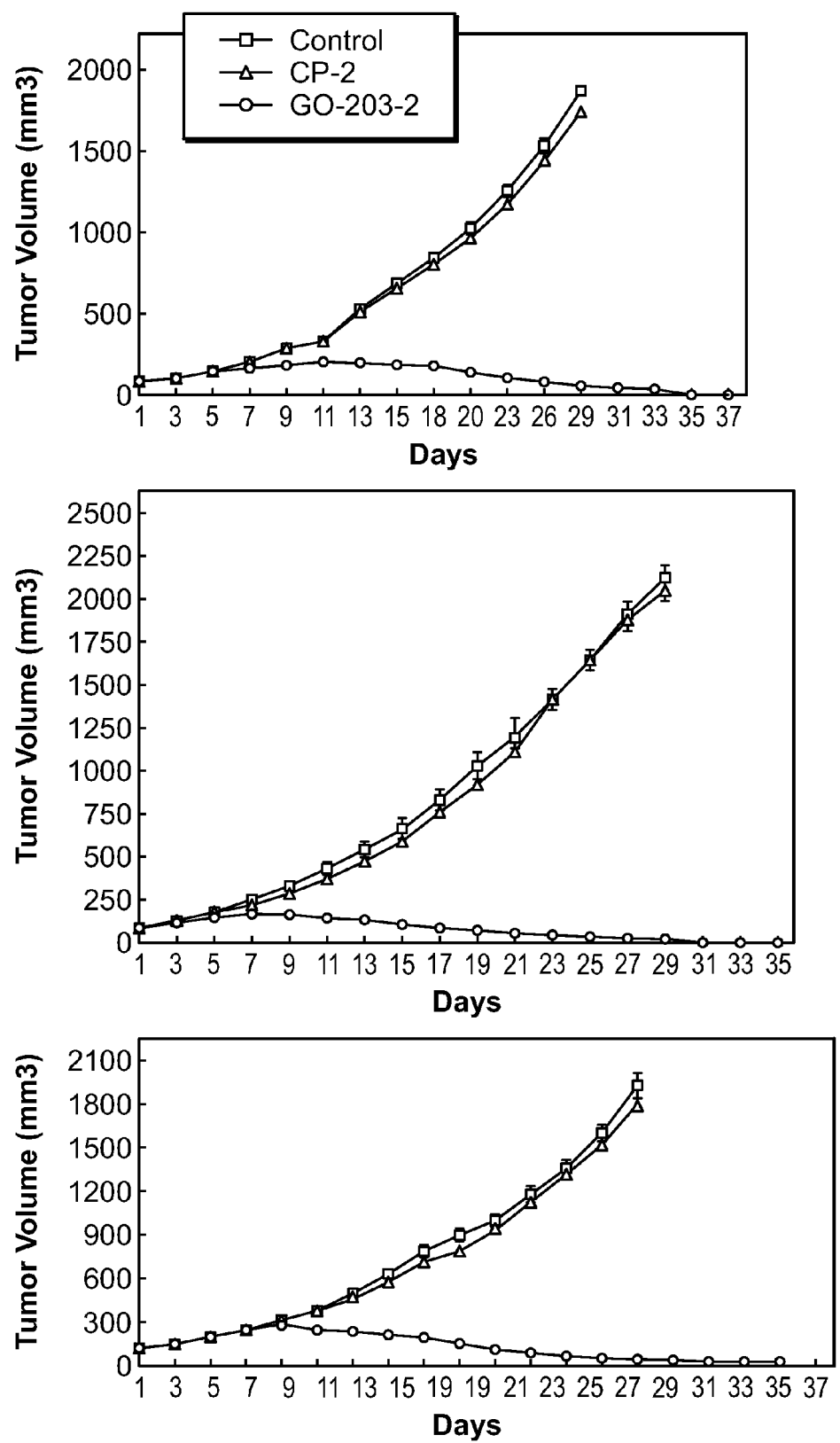
FIG. 9—Efficacy of GO-203-2 in Human COLO-205 Colon Carcinoma (top), MiaPaCa Pancreatic Carcinoma (middle) and SKOV3 Ovarian Carcinoma (bottom) Xenograft Models. Results are shown as mean±standard error of 8 mice per group.

The results of experiments following the methods described above a shown below in Table 1 and Table 2, and FIGS. 1 and 2, respectively. As can be seen in FIG. 3, the sequences of GO-203a, -203b and -203c do not have a full nine residue poly-Arg tail, but rather have 4 (3+1), 3 (2+1) and 2 (2+0) Arg residues added.

TABLE 1

ZR-75-1 Breast cancer cells 6-day treatment with CQC Peptides

|  | Group-1* | Group-2* | Group-3* | Avg | % inhibition |
|---|---|---|---|---|---|
| Control | 26.6 | 22.04 | 21.45 | 23.36 | — |
| GO-203 | 11.4 | 14.92 | 12.45 | 12.92 | 44.0 |
| GO-203a | 15.17 | 14.62 | 13.5 | 14.53 | 37.8 |
| GO-203b | 12.95 | 15.19 | 11.62 | 13.25 | 43.27 |
| GO-203c | 17.43 | 24.02 | 17.81 | 19.75 | 15.45 |
| GO-203-1 | 11.25 | 13.38 | 12.42 | 12.35 | 47.1 |
| GO-203-2 | 7.14 | 9.38 | 7.67 | 8.06 | 65.49 |
| GO-203-2c | 9.18 | 11.22 | 8.55 | 9.83 | 58.69 |

*Group 1-3 are individual wells, each having 10,000 cells

TABLE 2

H1975 Lung cancer cells cancer cells 6-day treatment with CQC Peptides

|  | Group-1* | Group-2* | Group-3* | Avg | % inhibition |
|---|---|---|---|---|---|
| Control | 18.27 | 18.04 | 18.68 | 18.32 | — |
| GO-203 | 4.42 | 5.48 | 3.43 | 4.44 | 75.76 |
| GO-203a | 8.01 | 8.98 | 8.58 | 8.52 | 53.47 |
| GO-203b | 12.75 | 10.0 | 11.8 | 11.51 | 37.13 |
| GO-203c | 16.87 | 19.87 | 17.54 | 18.09 | 1.24 |
| GO-203-1 | 8.64 | 7.36 | 8.39 | 8.13 | 55.62 |
| GO-203-2 | 6.23 | 6.34 | 7.42 | 6.66 | 63.64 |
| GO-203-2c | 8.47 | 7.13 | 6.02 | 7.2 | 60.7 |

*Group 1-3 are individual wells, each having 10,000 cells

Example 3

Cyclized Peptide GO-203-2c

A series of in vitro and in vivo primary pharmacodynamic studies was conducted to assess efficacy and mechanism of action of GO-203-2c in human tumor cells. GO-203-2c, and the reduced form of the molecule, GO-203-2, inhibited proliferation of a variety of human carcinoma cell lines in vitro, with 50% inhibition ($IC_{50}$) occurring at concentrations of approximately 2 to 5 µM (5 to 11 µg/ml). In a ZR-75-1 human breast carcinoma xenograft model, intravenous (IV) treatment with GO-203-2c at 4 mg/kg daily for 21 consecutive days resulted in complete regression of established subcutaneous (SC) tumors in nu/nu mice. Treatment with 1 mg/kg GO-203-2c was associated with partial tumor regression in the model. Similarly, in a MiaPaCa human pancreatic carcinoma xenograft model, daily IV treatment with GO-203-2c (10 mg/kg) for 21 consecutive days resulted in significant arrest of tumor growth, with 2 of 8 mice tumor-free at the end of treatment. In both in vitro and in vivo studies, a control peptide (CP-3), containing AQA instead of CQC amino acid sequence in the binding domain, was ineffective at inhibiting proliferation of tumor cells, demonstrating requirement of the CQC sequence for anti-tumor activity of the peptide.

In studies comparing different dosing schedules of GO-203-2c, daily IV administration for 21 consecutive days was shown to be more effective than a 5-day on, 2-day off×3 cycle schedule in human breast carcinoma (ZR-75-1) and human non-small cell lung carcinoma (NSCLC; A549) models. The 5-day on, 2-day off×3 cycle schedule resulted in tumor growth arrest during the treatment period, but the tumors resumed growth either near the end or after cessation of treatment. In contrast, in a PC3 human prostate carcinoma xenograft model, the 2 different dosing schedules were equally effective, and GO-203-2c treatment using either schedule resulted in complete growth arrest and regression of tumors.

Additional in vivo studies using the reduced form GO-203-2 and daily intraperitoneal (IP) administration for 28 consecutive days also demonstrated complete tumor growth arrest and regression after continuous daily dosing, and extend the findings to human colon (COLO-205) and human ovarian (SKOV3) carcinomas. Therefore, GO-203-2c and the reduced form GO-203-2 have been shown to be effective at inhibiting tumor cell growth in vitro and in vivo in a variety of human solid tumors.

Studies to confirm mechanism of action of GO-203-2c demonstrated inhibition of Mucin 1 (MUC1) oncoprotein cytoplasmic domain (MUC1-CD) oligomerization in HEK 293T cells transfected with human GFP- and Flag-tag versions of MUC1-CD. However, in studies using purified His-tagged MUC1-CD proteins in a cell-free system, GO-203-2 was much more effective at inhibiting MUC1-CD oligomerization than the oxidized form, GO-203-2c, suggesting that GO-203-2c must be converted to GO-203-2 in the highly reductive intracellular environment (Hansen et al., 2009) in order for the molecule to interact with MUC1-CD. This finding is not surprising based on a requirement for the cysteine residues in the GO-203-2 binding domain (CQCRRKN) to be available for binding with cysteine residues on the corresponding binding domain of the MUC1-CD protein.

Studies were also conducted to confirm pharmacological relevance of the rodent and nonrodent species chosen for toxicology studies, namely the rat and dog, respectively. MUC1-CD amino acid sequence was determined to be greater than 80% identical between rat, dog and human proteins, and similar expression of MUC1 was found in stomach, intestinal and lung epithelium from the different species using immunohistochemical staining. GO-203-2 inhibited oligomerization of purified His-tagged MUC1-CD in a cell-free system, and GO-203-2 and GO-203-2c inhibited MUC1-CD oligomerization in cell-based systems (transfected HEK 293T cells) in an equivalent manner when MUC1-CD oncoproteins from the different species were compared. The results of these studies indicate that potential MUC1-CD targets in the rat, dog and human are similar with respect to sequence, tissue expression and responsiveness to inhibition of oligomerization by GO-203-2c, and confirm pharmacological relevance of the species chosen for nonclinical safety assessment of GO-203-2c.

In receptor binding screens evaluating the potential for secondary pharmacological effects of GO-203-2 and GO-203-2c, both molecules significantly inhibited radioligand binding to the following targets: adrenergic $\alpha_{1A}$ and $\alpha_{1B}$ receptors, norepinephrine transporter, muscarinic $M_2$ receptor and nicotinic acetylcholine $\alpha 1$ (bungarotoxin) receptor, with $IC_{50}$ values ranging from approximately 3 to 8 µM. In addition, GO-203-2c significantly inhibited radioligand binding to dopamine $D_1$ receptor ($IC_{50}$ of 10.5 µM). The control AQA-containing peptide CP-3 also significantly inhibited radioligand binding in the norepinephrine transporter (79% inhibition) and muscarinic $M_2$ receptor (55% inhibition) assays at a concentration of 10 µM, suggesting that the findings for the GO-203-2 and GO-203-2c peptides in these assays may be nonspecific, i.e., not related to specific binding at the CQCRRKN binding motif. Follow-up studies to characterize the functional consequence of binding of GO-203-2c and/or GO-203-2 to the various targets were not conducted.

In light of the intended Phase 1 patient population, no formal safety pharmacology studies have been conducted with GO-203-2c in support of the proposed Phase 1 clinical trial. This proposal is consistent with the ICH S9 guideline which indicates that stand-alone safety pharmacology studies need not be conducted to support studies in patients with late stage cancer or advanced disease. Moreover, results from the toxicology studies did not identify a need for follow-up safety pharmacology testing.

No pharmacodynamic drug interaction studies have been conducted with GO-203-2c. The primary pharmacodynamic data included in this submission indicate that GO-203-2c is active as a single agent. The Sponsor proposes to begin the clinical development of GO-203-2c as a single agent for the treatment of solid tumors.

In summary, GO-203-2c has been demonstrated to inhibit proliferation of a variety of human carcinoma cells in vitro and in human tumor xenograft models. Mechanism of action is associated with inhibition of MUC1-CD oligomerization in the tumor cells, presumably resulting in decreased translocation of MUC1-C terminal (MUC1-C ter) to the nucleus, increase in intracellular reactive oxygen species (ROS) levels, activation of the DNA damage response, S phase arrest, loss of cell membrane integrity and cellular necrosis/apoptosis, as has been demonstrated previously in studies using a longer length peptide from the same series (Raina et al., 2009; Joshi et al., 2009; Yin et al., 2010).

Primary Pharmacodynamics: In Vitro Inhibition of Tumor Cell Proliferation by GO-203-2 and GO-203-2c.

GO-203-2 and GO-203-2c were evaluated for ability to inhibit proliferation of murine and human carcinoma cell lines in vitro. Test compound (5 µM final concentration) was added to tumor cell cultures daily for 5 to 6 days, and cell viability was determined by trypan blue dye exclusion. Results are summarized in Table 3. Treatment of all cell lines with 5 µM GO-203-2 or GO-203-2c resulted in significant inhibition of proliferation, and the two forms of the compound (reduced and oxidized) were approximately equivalent in activity. The control peptide CP-3, which has alanine amino acids substituted for the cysteine amino acids in the binding domain of the parent molecule, had minimal effect on tumor cell proliferation (data not shown).

TABLE 3

Inhibition of Proliferation of Murine and Human Tumor Cells by GO-203-2 and GO-203-2c (5 µM)

| Tumor Cell Type | % Inhibition | |
|---|---|---|
| | GO-203-2 | GO-203-2c |
| Mouse | | |
| KW-814 T6 NSCLC | NT | 70.1 |
| KW-807 LN NSCLC | NT | 40.3 |
| Human | | |
| ZR-75-1 breast carcinoma | 50.7 | 43.6 |
| MCF-7 breast carcinoma | 91.4 | 87.7 |
| H1975 NSCLC | 52.9 | 46.2 |
| H1650 NSCLC | NT | 89.0 |
| A549 NSCLC | 75.4 | 73.1 |
| MiaPaCa-2 pancreatic carcinoma | NT | 81.5 |

NSCLC = non-small cell lung carcinoma; NT = not tested
Results are % inhibition of cell viability on Day 6-7 compared to control (untreated) cells Studies to confirm mechanism of action of GO-203-2c demonstrated inhibition of MUC1-CD oligomerization in HEK 293T cells transfected with human MUC1-CD. However, in studies using purified His-tagged MUC1-CD proteins in a cell-free system, GO-203-2 was much more effective at inhibiting MUC1-CD oligomerization than the oxidized form, GO-203-2c, suggesting that GO-203-2c must be converted to GO-203-2 in the highly reductive intracellular environment (Hansen, 2009) in order for the molecule to interact with MUC1-CD. This finding is not surprising based on a requirement for the cysteine residues in the GO-203-2 binding domain (CQCRRKN) to be available for binding with cysteine residues on the corresponding binding domain of the MUC1-C protein.

Efficacy of GO-203-2c was evaluated in a ZR-75-1 human breast carcinoma xenograft model. Female nu/nu mice (20-30 g; Charles River Laboratories, Wilmington, Mass.) were injected in the thigh with 5 million ZR-75-1 cells in Matrigel suspension. Mice also received subcutaneous 17-β-estradiol pellets. When tumors reached 100-200 mm³ in size (approximately 12-15 days after implantation), mice were split into 4 groups of 5 mice and administered the following treatments daily for 21 days: phosphate-buffered saline (PBS) IP, 1 mg/kg GO-203-2c IV, 4 mg/kg GO-203-2c IV or 4 mg/kg control peptide CP-3 IV. Each animal was sacrificed when the tumor reached the predetermined endpoint size (~2500 mm³) or when the animals remained tumor-free for 180 days after implantation of the tumor cells.

Partial tumor regression was observed after treatment with 1 mg/kg GO-203-2c, with tumor growth occurring after discontinuation of the treatment. However, in mice treated with 4 mg/kg GO-203-2c, there was complete regression of tumor growth and tumors were no longer palpable after approximately 3 weeks of treatment. Treatment with CP3 or PBS vehicle control had no effect on tumor growth.

In a second study using this ZR-75-1 cell xenograft model, a 5 days on/2 days off IV dosing schedule was used, and groups of 8 mice received either one, two or three cycles utilizing this schedule. Mice administered 7.5 mg/kg GO-203-2c for one dosing cycle (5 days on/2 days off) showed partial tumor regression during the treatment period. Tumor growth was cytostatic for 4-5 days after stopping the drug treatment, but tumors subsequently started re-growing similarly to control. Tumor regression was also observed over the treatment period for animals received 2 dosing cycles, with tumor growth resuming 4-5 days after cessation of treatment in 6 of 8 mice. Two of 8 mice were completely cured following 2 cycles of treatment and tumor did not re-grow after cessation of dosing. In mice that received 3 dosing cycles, there was substantial regression of tumors during the treatment period. Three of 8 mice receiving 3 dosing cycles were completely cured and tumor did not re-grow after cessation of dosing. Tumors in the remaining 5 of 8 mice in this group started re-growing at 8+ days after cessation of treatment. These animals were administered an additional 2 cycles of treatment, starting on Day 29. Following re-dosing, the tumors were somewhat stabilized with very slow growth during the additional treatment period.

Male BALB/c nu/nu mice (8 weeks old; Charles River Laboratories, Wilmington, Mass.) were injected with 2.5 million MiaPaCa cells in the right thigh. When tumors reached a predetermined size (approximately 100 mm$^3$; 34 days after tumor cell implantation), mice (8 per group) were administered normal saline (control) or GO-203-2c (10 mg/kg) IV daily for 21 consecutive days. At the end of the treatment period, and following a one week interim period, animals that received GO-203-2c initially were administered an additional series of GO-203-2c daily injections.

Daily IV treatment resulted in MiaPaCa tumor growth delay by 8 days of treatment. Two out of 8 mice were tumor free as early as the 10th day of treatment. However, the tumors in the remaining 6 mice started growing steadily albeit very slowly after cessation of dosing. During the 7-day rest period, tumors in these 6 mice approximately tripled in size. To further define the activity of GO-203-2c on palpable tumors that remained in the six GO-203-2c-treated mice, another cycle of daily IV dosing with 10 mg/kg GO-203-2c was initiated on day 29, when tumors had an average size of ~400 mm$^3$. Following re-dosing, the tumors were somewhat stabilized, with a very slow growth compared to that of tumors in the saline control group.

Male BALB/c nu/nu mice (6-7 weeks old; Charles River Laboratories, Wilmington, Mass.) were injected with 5 million A549 or PC3 cells in the right thigh. When tumors reached a predetermined size (approximately 80-100 mm$^3$; 10-16 days after tumor cell implantation), treatment was initiated as follows: Group 1, saline control (daily×21 days); Group 2, GO-203-2c (7.5 mg/kg, 5 days on/2 days off×3 cycles); Group 3, GO-203-2c (7.5 mg/kg, daily×21 days). In the A549 study, Group 3 animals that still had palpable/measurable tumors at the end of the 21-day treatment period were administered an additional 9 days of GO-203-2c treatment (Group 3'), with a one week interim period between treatments.

In the A549 model, tumor growth delays were observed initially using both dosing schedules. However, tumors in mice treated with the 5 days on/2 days off schedule started growing steadily after day 9. Daily treatment for 21 consecutive days slowed down tumor growth substantially during the treatment period as compared to the saline treated group. During the 7 days of rest period after cessation of dosing in animals receiving the continuous daily dosing schedule, the tumors doubled in size, such that the average tumor size was ~900 mm$^3$ on day 29 at the start of re-dosing. Following re-dosing, tumor growth was somewhat stabilized with a very slow growth during the treatment period.

In the PC3 model, tumor growth was immediately arrested and tumors regressed with both GO-203-2c treatment schedules. Therefore, both treatment schedules were found to be approximately equally effective in this PC3 prostate carcinoma xenograft model.

Efficacy of GO-203-2, the reduced form of GO-203-2c that is responsible for binding to and inhibiting oligomerization of MUC1-CD was evaluated in several different human tumor xenograft models. For these studies BALB/c nu/nu mice (6-7 weeks old; Charles River Laboratories, Wilmington, Mass.) were injected with 10 million COLO-205 colon carcinoma, MiaPaCa pancreatic carcinoma or SKOV3 ovarian carcinoma cells in the right thigh. When tumors reached a predetermined size (80-125 mm$^3$), mice were randomized into groups of 8 animals and treatment was initiated, which consisted of daily IP injection of GO-203-2 (30 mg/kg), control peptide CP-2 (30 mg/kg) or PBS vehicle control for 28 days. Mice with tumors in excess of ~2 g or with ulcerated tumors were euthanized, as were those found in obvious distress or in a moribund condition. Mice without palpable tumors were maintained until 90 to 100 days after treatment initiation to confirm lack of re-growth. In addition, animals were weighed periodically during the treatment period and examined for clinical signs of toxicity. There were no observable side effects of treatment with the two peptides.

Treatment with 30 mg/kg GO-203-2 daily for 28 days resulted in complete growth arrest and regression of COLO-205, MiaPaCa and SKOV3 tumors implanted in nude mice. Treatment with control peptide CP-2, which has alanine residues substituted for cysteine residues in the binding domain, was without effect. There was no evidence of recurrence of tumors in mice treated with GO-203-2 up to 90 to 100 days post treatment initiation. These results confirm efficacy of the active, reduced form of GO-203-2c in human tumor xenograft models, and extend the findings to include several different tumor types (i.e., colon and ovarian carcinomas) that were not studied with GO-203-2c.

Studies were also conducted to confirm pharmacological relevance of the rodent and nonrodent species chosen for toxicology studies, namely the rat and dog, respectively. MUC1-CD amino acid sequence was determined to have greater than 80% sequence identity between rat, dog and human proteins, and similar expression of MUC1 was found in stomach, intestinal and lung epithelium from the different species using immunohistochemical staining. GO-203-2 inhibited oligomerization of purified His-tagged MUC1-CD in a cell-free system, and GO-203-2 and GO-203-2c inhibited MUC1-CD oligomerization in cell-based systems (transfected HEK 293T cells) in an equivalent manner when MUC1-CD from the different species was compared. The results of these studies indicate that potential MUC1-CD targets in the rat, dog and human are similar with respect to sequence, tissue expression and responsiveness to inhibition of oligomerization by GO-203-2c and GO-203-2, and confirm pharmacological relevance of the species chosen for nonclinical safety assessment of GO-203-2c.

In receptor binding screens evaluating the potential for secondary pharmacological effects of GO-203-2 and GO-203-2c, both molecules significantly inhibited radioligand binding to the following targets: adrenergic α1A and α1B receptors, norepinephrine transporter, muscarinic M2 receptor and nicotinic acetylcholine α1 (bungarotoxin) receptor, with IC$_{50}$ values ranging from approximately 3 to 8 μM. In addition, GO-203-2c significantly inhibited radioligand binding to dopamine D1 receptor (IC$_{50}$ of 10.5 μM). The control AQA-containing peptide CP-3 also significantly inhibited radioligand binding in the norepinephrine transporter (79% inhibition) and muscarinic M2 receptor (55% inhibition) assays at a concentration of 10 μM, suggesting that the findings for the GO-203-2 and GO-203-2c peptides in these assays may be nonspecific, i.e., not related to specific binding at the Cys-Gln-Cys-Arg-Arg-Lys-Asn binding motif.

Follow-up studies to characterize the functional consequence of binding of GO-203-2c and/or GO-203-2 to the various targets were not conducted.

In light of the intended Phase 1 patient population, no formal safety pharmacology studies have been conducted with GO-203-2c in support of the proposed Phase 1 clinical trial. This proposal is consistent with the ICH S9 guideline which indicates that stand-alone safety pharmacology studies need not be conducted to support studies in patients with late stage cancer or advanced disease. Moreover, results from the toxicology studies did not identify a need for follow-up safety pharmacology testing.

No pharmacodynamic drug interaction studies have been conducted with GO-203-2c. The primary pharmacodynamic data included in this submission indicate that GO-203-2c is active as a single agent. The Sponsor proposes to begin the clinical development of GO-203-2c as a single agent for the treatment of solid tumors.

The proposed clinical trial will be a multicenter, open-label, dose-escalation, safety, pharmacodynamic and pharmacokinetic study in patients with advanced solid tumors administered GO-203-2c IV over 60 min once per day for 21 consecutive days; this dosing regimen will be repeated every 28 days. Since the majority of the treatment-related findings in rats and dogs were localized at the infusion site or were secondary to the infusion site reactions, the no-observed-adverse-effect-level (NOAEL) for systemic toxicity in the pivotal repeat-dose rat toxicity study was determined to be 5 mg/kg/day. The highest non-severely toxic dose (HNSTD), which was also considered the NOAEL, was established as 1 mg/kg/day in the dog pivotal repeat-dose toxicity study. For vascular injury at the injection site, the NOAEL in rats is 20.8 m/mL/min. This concentration rate is 25-fold greater than the estimated concentration rate for humans (0.83 μg/mL/min) at the recommended starting dose of 3 mg/m2/day (assumes a body mass of 1.65 m2).

The estimated starting dose for the upcoming clinical trial was based on the ICH guideline, S9: Nonclinical Evaluation for Anticancer Pharmaceuticals. A severely systemic toxic dose (STD) in 10% of the animals was not established in the pivotal repeat-dose toxicity study in rats, therefore the rat NOAEL of 30 mg/m2/day (5 mg/kg/day) was used to calculate the safe human starting dose of 3 mg/m2/day (1/10 of NOAEL). This calculated starting dose was less than 1/6 of the dog 1-INSTD or NOAEL (20 mg/m2/day; 1 mg/kg/day). The calculation for the recommended human starting dose is:

1/10 of rat systemic NOAEL of 30 $mg/m^2$/day (highest dose)=3 $mg/m^2$/day

1/6 of dog highest non-severely toxic dose (HNSTD or NOAEL) of 20 $mg/m^2$/day=3.3 $mg/m^2$/day Safety margins, based on dose (mg/kg and mg/m2), for the proposed human starting dose are presented in Table 2.4.5-1. The NOAEL for rats and dogs in the repeat-dose studies was 5 mg/kg/day (30 $mg/m^2$/day) and 1 mg/kg/day (20 $mg/m^2$/day), respectively. The proposed 3 $mg/m^2$ human starting dose is 12- and 62-fold lower than the NOAELs in the dog and rat repeat-dose toxicity studies, respectively, based on a mg/kg basis and 6.7- and 10-fold lower, respectively, based on $mg/m^2$.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VIII. References

The following references, to the extent that they provide exemplary procedural or other details supplementary to those set forth herein, are specifically incorporated herein by reference:

U.S. Pat. No. 5,250,564
U.S. Pat. No. 5,264,419
U.S. Pat. No. 5,288,707
U.S. Pat. No. 5,440,013
U.S. Pat. No. 5,446,128
U.S. Pat. No. 5,475,085
U.S. Pat. No. 5,550,251
U.S. Pat. No. 5,552,534
U.S. Pat. No. 5,596,078
U.S. Pat. No. 5,597,457
U.S. Pat. No. 5,616,684
U.S. Pat. No. 5,618,914
U.S. Pat. No. 5,633,345
U.S. Pat. No. 5,633,346
U.S. Pat. No. 5,670,155
U.S. Pat. No. 5,672,681
U.S. Pat. No. 5,674,976
U.S. Pat. No. 5,710,245
U.S. Pat. No. 5,723,575
U.S. Pat. No. 5,726,287
U.S. Pat. No. 5,770,732
U.S. Pat. No. 5,790,421
U.S. Pat. No. 5,801,148
U.S. Pat. No. 5,807,829
U.S. Pat. No. 5,811,387
U.S. Pat. No. 5,811,512
U.S. Pat. No. 5,811,515
U.S. Pat. No. 5,817,879
U.S. Pat. No. 5,840,833
U.S. Pat. No. 5,859,184
U.S. Pat. No. 5,861,380
U.S. Pat. No. 5,869,455
U.S. Pat. No. 5,877,578
U.S. Pat. No. 5,889,155
U.S. Pat. No. 5,929,237
U.S. Pat. No. 5,939,268
U.S. Pat. No. 5,939,383
U.S. Pat. No. 5,965,695
U.S. Pat. No. 5,990,273
U.S. Pat. No. 6,093,573
U.S. Pat. No. 6,117,974
U.S. Pat. No. 6,184,345
U.S. Pat. No. 6,197,963
U.S. Pat. No. 6,261,569
U.S. Pat. No. 6,420,339
U.S. Pat. No. 6,436,697
U.S. Pat. No. 6,552,170
U.S. Pat. No. 6,566,493
U.S. Pat. No. 6,569,993
U.S. Pat. No. 6,593,292

U.S. Pat. No. 6,664,372
U.S. Pat. No. 6,706,862
U.S. Pat. No. 6,818,659
U.S. Pat. No. 6,846,805
U.S. Pat. No. 6,946,542
U.S. Pat. No. 7,166,568
U.S. Pat. No. 7,183,059
U.S. Pat. No. 7,192,713
U.S. Pat. No. 7,202,332
U.S. Pat. No. 7,247,701
U.S. Pat. No. 7,576,057
U.S. Pat. No. 7,587,286
U.S. Pat. No. 7,589,170
U.S. Pat. No. 7,610,156
U.S. Pat. No. 7,666,400
U.S. Pat. No. 7,705,012
U.S. Pat. No. 7,705,118
U.S. Pat. No. 7,718,598
U.S. Pat. No. 7,863,239
U.S. Prov. Appln. 61/253,730
U.S. Patent Appln. 2003/0187188
U.S. Patent Appln. 2005/0015232
U.S. Patent Appln. 2005/0043509
Abe and Kufe, *Cancer Res.*, 49(11):2834-2839, 1989.
Ahmad et al., *J. Biol. Chem.*, 281:35764-9, 2006.
Ahmad et al., *Nat. Cell Biol.*, 9:1419-1427, 2007.
Baldus et al., *Clin. Cancer Res.*, 10(8):2790-2796, 2004.
Bodanszky et al., *J. Antibiot.*, 29(5):549-53, 1976.
Cohen et al., *J. Med. Chem.*, 33:883-894, 1990.
Dintzis et al., *Proteins*, 16(3):306-8, 1993.
Duraisamy et al., *Gene*, 373:28-34, 2006.
Fischer, *Med. Res. Rev.*, 27(6):755-796, 2007.
Flynn, In: *Percutaneous Absorption: Mechanisms-Methodology-Drug Delivery*, 27-53, 1985.
Gendler et al., *J. Biol. Chem.*, 263:12820-12823, 1988.
Goldstein et al., *Scientific American*, 255:74-83, 1986.
Gronenborn et al., *Anal. Chem.*, 62(1):2-15, 1990.
Guichard et al., *Pept. Res.*, 7(6):308-21, 1994.
Hamamoto et al., *Microbiol. Immunol.*, 46(11):741-9, 2002.
Hansen et al., *J. Clin. Oncol.*, 27(28):4679-84, 2009.
Hodel et al., *Mol. Cell*, 10(2):347-58, 2002.
Huang et al., *Cancer Biol Ther.*, 2:702-706, 2003.
Huang et al., *Cancer Res.*, 65:10413-10422, 2005.
Jackson, *Seminars in Oncology*, 24:L164-172, 1997.
Johnson et al., In: *Biotechnology And Pharmacy*, Pezzuto et al. (Eds.), Chapman and Hall, NY, 1993.
Jones et al., *Br. I Pharmacol.*, 145(8):1093-102, 2005.
Jones et al., *J. Med. Chem.*, 39:904-917, 1996.
Joshi et al., *Mol. Cancer. Ther.*, 8(11):3056-65, 2009
Kau et al., *Nat. Rev. Cancer*, 4(2):106-17, 2004.
Kinlough et al., *J. Biol. Chem.*, 279(51):53071-53077, 2004.
Kufe et al., *Hybridoma*, 3:223-232, 1984.
Leng et al., *J. Biol. Chem.*, 282:19321-19330, 2007.
Levitan et al., *J. Biol. Chem.*, 280:33374-33386, 2005.
Li et al., *Cancer Biol. Ther.*, 2:187-193, 2003b.
Li et al., *J. Biol. Chem.*, 276:35239-35242, 2001.
Li et al., *J. Biol. Chem.*, 276:6061-6064, 2001.
Li et al., *Mol. Cancer. Res.*, 1:765-775, 2003c.
Li et al., *Mol. Cell. Biol.*, 18:7216-7224, 1998.
Li et al., *Oncogene*, 22:6107-6110, 2003a.
Ligtenberg et al., *J. Biol. Chem.*, 267, 6171-6177, 1992.
Macao, *Nat. Struct. Mol. Biol.*, 13, 71-76, 2006.
McPherson, *J. Biol. Chem.*, 251:6300-6306, 1976.
Merlo et al., *Cancer Res.*, 49, 6966-6971, 1989.
Merrifield, *J. Am. Chem. Soc.*, 85:2149-2154, 1963.
Navia et al., *Curr. Opin. Struct. Biol.*, 2:202-210, 1992.
Pardridge, *Endocrin. Rev.*, 7:314-330, 1986.
PCT Appln. PCT/US00/03745
PCT Appln. PCT/US00/14667
PCT Appln. PCT/US99/11913
PCT Appln. PCT/US99/18441
Peptide Synthesis, 1985
Percipalle et al., *J. Mol. Biol.*, (4):722-32, 1997.
Perey et al., *Cancer Res.*, 52(22):6365-6370, 1992.
Protective Groups in Organic Chemistry, 1973
Protein NMR Spectroscopy, Principles and Practice, Cavanagh et al., Academic Press, San Diego, 1996.
Raina et al., *Cancer Res.*, 69(12):5133-41, 2009.
Raina et al., *EMBO J.*, 25:3774-3783, 2006.
Raina et al., *J. Biol. Chem.*, 279:20607-20612, 2004.
Ramasamy et al., *Mol. Cell*, 27:992-1004, 2007.
Remington's Pharmaceutical Sciences, 15$^{th}$ Ed., 1035-1038 and 1570-1580, 1990.
Remington's Pharmaceutical Sciences, 15$^{th}$ Ed., 33:624-652, 1990.
Ren et al., *Cancer Cell*, 5:163-175, 2004.
Ren et al., *J. Biol. Chem.*, 277:17616-17622, 2002.
Ryan and Wente, *Curr. Opin. Cell Biol.*, 12(3):361-71, 2000.
Schafmeister et al., *J American Chem Soc*, 122(24): 5891-5892, 2000.
Schroeder et al., *J. Biol. Chem.*, 276(16):13057-13064 2001.
Schroeder et al., *Oncogene*, 23:5739-5747, 2004.
Siddiqui et al., *Proc. Natl. Acad. Sci. USA*, 85:2320-2323, 1988.
Solid Phase Peptide Synthelia, 1984
Suh and Gumbiner, *Exp. Cell Res.*, 290(2):447-56, 2003.
Truscott et al., *J. Cell Biol.*, 163(4):707-713, 2003.
Vermeer et al., *Nature*, 422(6929):322-6, 2003.
Weber, *Advances Protein Chem.*, 41:1-36, 1991.
Wei et al., *Cancer Cell*, 7:167-178, 2005.
Weis, *Cell*, 112(4):441-51, 2003.
Wen et al., *J. Biol. Chem.*, 278:38029-38039, 2003.
Wider, *Bio Techniques*, 29:1278-1294, 2000.
Yamamoto et al., *J. Biol. Chem.*, 272:12492-12494, 1997.
Yin et al., *Cancer Biol. Ther.*, 10(5):483-91, 2010.
Yin et al., *J. Biol. Chem.*, 278:35458-35464, 2003.
Yin et al., *J. Biol. Chem.*, 279:45721-45727, 2004.
Yin et al., *J. Biol. Chem.*, 282:257-266, 2007.
Young et al., *Cell.* 112(1):41-50, 2003.

What is claimed is:

1. A method of inhibiting a MUC1-positive cancer cell comprising contacting the MUC1-positive cancer cell with a MUC1 peptide of 50 residues or less and comprising at least 4 consecutive MUC1 residues and no more than 20 consecutive MUC1 residues and comprising the sequence CQC, wherein:
(i) the amino-terminal cysteine of CQC is covered on its NH2-terminus by at least one amino acid residue that need not correspond to the native MUC1 transmembrane sequence; and
(ii) the peptide comprises 3-5 consecutive positively-charged amino acid residues in addition to those positively-charged amino acid residues corresponding to native MUC1 residues.

2. The method of claim 1, wherein the peptide comprises at least 5, 6 or 7 consecutive MUC1 residues.

3. The method of claim 2, wherein the sequences comprise CQCR (SEQ ID NO:1), CQCRR (SEQ ID NO:2), CQCRRR (SEQ ID NO:3), CQCRRRR (SEQ ID NO:4), CQCRRK (SEQ ID NO:5), or CQCRRKN (SEQ ID NO:6).

4. The method of claim 1, wherein the peptide contains no more than 10 consecutive residues, 11 consecutive residues, 12 consecutive residues, 13 consecutive residues, 14 consecutive residues, 15 consecutive residues, 16 consecutive residues, 17 consecutive residues, 18 consecutive residues or 19 consecutive residues of MUC1.

5. The method of claim 1, wherein the MUC1-positive cell is a solid tumor cell.

6. The method of claim 5, wherein the solid tumor cell is a lung cancer cell, a brain cancer cell, a head & neck cancer cell, a breast cancer cell, a skin cancer cell, a liver cancer cell, a pancreatic cancer cell, a stomach cancer cell, a colon cancer cell, a rectal cancer cell, a uterine cancer cell, a cervical cancer cell, an ovarian cancer cell, a testicular cancer cell, a skin cancer cell or a esophageal cancer cell.

7. The method of claim 1, wherein the 3-5 positively-charged residues are located at the C-terminus of the peptide.

8. The method of claim 1, where the MUC1-positive cell is a leukemia or myeloma cell.

9. The method of claim 8, wherein the cell is a acute myeloid leukemia, chronic myelogenous leukemia or multiple myeloma.

10. The method of claim 1, wherein the peptide comprises 1, 2, 3 or 4 positively-charged amino acid residues corresponding to native MUC1 residues.

11. The method of claim 1, wherein (a) the 3-5 positively-charged amino acid residues are arginine and/or lysine, and/or (b) the positively-charged amino acid residues corresponding to native MUC1 residues are arginine and/or lysine.

12. The method of claim 1, further comprising contacting the cell with a second anti-cancer agent.

13. The method of claim 10, wherein the second anti-cancer agent is contacted prior to the peptide.

14. The method of claim 10, wherein the second anti-cancer agent is contacted after the peptide.

15. The method of claim 10, wherein the second anti-cancer agent is contacted at the same time as the peptide.

16. The method of claim 1, wherein the peptide comprises all L amino acids.

17. The method of claim 1, wherein the peptide comprises all D amino acids.

18. The method of claim 1, wherein the peptide comprises a mix of L and D amino acids.

19. The method of claim 1, wherein the peptide is a stapled peptide.

20. The method of claim 1, wherein the peptide is a cyclized peptide.

21. The method of claim 1, wherein the peptide is a peptidomimetic or peptoid.

22. The method of claim 1, wherein inhibiting comprises inhibiting cancer cell growth.

23. The method of claim 1, wherein inhibiting comprises inhibiting cancer cell proliferation.

24. The method of claim 1, wherein inhibiting comprises inducing cancer cell death.

25. The method of claim 24, wherein cancer cell death is by apoptosis or necrosis.

26. A method of inhibiting MUC1-positive cancer in a subject comprising administering to the subject a MUC1 peptide of 50 residues or less and comprising at least 4 consecutive MUC1 residues and no more than 20 consecutive MUC1 residues and comprising the sequence CQC (SEQ ID NO:4), wherein:
(i) the amino-terminal cysteine of CQC is covered on its NH2-terminus by at least one amino acid residue that need not correspond to the native MUC1 transmembrane sequence; and
(ii) the peptide comprises 3-5 consecutive positively-charged amino acid residues in addition to those positively-charged amino acid residues corresponding to native MUC1 residues.

27. The method of claim 1, wherein the 3-5 positively-charged residues are located at the NH2-terminus of the peptide.

* * * * *

UNITED STATES PATENT AND TRADEMARK OFFICE
CERTIFICATE OF CORRECTION

PATENT NO.       : 8,685,928 B2
APPLICATION NO.  : 13/026858
DATED            : April 1, 2014
INVENTOR(S)      : Donald W. Kufe and Surender Kharbanda It is certified that error appears in the above-identified patent and that said Letters Patent is hereby corrected as shown below:

In title page, item (56) References Cited - Other Publications, delete the 6th reference on page 2 "Yin et al., "MUC1-C oncoprotein suppresses reactive oxygen species-induced terminal differentiation of acute myelogenous leukemia cells," Blood., 1 17(18):4863-4870, May 5, 2011. E-published Mar. 21, 2011." and replace with --Yin et al., "MUC1-C oncoprotein suppresses reactive oxygen species-induced terminal differentiation of acute myelogenous leukemia cells," Blood., 117(18):4863-4870, May 5, 2011. E-published Mar. 21, 2011.-- therefor.

In title page, item (56) References Cited - Other Publications, delete the 9th reference on page 2 "Abe and Kufe, "Structural analysis of the DF3 human breast carcinoma-associated protein," Cancer Res., 49(1):2834-2839, 1989." and replace with --Abe and Kufe, "Structural analysis of the DF3 human breast carcinoma-associated protein," Cancer Res., 49(11):2834-2839, 1989.-- therefor.

In title page, item (56) References Cited - Other Publications, delete the 22nd reference on page 2 "Hodel ei al., "The three-dimensional structure of the autoproteolytic, nuclear pore-targeting domain of the human nucleoporin Nup98," Mol. Cell, 10(2):347-58, 2002." and replace with --Hodel et al., "The three-dimensional structure of the autoproteolytic, nuclear pore-targeting domain of the human nucleoporin Nup98," Mol. Cell, 10(2):347-58, 2002.-- therefor.

In title page, item (56) References Cited - Other Publications, delete the 23rd reference on page 2 "Hruby, "Designing peptide receptor agonists and antagonists," Nature Reviews. Drug Discovery, 1:847-585, 2002." and replace with --Hruby, "Designing peptide receptor agonists and antagonists," Nature Reviews. Drug Discovery, 1:847-858, 2002.-- therefor.

In title page, item (56) References Cited - Other Publications, delete the 24th reference on page 2 "Hu at al.," MUC1 cytoplasmic tail: a potential therapeutic target for ovarian cancer," Future Drugs, 6(8). 1261-1271, 2006." and replace with --Hu et al.," MUC1 cytoplasmic tail: a potential therapeutic target for ovarian cancer," Future Drugs, 6(8).1261-1271, 2006-- therefor.

Signed and Sealed this
First Day of July, 2014

Michelle K. Lee
*Deputy Director of the United States Patent and Trademark Office*

CERTIFICATE OF CORRECTION (continued)
U.S. Pat. No. 8,685,928 B2

In title page, item (56) References Cited - Other Publications, delete the 25th reference on page 2 "Huang at al., "MUC1 cytoplasmic domain coactivates Wnt target gene transcription and confers transformation." Cancer Biol. Ther., 2(6): 702-706, 2003." and replace with --Huang et al., "MUC1 cytoplasmic domain coactivates Wnt target gene transcription and confers transformation." Cancer Biol. Ther., 2(6): 702-706, 2003.-- therefor.

In title page, item (56) References Cited - Other Publications, delete the 26th reference on page 2 "Huang at al., "MUC1 oncoprotein blocks glycogen synthase kinase 3beta-mediated phosphorylation and degradation of beta-catenin," Cancer Res., 65:10413-10422, 2005." and replace with --Huang et al., "MUC1 oncoprotein blocks glycogen synthase kinase 3beta-mediated phosphorylation and degradation of beta-catenin," Cancer Res., 65:10413-10422, 2005.-- therefor.

In title page, item (56) References Cited - Other Publications, delete the 30th reference on page 2 "Khodarev et al., "Cooperativity of the MUC1 oncoprotein and STAT1 pathway in poor prognosis human breast cancer," Oncogene, 29(6):920-929, 2010. B-published Nov. 16, 2009." and replace with --Khodarev et al., "Cooperativity of the MUC1 oncoprotein and STAT1 pathway in poor prognosis human breast cancer," Oncogene, 29 (6):920-929, 2010. E-published Nov. 16, 2009.-- therefor.

In title page, item (56) References Cited - Other Publications, delete the 31st reference on page 2 "Kinkiugh et al., "Recycling of MUC1 is dependent on its palmitoylation," The Journal of Biological Chemistry, 281 (17):12112-12122, 2006." and replace with --Kinlough et al., "Recycling of MUC1 is dependent on its palmitoylation," The Journal of Biological Chemistry, 281(17):12112-12122, 2006.-- therefor.

In title page, item (56) References Cited - Other Publications, delete the 34th reference on page 2 "Kufe, "Human MUC1 oncoprotein is of functional importance fo the development of prostate cancer," Award No. W81XWH-08-1-0093, Annual Report, prepared for U.S. Army Medical Research and Materiel Command, Mar. 2009." and replace with --Kufe, "Human MUC1 oncoprotein is of functional importance to the development of prostate cancer," Award No. W81XWH-08-1-0093, Annual Report, prepared for U.S. Army Medical Research and Materiel Command, Mar. 2009.-- therefor.

In title page, item (56) References Cited - Other Publications, delete the 40th reference on page 2 "Li et al., "Hereguhn targets ganinia-catenin to the nucleolus by a mechanism dependent on the DF3/MUC1 oncoprotein," Mol. Cancer Res., 1(10):765-775, 2003." and replace with --Li et al., "Hereguhn targets ganinia-catenin to the nucleolus by a mechanism dependent on the DF3/MUC1 oncoprotein," Mol. Cancer Res., 1(10):765-.-- therefor.

In title page, item (56) References Cited - Other Publications, delete the 26th reference on page 2 "Huang at al., "MUC1 oncoprotein blocks glycogen synthase kinase 3beta-mediated phosphorylation and degradation of beta-catenin," Cancer Res., 65:10413-10422, 2005." and replace with --Huang et al., "MUC1 oncoprotein blocks glycogen synthase kinase 3beta-mediated phosphorylation and degradation of beta-catenin," Cancer Res., 65:10413-10422, 2005.-- therefor.

CERTIFICATE OF CORRECTION (continued)
U.S. Pat. No. 8,685,928 B2

In title page, item (56) References Cited - Other Publications, delete the 30th reference on page 2 "Khodarev et al., "Cooperativity of the MUC1 oncoprotein and STAT1 pathway in poor prognosis human breast cancer," Oncogene, 29(6):920-929, 2010. B-published Nov. 16, 2009." and replace with --Khodarev et al., "Cooperativity of the MUC1 oncoprotein and STAT1 pathway in poor prognosis human breast cancer," Oncogene, 29 (6):920-929, 2010. E-published Nov. 16, 2009.-- therefor.

In title page, item (56) References Cited - Other Publications, delete the 31st reference on page 2 "Kinkiugh et al., "Recycling of MUC1 is dependent on its palmitoylation," The Journal of Biological Chemistry, 281 (17):12112-12122, 2006." and replace with --Kinlough et al., "Recycling of MUC1 is dependent on its palmitoylation," The Journal of Biological Chemistry, 281(17):12112-12122, 2006.-- therefor.

In title page, item (56) References Cited - Other Publications, delete the 34th reference on page 2 "Kufe, "Human MUC1 oncoprotein is of functional importance fo the development of prostate cancer," Award No. W81XWH-08-1-0093, Annual Report, prepared for U.S. Army Medical Research and Materiel Command, Mar. 2009." and replace with --Kufe, "Human MUC1 oncoprotein is of functional importance to the development of prostate cancer," Award No. W81XWH-08-1-0093, Annual Report, prepared for U.S. Army Medical Research and Materiel Command, Mar. 2009.-- therefor.

In title page, item (56) References Cited - Other Publications, delete the 20th reference on page 3 "Spicer et al., "Molecular cloning and analysis of the mouse homologue of the tumor-associated mucin, MUC1, reveals conservation of potential O-glycosylation.sites, transmembrance, and cytoplasmic domains, and a loss of minisatellite-like polymorphism," J Biol. Chem., 266(23): 15099-15109, 1991." and replace with --Spicer et al., "Molecular cloning and analysis of the mouse homologue of the tumor-associated mucin, MUC1, reveals conservation of potential O-glycosylation sites, transmembrane, and cytoplasmic domains, and a loss of minisatellite-like polymorphism," J Biol. Chem., 266(23): 15099-15109, 1991.-- therefor.

In title page, item (56) References Cited - Other Publications, delete the 24th reference on page 3 "Tsutsumida et. al., "RNA interference suppression of MUC1 reduced the growth rate and metastatic phenotype of human pancreatic cancer cells," Clin. Cancer Rev., 12(10):2976-2987, 2006." and replace with --Tsutsumida et al., "RNA interference suppression of MUC1 reduced the growth rate and metastatic phenotype of human pancreatic cancer cells," Clin. Cancer Rev., 12(10):2976-2987, 2006.-- therefor.

In title page, item (56) References Cited - Other Publications, delete the 25th reference on page 3 "Vermeer et al.. "Segregation of receptor and ligand regulates activation of epithelial growth factor receptor," Nature, 422 (6929):322-6, 2003." and replace with --Vermeer et al., "Segregation of receptor and ligand regulates activation of epithelial growth factor receptor," Nature, 422(6929):322-6, 2003.-- therefor.

CERTIFICATE OF CORRECTION (continued)
U.S. Pat. No. 8,685,928 B2

In title page, item (56) References Cited - Other Publications, delete the 32nd reference on page 3 "Yin et al., "MUC1 oneoptotein activates the FOXO3a transcription factor in a survival response to oxidative stress," J Biol. Chem., 279(44):45721-45727, 2004." and replace with --Yin et al., "MUC1 oncoprotein activates the FOXO3a transcription factor in a survival response to oxidative stress," J Biol. Chem., 279(44):45721-45727, 2004.-- therefor.

UNITED STATES PATENT AND TRADEMARK OFFICE
CERTIFICATE OF CORRECTION

PATENT NO.         : 8,685,928 B2
APPLICATION NO.    : 13/026858
DATED              : April 1, 2014
INVENTOR(S)        : Donald W. Kufe and Surender Kharbanda It is certified that error appears in the above-identified patent and that said Letters Patent is hereby corrected as shown below:

In title page, item (56) References Cited - Other Publications, delete the 6th reference on page 2 "Yin et al., "MUC1-C oncoprotein suppresses reactive oxygen species-induced terminal differentiation of acute myelogenous leukemia cells," Blood., 1 17(18):4863-4870, May 5, 2011. E-published Mar. 21, 2011." and replace with --Yin et al., "MUC1-C oncoprotein suppresses reactive oxygen species-induced terminal differentiation of acute myelogenous leukemia cells," Blood., 117(18):4863-4870, May 5, 2011. E-published Mar. 21, 2011.-- therefor.

In title page, item (56) References Cited - Other Publications, delete the 9th reference on page 2 "Abe and Kufe, "Structural analysis of the DF3 human breast carcinoma-associated protein," Cancer Res., 49(1):2834-2839, 1989." and replace with --Abe and Kufe, "Structural analysis of the DF3 human breast carcinoma-associated protein," Cancer Res., 49(11):2834-2839, 1989.-- therefor.

In title page, item (56) References Cited - Other Publications, delete the 22nd reference on page 2 "Hodel ei al., "The three-dimensional structure of the autoproteolytic, nuclear pore-targeting domain of the human nucleoporin Nup98," Mol. Cell, 10(2):347-58, 2002." and replace with --Hodel et al., "The three-dimensional structure of the autoproteolytic, nuclear pore-targeting domain of the human nucleoporin Nup98," Mol. Cell, 10(2):347-58, 2002.-- therefor.

In title page, item (56) References Cited - Other Publications, delete the 23rd reference on page 2 "Hruby, "Designing peptide receptor agonists and antagonists," Nature Reviews. Drug Discovery, 1:847-585, 2002." and replace with --Hruby, "Designing peptide receptor agonists and antagonists," Nature Reviews. Drug Discovery, 1:847-858, 2002.-- therefor.

In title page, item (56) References Cited - Other Publications, delete the 24th reference on page 2 "Hu at al.," MUC1 cytoplasmic tail: a potential therapeutic target for ovarian cancer," Future Drugs, 6(8). 1261-1271, 2006." and replace with --Hu et al.," MUC1 cytoplasmic tail: a potential therapeutic target for ovarian cancer," Future Drugs, 6(8).1261-1271, 2006-- therefor.

This certificate supersedes the Certificate of Correction issued July 1, 2014.

<div style="text-align: right;">
Signed and Sealed this<br>
Seventh Day of October, 2014
</div>

<div style="text-align: right;">
Michelle K. Lee<br>
<em>Deputy Director of the United States Patent and Trademark Office</em>
</div>

CERTIFICATE OF CORRECTION (continued)
U.S. Pat. No. 8,685,928 B2

In title page, item (56) References Cited - Other Publications, delete the 25th reference on page 2 "Huang at al., "MUC1 cytoplasmic domain coactivates Wnt target gene transcription and confers transformation." Cancer Biol. Ther., 2(6): 702-706, 2003." and replace with --Huang et al., "MUC1 cytoplasmic domain coactivates Wnt target gene transcription and confers transformation." Cancer Biol. Ther., 2(6): 702-706, 2003.-- therefor.

In title page, item (56) References Cited - Other Publications, delete the 26th reference on page 2 "Huang at al., "MUC1 oncoprotein blocks glycogen synthase kinase 3beta-mediated phosphorylation and degradation of beta-catenin," Cancer Res., 65:10413-10422, 2005." and replace with --Huang et al., "MUC1 oncoprotein blocks glycogen synthase kinase 3beta-mediated phosphorylation and degradation of beta-catenin," Cancer Res., 65:10413-10422, 2005.-- therefor.

In title page, item (56) References Cited - Other Publications, delete the 30th reference on page 2 "Khodarev et al., "Cooperativity of the MUC1 oncoprotein and STAT1 pathway in poor prognosis human breast cancer," Oncogene, 29(6):920-929, 2010. B-published Nov. 16, 2009." and replace with --Khodarev et al., "Cooperativity of the MUC1 oncoprotein and STAT1 pathway in poor prognosis human breast cancer," Oncogene, 29 (6):920-929, 2010. E-published Nov. 16, 2009.-- therefor.

In title page, item (56) References Cited - Other Publications, delete the 31st reference on page 2 "Kinkiugh et al., "Recycling of MUC1 is dependent on its palmitoylation," The Journal of Biological Chemistry, 281 (17):12112-12122, 2006." and replace with --Kinlough et al., "Recycling of MUC1 is dependent on its palmitoylation," The Journal of Biological Chemistry, 281(17):12112-12122, 2006.-- therefor.

In title page, item (56) References Cited - Other Publications, delete the 34th reference on page 2 "Kufe, "Human MUC1 oncoprotein is of functional importance fo the development of prostate cancer," Award No. W81XWH-08-1-0093, Annual Report, prepared for U.S. Army Medical Research and Materiel Command, Mar. 2009." and replace with --Kufe, "Human MUC1 oncoprotein is of functional importance to the development of prostate cancer," Award No. W81XWH-08-1-0093, Annual Report, prepared for U.S. Army Medical Research and Materiel Command, Mar. 2009.-- therefor.

In title page, item (56) References Cited - Other Publications, delete the 40th reference on page 2 "Li et al., "Heregulin targets ganinia-catenin to the nucleolus by a mechanism dependent on the DF3/MUC1 oncoprotein," Mol. Cancer Res., 1(10):765-775, 2003." and replace with --Li et al., "Heregulin targets gamma-catenin to the nucleolus by a mechanism dependent on the DF3/MUC1 oncoprotein," Mol. Cancer Res., 1(10):765-775-- therefor.

In title page, item (56) References Cited - Other Publications, delete the 26th reference on page 2 "Huang at al., "MUC1 oncoprotein blocks glycogen synthase kinase 3beta-mediated phosphorylation and degradation of beta-catenin," Cancer Res., 65:10413-10422, 2005." and replace with --Huang et al., "MUC1 oncoprotein blocks glycogen synthase kinase 3beta-mediated phosphorylation and degradation of beta-catenin," Cancer Res., 65:10413-10422, 2005.-- therefor.

CERTIFICATE OF CORRECTION (continued)
U.S. Pat. No. 8,685,928 B2

In title page, item (56) References Cited - Other Publications, delete the 30th reference on page 2 "Khodarev et al., "Cooperativity of the MUC1 oncoprotein and STAT1 pathway in poor prognosis human breast cancer," Oncogene, 29(6):920-929, 2010. B-published Nov. 16, 2009." and replace with --Khodarev et al., "Cooperativity of the MUC1 oncoprotein and STAT1 pathway in poor prognosis human breast cancer," Oncogene, 29 (6):920-929, 2010. E-published Nov. 16, 2009.-- therefor.

In title page, item (56) References Cited - Other Publications, delete the 31st reference on page 2 "Kinkiugh et al., "Recycling of MUC1 is dependent on its palmitoylation," The Journal of Biological Chemistry, 281 (17):12112-12122, 2006." and replace with --Kinlough et al., "Recycling of MUC1 is dependent on its palmitoylation," The Journal of Biological Chemistry, 281(17):12112-12122, 2006.-- therefor.

In title page, item (56) References Cited - Other Publications, delete the 34th reference on page 2 "Kufe, "Human MUC1 oncoprotein is of functional importance fo the development of prostate cancer," Award No. W81XWH-08-1-0093, Annual Report, prepared for U.S. Army Medical Research and Materiel Command, Mar. 2009." and replace with --Kufe, "Human MUC1 oncoprotein is of functional importance to the development of prostate cancer," Award No. W81XWH-08-1-0093, Annual Report, prepared for U.S. Army Medical Research and Materiel Command, Mar. 2009.-- therefor.

In title page, item (56) References Cited - Other Publications, delete the 41st reference on page 2 "Li et al., "Human DE3/MUC1 carcinoma-associated protein functions as an oncogene," Oncogene, 22 (38): 6107-6110, 2003." and replace with --Li et al., "Human DF3/MUC1 carcinoma-associated protein functions as an oncogene," Oncogene, 22 (38): 6107-6110, 2003.-- therefor.

In title page, item (56) References Cited - Other Publications, delete the 12th reference on page 3 "Ren et al., "Protein kinase C delta regulates function of the DE3/MUC1 carcinoma antigen in beta-catenin signaling," J. Biol. Chem., 277 (20):17616-17622, 2002." and replace with --Ren et al., "Protein kinase C delta regulates function of the DF3/MUC1 carcinoma antigen in beta-catenin signaling," J. Biol. Chem., 277 (20):17616-17622, 2002.-- therefor.

In title page, item (56) References Cited - Other Publications, delete the 16th reference on page 3 "Response to Office Communication issued in US. Appl. No. 12/789,177, dated Apr. 30, 2012." and replace with --Response to Office Communication issued in US. Appl. No. 12/789,127, dated Apr. 30, 2012.-- therefor.

In title page, item (56) References Cited - Other Publications, delete the 18th reference on page 3 "Schroeder et al.,"MUC1 overexpression results in mammary gland tumorieenesis and prolonged alveolar differentiation," Oncogene, 23 (34):5739-5747, 2004." and replace with --Schroeder et al.,"MUC1 overexpression results in mammary gland tumorigenesis and prolonged alveolar differentiation," Oncogene, 23 (34):5739-5747, 2004.-- therefor.

CERTIFICATE OF CORRECTION (continued)
U.S. Pat. No. 8,685,928 B2

In title page, item (56) References Cited - Other Publications, delete the 20th reference on page 3 "Spicer et al., "Molecular cloning and analysis of the mouse homologue of the tumor-associated mucin, MUC1, reveals conservation of potential O-glycosylation.sites, transmembrance, and cytoplasmic domains, and a loss of minisatellite-like polymorphism," J Biol. Chem., 266(23): 15099-15109, 1991." and replace with --Spicer et al., "Molecular cloning and analysis of the mouse homologue of the tumor-associated mucin, MUC1, reveals conservation of potential O-glycosylation sites, transmembrane, and cytoplasmic domains, and a loss of minisatellite-like polymorphism," J Biol. Chem., 266(23): 15099-15109, 1991.-- therefor.

In title page, item (56) References Cited - Other Publications, delete the 24th reference on page 3 "Tsutsumida et. al., "RNA interference suppression of MUC1 reduced the growth rate and metastatic phenotype of human pancreatic cancer cells," Clin. Cancer Rev., 12(10):2976-2987, 2006." and replace with --Tsutsumida et al., "RNA interference suppression of MUC1 reduced the growth rate and metastatic phenotype of human pancreatic cancer cells," Clin. Cancer Rev., 12(10):2976-2987, 2006.-- therefor.

In title page, item (56) References Cited - Other Publications, delete the 25th reference on page 3 "Vermeer et al.. "Segregation of receptor and ligand regulates activation of epithelial growth factor receptor," Nature, 422 (6929):322-6, 2003." and replace with --Vermeer et al., "Segregation of receptor and ligand regulates activation of epithelial growth factor receptor," Nature, 422(6929):322-6, 2003.-- therefor.

In title page, item (56) References Cited - Other Publications, delete the 32nd reference on page 3 "Yin et al., "MUC1 oneoptotein activates the FOXO3a transcription factor in a survival response to oxidative stress," J Biol. Chem., 279(44):45721-45727, 2004." and replace with --Yin et al., "MUC1 oncoprotein activates the FOXO3a transcription factor in a survival response to oxidative stress," J Biol. Chem., 279(44):45721-45727, 2004.-- therefor.